(12) United States Patent
Morley et al.

(10) Patent No.: US 10,709,610 B2
(45) Date of Patent: Jul. 14, 2020

(54) LASER METHODS AND SYSTEMS FOR ADDRESSING CONDITIONS OF THE LENS

(71) Applicant: Lensar, LLC, Orlando, FL (US)

(72) Inventors: Dustin Morley, Rockledge, FL (US);
Gary P. Gray, Orlando, FL (US);
Richard Ty Olmstead, Ovideo, FL (US)

(73) Assignee: Lensar, Inc., Orlando, FL (US)

( * ) Notice: Subject to any disclaimer, the term of this patent is extended or adjusted under 35 U.S.C. 154(b) by 153 days.

(21) Appl. No.: 15/130,845

(22) Filed: Apr. 15, 2016

(65) Prior Publication Data

US 2016/0302971 A1     Oct. 20, 2016

Related U.S. Application Data

(63) Continuation-in-part of application No. 14/444,366, filed on Jul. 28, 2014, and a continuation-in-part of
(Continued)

(51) Int. Cl.
*A61F 9/008* (2006.01)
*A61B 3/117* (2006.01)
(Continued)

(52) U.S. Cl.
CPC ........ *A61F 9/00825* (2013.01); *A61B 3/1176* (2013.01); *A61B 3/14* (2013.01); *A61F 9/00834* (2013.01); *A61F 9/00838* (2013.01); *G06F 19/328* (2013.01); *G16H 10/60* (2018.01); *A61B 8/10* (2013.01); *A61B 2017/00199* (2013.01); *A61B 2017/00221* (2013.01); *A61B 2034/107* (2016.02); *A61B 2090/309* (2016.02);
(Continued)

(58) Field of Classification Search
CPC .............. A61F 9/00825; A61F 9/00834; A61F 2009/00861; A61F 2009/0087; A61F 2009/00885; A61F 2009/00887; A61F 2009/00889; A61B 17/00; A61B 2017/00221; A61B 3/117; A61B 3/1173; A61B 3/1176; G16H 10/00; G16H 10/60; G06F 19/328; G06F 19/34; G06F 19/3418
USPC ............................................ 606/4–6, 10–12
See application file for complete search history.

(56) References Cited

U.S. PATENT DOCUMENTS

| 4,538,608 A | 9/1985 | L'Esperance |
| 4,764,930 A | 8/1988 | Bille |

(Continued)

FOREIGN PATENT DOCUMENTS

| CN | 101287418 A | 10/2008 |
| WO | WO 2006/07449 | 7/2006 |

OTHER PUBLICATIONS

Nov. 12, 2018, EPO, Examination Report Appl No. 16780945.8.
(Continued)

*Primary Examiner* — Ahmed M Farah
(74) *Attorney, Agent, or Firm* — Glen P. Belvis; Belvis Law, LLC.

(57) ABSTRACT

Systems and methods for performing laser cataract surgery, for using a biometric system to determine a material property of a structure of the eye, laser pulses in a laser shot pattern having different powers. A therapeutic laser, and laser delivery system having the capability to vary the power of the laser beam.

2 Claims, 36 Drawing Sheets

Related U.S. Application Data application No. 14/234,012, filed on Jan. 21, 2014, now abandoned, which is a continuation-in-part of application No. 13/681,004, filed on Nov. 19, 2012, now Pat. No. 8,708,491, which is a continuation-in-part of application No. 12/842,870, filed on Jul. 23, 2010, now Pat. No. 9,375,349, which is a continuation of application No. 12/509,454, filed on Jul. 25, 2009, now abandoned, which is a continuation-in-part of application No. 12/217,285, filed on Jul. 2, 2008, now Pat. No. 9,545,338, which is a continuation-in-part of application No. 12/217,295, filed on Jul. 2, 2008, now Pat. No. 9,889,043, which is a continuation of application No. PCT/US2007/001353, filed on Jan. 19, 2007, and a continuation-in-part of application No. 11/414,838, filed on May 1, 2006, now Pat. No. 8,262,646, which is a continuation-in-part of application No. 11/414,819, filed on May 1, 2006, now Pat. No. 9,180,051, which is a continuation-in-part of application No. 11/337,127, filed on Jan. 20, 2006.

(60) Provisional application No. 62/148,614, filed on Apr. 16, 2015, provisional application No. 61/228,560, filed on Jul. 25, 2009, provisional application No. 61/228,529, filed on Jul. 24, 2009, provisional application No. 61/135,950, filed on Jul. 25, 2008.

(51) Int. Cl.
| | |
|---|---|
| *A61B 3/14* | (2006.01) |
| *G06F 19/00* | (2018.01) |
| *G16H 10/60* | (2018.01) |
| *A61B 8/10* | (2006.01) |
| *A61B 17/00* | (2006.01) |
| *A61B 34/10* | (2016.01) |
| *A61B 90/00* | (2016.01) |
| *A61B 90/30* | (2016.01) |

(52) U.S. Cl.
CPC . *A61B 2090/371* (2016.02); *A61F 2009/0087* (2013.01); *A61F 2009/00844* (2013.01); *A61F 2009/00851* (2013.01); *A61F 2009/00857* (2013.01); *A61F 2009/00859* (2013.01); *A61F 2009/00872* (2013.01); *A61F 2009/00887* (2013.01); *A61F 2009/00889* (2013.01)

(56) References Cited

U.S. PATENT DOCUMENTS

| | | | |
|---|---|---|---|
| 4,901,718 A | 2/1990 | Bille | |
| 4,907,586 A | 3/1990 | Bille | |
| 5,246,435 A | 9/1993 | Bille | |
| 5,439,462 A | 8/1995 | Bille | |
| 6,004,314 A | 12/1999 | Wei | |
| 6,322,556 B1 | 11/2001 | Gwon | |
| 7,655,002 B2 | 2/2010 | Myers | |
| 7,801,271 B2* | 9/2010 | Gertner | A61N 5/1017 378/65 |
| 8,262,646 B2 | 9/2012 | Frey | |
| 8,360,577 B2* | 1/2013 | Nixon | A61B 3/1173 351/206 |
| 8,382,745 B2 | 2/2013 | Naranjo-Tackman | |
| 8,394,084 B2 | 3/2013 | Palankar et al. | |
| 8,403,921 B2 | 3/2013 | Palankar et al. | |
| 8,425,497 B2 | 4/2013 | Blumenkranz et al. | |
| 8,465,478 B2 | 6/2013 | Frey | |
| 8,480,659 B2 | 7/2013 | Frey | |
| 8,488,851 B2* | 7/2013 | Artal Soriano | A61B 3/1176 351/211 |
| 8,500,723 B2 | 8/2013 | Frey | |
| 8,617,146 B2 | 12/2013 | Frey | |
| 8,758,332 B2 | 6/2014 | Frey | |
| 8,801,186 B2 | 8/2014 | Frey | |
| 9,180,051 B2* | 11/2015 | Frey | A61F 9/008 |
| 9,375,349 B2* | 6/2016 | Frey | A61F 9/008 |
| 9,545,338 B2 | 1/2017 | Frey | |
| 2002/0049511 A1 | 4/2002 | Brandinger | |
| 2007/0173794 A1 | 7/2007 | Frey | |
| 2008/0249800 A1 | 10/2008 | Karamchedu | |
| 2008/0287928 A1 | 11/2008 | Arnoldussen | |
| 2009/0012507 A1* | 1/2009 | Culbertson | A61F 2/16 606/6 |
| 2010/0004641 A1 | 1/2010 | Frey | |
| 2010/0118266 A1* | 5/2010 | Nixon | A61B 3/1173 351/206 |
| 2010/0195876 A1* | 8/2010 | Artal Soriano | A61B 3/101 382/128 |
| 2010/0292678 A1* | 11/2010 | Frey | A61F 9/008 606/5 |
| 2012/0016352 A1 | 1/2012 | Dick | |
| 2012/0155726 A1* | 6/2012 | Li | A61B 3/1173 382/128 |
| 2012/0182522 A1* | 7/2012 | Frey | A61B 3/14 351/206 |
| 2012/0316545 A1* | 12/2012 | Blumenkranz | A61F 9/00736 606/6 |
| 2015/0141972 A1* | 5/2015 | Woodley | A61B 3/102 606/5 |
| 2016/0150952 A1* | 6/2016 | Raymond | A61F 9/00804 351/205 |
| 2016/0302971 A1 | 10/2016 | Morley | |
| 2017/0056243 A1* | 3/2017 | Schuele | A61B 3/102 |
| 2017/0266042 A1* | 9/2017 | Palanker | A61F 9/00736 |
| 2017/0290703 A1* | 10/2017 | Teuma | A61F 9/013 |

OTHER PUBLICATIONS

May 3, 2018, AU Patent Office, P282621 Exam Rpt No. 1.
Apr. 12, 2019, AU Patent Office, P282621 Exam Rpt No. 2.
Aug. 9, 2016, PCT, PCT/US16/27980 Search Report.
Aug. 9, 2016, PCT, PCT/US16/27980 Written Opinion.
Jul. 3, 2019, CNIPA, 2201680022143.X Office Action (Translation).

\* cited by examiner

ANTERIOR ⟵⟶ POSTERIOR

ANTERIOR ⟵⟶ POSTERIOR

Iris boundary and eyelid interference detection for a CA-200F image

Iris boundary detection for treatment image

Approximating a circular arc using 3 line segments

Image filtering procedure for eyelid interference detection

Example results of eyelid/eyelash interference detection

FIG. 15A
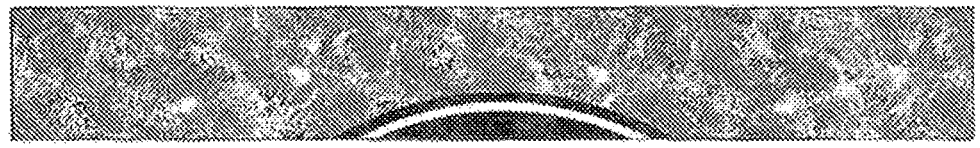
FIG. 15B
Unwrapped, DOG filtered iris (treatment top, topographer bottom)
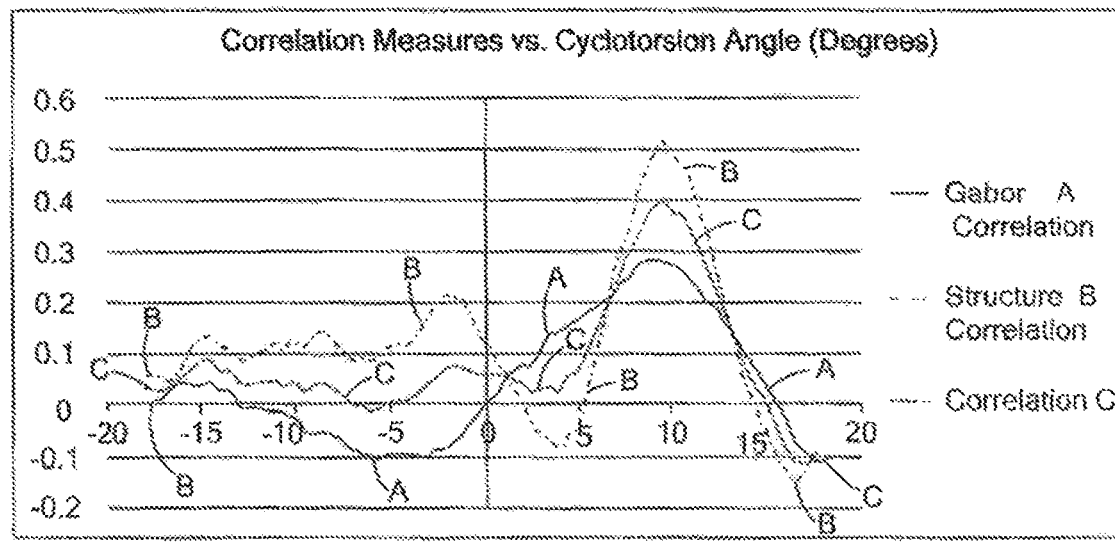
FIG. 16 Correlation measures as a function of proposed cyclotorsion angle
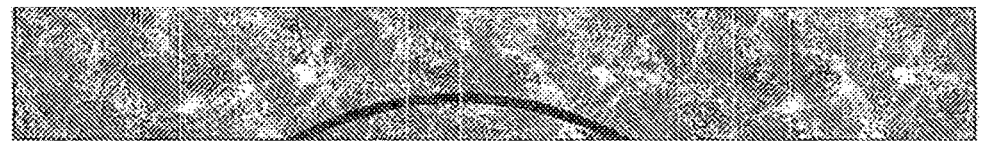
FIG. 17A
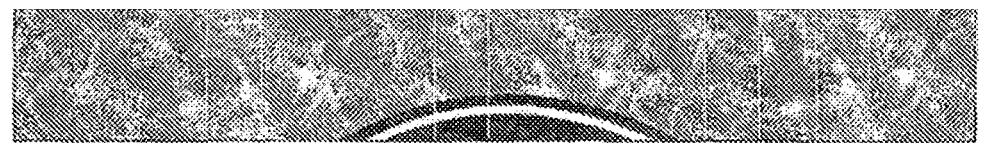
FIG. 17B    Registration result

| Astigmatism to be treated (D) | Recommended arcuate cut angle |
|---|---|
| 0.60 < 1.00 D | 35 degrees |
| 1.00 < 1.50 D | 50 degrees |
| 1.50 < 2.00 D | 75 degrees |

| Astigmatism to be treated (D) | Recommended arcuate cut angle |
|---|---|
| 0.75 < 1.00 D (s) | 45 degrees |
| 1.00 < 1.50 D (p) | 60 degrees |
| 1.50 < 2.00 D (p) | 80 degrees |

S- single opposite incision
P- paired incision
Preop cylinder determined by Cassini True Corneal Power

FIG. 19

LASER METHODS AND SYSTEMS FOR ADDRESSING CONDITIONS OF THE LENS

This application: (i) claims under 35 U.S.C. § 119(e)(1) the benefit of the filing date of Apr. 16, 2015 of U.S. provisional application Ser. No. 62/148,614, which:
(ii) is a continuation-in-part of Ser. No. 14/234,012 filed Mar. 24, 2014, which is a continuation-in-part of U.S. patent application Ser. No. 13/681,004 filed Nov. 19, 2012, now issued as U.S. Pat. No. 8,708,491, which is a continuation of U.S. patent application Ser. No. 12/509,454 filed Jul. 25, 2009, which claims, under 35 U.S.C. § 119(e)(1), the benefit of the filing date of Jul. 25, 2008 of U.S. provisional application Ser. No. 61/135,950;
(iii) is a continuation-in-part of U.S. patent application Ser. No. 12/217,285 filed Jul. 2, 2008, which is a continuation of PCT/US07/01353 filed Jan. 19, 2007, which is a continuation-in-part of U.S. patent application Ser. No. 11/414,838 filed May 1, 2006, now issued as U.S. Pat. No. 8,262,646, a continuation-in-part of U.S. patent application Ser. No. 11/414,819 filed May 1, 2006, now issued as U.S. Pat. No. 9,180,051, and a continuation-in-part of U.S. patent application Ser. No. 11/337,127 filed Jan. 20, 2006;
(iv) is a continuation-in-part of U.S. patent application Ser. No. 11/414,819 filed May 1, 2006, now issued as U.S. Pat. No. 9,180,051;
(v) is a continuation-in-part of U.S. patent application Ser. No. 11/337,127 filed Jan. 20, 2006;
(vi) is a continuation-in-part of Ser. No. 12/842,870 filed Jul. 23, 2010, which claims, under 35 U.S.C. § 119(e)(1), the benefit of the filing date of Jul. 24, 2009 of U.S. provisional application Ser. No. 61/228,560 and the benefit of the filing date of Jul. 25, 2009 of U.S. provisional application Ser. No. 61/228,529;
(vii) is a continuation-in-part of U.S. patent application Ser. No. 12/217,295 filed Jul. 2, 2008; and,
(viii) is a continuation-in-part of U.S. patent application Ser. No. 14/444,366 filed Jul. 28, 2014, the entire disclosures of each of which are incorporated herein by reference.

BACKGROUND OF THE INVENTION

Field of the Invention

The present invention relates to systems and methods for treating the structure of the natural human crystalline lens with a laser to address a variety of medical conditions such as presbyopia, refractive error and cataracts and combinations of these.

The anatomical structures of the eye are shown in general in FIG. 1, which is a across sectional view of the eye. The sclera 131 is the while tissue that surrounds the lens 103 except at the cornea 101. The cornea 101 is the transparent tissue that comprises the exterior surface of the eye through which light first enters the eye. The iris 102 is a colored, contractible membrane that controls the amount of light entering the eye by changing the size of the circular aperture at its center (the pupil). The ocular or natural crystalline lens 103, a more detailed picture of which is shown in FIG. 1A, (utilizing similar reference numbers for similar structures) is located just posterior to the iris 102. The terms ocular lens, natural crystalline lens, natural lens, natural human crystalline lens, and lens (when referring to the prior terms) are used interchangeably herein and refer to the same anatomical structure of the human eye.

Generally, the ocular lens changes shape through the action of the ciliary muscle 108 to allow for focusing of a visual image. A neural feedback mechanism from the brain allows the ciliary muscle 108, acting through the attachment of the zonules 111, to change the shape of the ocular lens. Generally, sight occurs when light enters the eye through the cornea 101 and pupil, then proceeds through the ocular lens 103 through the vitreous 110 along the visual axis 104, strikes the retina 105 at the back of the eye, forming an image at the macula 106 that is transferred by the optic nerve 107 to the brain. The space between the cornea 101 and the retina 105 is filed with a liquid called the aqueous 117 in the anterior chamber 109 and the vitreous 110, a gel-like clear substance, in the chamber posterior to the lens 103.

FIG. 1A illustrates, in general, components of and related to the lens 103 for a typical 50-year old individual. The lens 103 is a multi-structural system. The lens 103 structure includes a cortex 113, and a nucleus 129, and a lens capsule 114. The capsule 114 is an outer membrane that envelopes the other interior structures of the lens. The lens epithelium 123 forms at the lens equatorial 121 generating ribbon-like cells or fibrils that grow anteriorly and posteriorly around the ocular lens. The nucleus 129 is formed from successive additions of the cortex 113 to the nuclear regions. The continuum of layers in the lens, including the nucleus 129, can be characterized into several layers, nuclei or nuclear regions. These layers include an embryonic nucleus 122, a fetal nucleus 130, both of which develop in the womb, an infantile nucleus 124, which develops from birth through four years for an average of about three years, an adolescent nucleus 126, which develops from about four years until puberty which averages about 12 years, and the adult nucleus 128, which develops at about 18 years and beyond.

The embryonic nucleus 122 is about 0.5 mm in equatorial diameter (width) and 0.425 mm in Anterior-Posterior axis 104 (AP axis) diameter (thickness). The fetal nucleus 130 is about 6.0 mm in equatorial diameter and 3.0 mm in AP axis 104 diameter. The infantile nucleus 124 is about 7.2 mm in equatorial diameter and 3.6 mm in AP axis 104 diameter. The adolescent nucleus 126 is about 9.0 mm in equatorial diameter and 4.5 mm in AP axis 104 diameter. The adult nucleus 128 at about age 36 is about 9.6 mm in equatorial diameter and 4.8 mm in AP axis 104 diameter. These are all average values for a typical adult human lens approximately age 50 in the accommodated state, ex vivo. Thus this lens (nucleus and cortex) is about 9.8 mm in equatorial diameter and 4.9 mm in AP axis 104 diameter. Thus, the structure of the lens is layered or nested, with the oldest layers and oldest cells towards the center.

The lens is a biconvex shape as shown in FIGS. 1 and 1A. The anterior and posterior sides of the lens have different curvatures and the cortex and the different nuclei in general follow those curvatures. Thus, the lens can be viewed as essentially a stratified structure that is asymmetrical along the equatorial axis and consisting of long crescent fiber cells arranged end to end to form essentially concentric or nested shells. The ends of these cells align to form suture lines in the central and paracentral areas both anteriorly and posteriorly. The older tissue in both the cortex and nucleus has reduced cellular function, having lost their cell nuclei and other organelles several months after cell formation.

Compaction of the lens occurs with aging. The number of lens fibers that grow each year is relatively constant throughout life. However, the size of the lens does not become as large as expected from new fiber growth. The lens grows from birth through age 3, from 6 mm to 7.2 mm or 20% growth in only 3 years. Then the next approximate decade, growth is from 72 mm to 9 mm or 25%; however, this is over a 3 times longer period of 9 years. Over the next approximate 2 decades, from age 12 to age 36 the lens grows from 9 mm to 9.6 mm or 6.7% growth in 24 years, showing a dramatically slowing observed growth rate, while we believe there is a relatively constant rate of fiber growth during this period. Finally, in the last approximately 2 decades described, from age 36 to age 54, the lens grows by a tiny fraction of its youthful growth, from 9.6 to 9.8 mm or 2.1% in 18 years. Although there is a geometry effect of needing more lens fibers to fill larger outer shells, the size of the older lens is considerably smaller than predicted by fiber growth rate models, which consider geometry effects. Fiber compaction including nuclear fiber compaction is thought to explain these observations.

In general, presbyopia is the loss of accommodative amplitude. In general refractive error is typically due to variations in the axial length of the eye. Myopia is when the eye is too long resulting in the focus falling in front of the retina. Hyperopia is when the eye is too short resulting in the focus falling behind the retina. In generally, cataracts are areas of opacification of the ocular lens which are sufficient to interfere with vision. Other conditions, for which the present invention is directed, include but are not limited to the opacification of the ocular lens.

Presbyopia most often presents as a near vision deficiency, the inability to read small print, especially in dim lighting after about 40-45 years of age. Presbyopia, or the loss of accommodative amplitude with age, relates to the eyes inability to change the shape of the natural crystalline lens, which allows a person to change focus between far and near, and occurs in essentially 100% of the population. Accommodative amplitude has been shown to decline with age steadily through the fifth decade of life.

In general, current presbyopia treatments tend to be directed toward alternatives to increasing the amplitude of accommodation of the natural crystalline lens. These treatments include a new class of artificial accommodative Intraocular Lenses (IOL's), such as the Eyeonics CRYSTAL-ENS, which are designed to change position within the eye; however, they offer only about 1 diopter of objectively measured accommodative amplitude, while many practitioners presently believe 3 or more diopters are required to restore normal visual function for near and far objects. Moreover, researchers are pursuing techniques and materials to refill the lens capsule with synthetic materials. Additionally, present surgical techniques to implant artificial accommodative IOL's are those developed for the more serious condition of cataracts. It is believed that practitioners are reluctant at the present time to replace a patient's clear albeit presbyopic natural crystalline lens, with an accommodative IOL due to the risks of this invasive surgical technique on a patient who may simply wear reading glasses to correct the near vision deficiency. However, developments may offer greater levels of accommodative amplitude in implantable devices and refilling materials.

SUMMARY

There has existed a long standing need for improved methods of increasing the efficacy of treatments for cataracts, including improved capsulotomies, removal of the natural lens, placement of IOLs, pre- and post procedure monitoring of patients, and the integration of data and records. The present inventions, among other things, solve these and other needs by providing the articles of manufacture, devices and processes set forth in this specification, drawings and claims.

BRIEF DESCRIPTION OF THE DRAWINGS

FIGS. 15 A-B show possible images showing the results of unwrapping an image of an iris and performing DOG filtering per the process shown in FIG. 9.

FIG. 16 shows a graph of a possible correlation measures vs. cyclotorsion angle relationship per the process shown in FIG. 9.

FIGS. 17 A-B show possible images showing the results of registration per the process shown in FIG. 9.

FIG. 19 shows a planning table for us in the development of a treatment plan.

DESCRIPTION OF THE PREFERRED EMBODIMENTS

In general, embodiments of the present inventions provide systems and methods for addressing cataracts and opacifications of the natural crystalline lens.

In general, embodiments of the present inventions further relate to methods and systems for determining the shape and position of the natural human crystalline lens and cornea relative to a laser device so as to provide an enhanced method and system for applying a laser to the lens and cornea.

Embodiments of the present invention additionally relate to systems and methods that provide predetermined, precise and reproducible laser shot patterns that are reproducible from patient to patient and surgeon to surgeon. Embodiments of the present invention additionally relate to systems and methods to determine, e.g., grade the degree of a cataract, determine the relative location within the lens of different levels of opacifications, determine the relative location within the lens of different levels of increased density, e.g., different levels of hardness, compaction, toughness of the natural lens, increased density, and compaction, and provide a laser beam of varying power, with the power being predetermined to correspond to the degree of increased density, e.g., a predetermined shot pattern having specific, and varied in a predetermined manner, laser powers that correspond to the determined density, grade or other material properties of the lens. Embodiments of the present inventions in addition relate to controllers, computers, and networks for the management, use, communication, storage and distribution of patient data, laser system status, shot pattern, procedure information that has been aggregated, and medical records. Embodiments of the present inventions provide for the use of topography, topographic images, and similar visualization, to be used in conjunction with, e.g., overlaid, integrated with, the calculated location and position of the structures of the lens.

Figure 1:
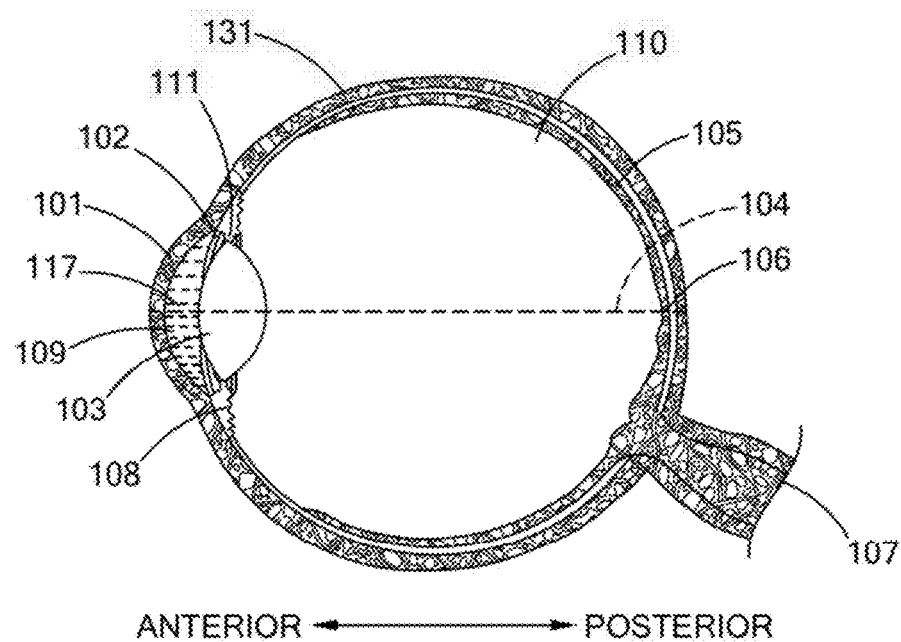
FIGS. 1 and 1A are cross sectional representations of the human eye.
Figure 1A:
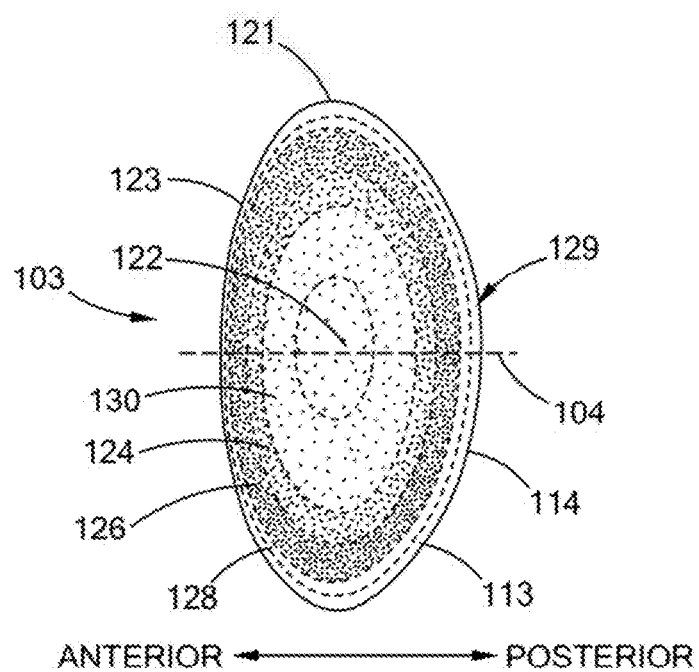
Figure 2:
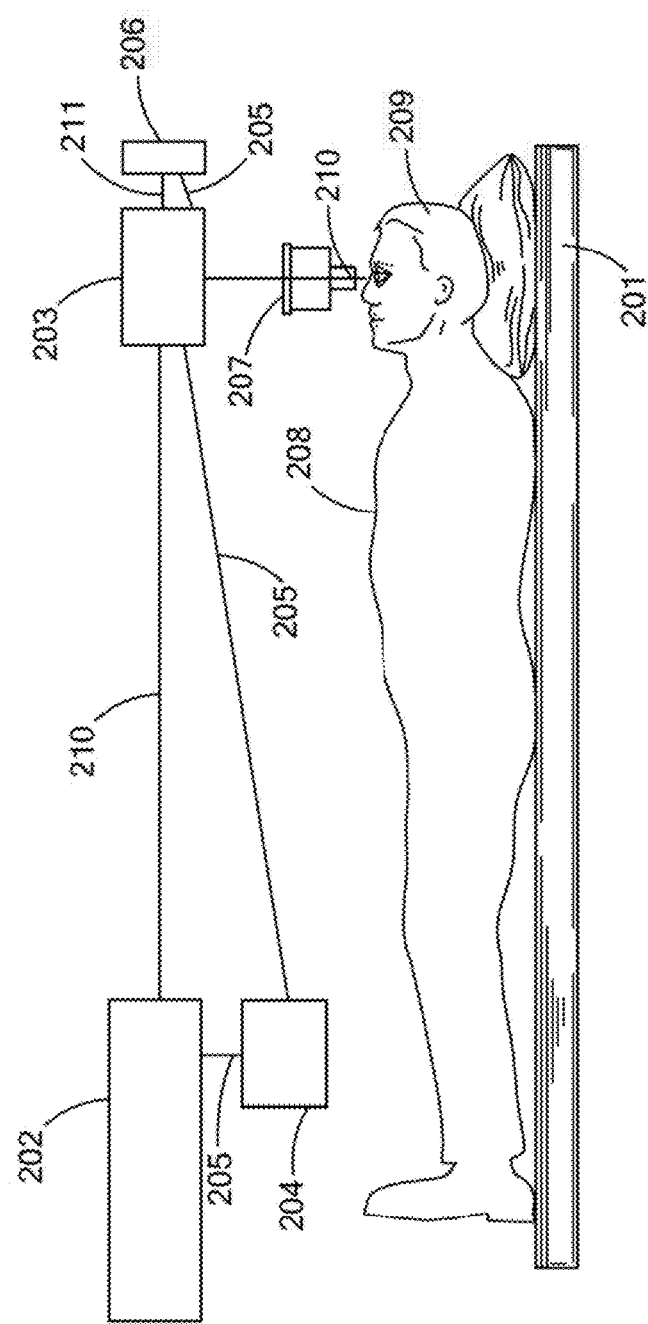
FIG. 2 is a block schematic diagram of a type of system for delivering a laser beam shot pattern to the lens of an eye according to the teachings of the present invention.

As generally shown in the embodiment of FIG. 2 there is provided a system for delivering a laser beam shot pattern to the lens of an eye comprising: a patient support 201; a laser 202; optics for delivering the laser beam 203; a control system for delivering the laser beam to the lens in a particular pattern 204, which control system 204 is associated with and/or interfaces with the other components of the system as represented by lines 205; a means for determining the position of lens 206 with respect to the laser, which means 206 receives an image 211 of the lens of the eye; and a laser patient interface 207.

The patient support 201 positions the patent's body 208 and head 209 to interface with the optics for delivering the laser beam 203.

In general, the laser 202 should provide a beam 210 that is of a wavelength that transmits through the cornea, aqueous and lens. The beam should be of a short pulse width, together with the energy and beam size, to produce photodisruption. Thus, as used herein, the term laser shot or shot refers to a laser beam pulse delivered to a location that results in photodisruption. As used herein, the term photodisruption essentially refers to the conversion of matter to a gas by the laser. In particular, wavelengths of about 300 nm to 2500 nm may be employed. Pulse widths from about 1 femtosecond to 100 picoseconds may be employed. Energies from about a 1 nanojoule to 1 millijoule may be employed. The pulse rate (also referred to as pulse repetition frequency (PRF) and pulses per second measured in Hertz) may be from about 1 KHz to several GHz. Generally, lower pulse rates correspond to higher pulse energy in commercial laser devices. A wide variety of laser types may be used to cause photodisruption of ocular tissues, dependent upon pulse width and energy density. Thus, examples of such lasers would include: the Delmar Photonics Inc. Trestles-20, which is a Titanium Sapphire (Ti:Sapphire) oscillator having a wavelength range of 780 to 840 nm, less than a 20 femtosecond pulse width, about 100 MHz PRF, with 2.5 nanojoules; the Clark CPA-2161, which is an amplified Ti:Sapphire having a wavelength of 775 nm, less than a 150 femtosecond pulse width, about 3 KHz PRF, with 850 microjoules; the IMRA FCPA (fiber chirped pulse amplification) µjewel D series D-400-HR, which is a Yb:fiber oscillator/amplifier having a wavelength of 1045 nm, less than a 1 picosecond pulse width, about 5 MHz PRF, with 100 nanojoules; the Lumera Staccato, which is a Nd:YVO4 having a wavelength of 1064 nm, about 10 picosecond pulse width, about 100 KHz PRF, with 100 microjoules; and, the Lumera Rapid, which is a ND:YVO4 having a wavelength of 1064 nm, about 10 picosecond pulse width, and can include one or more amplifiers to achieve approximately 2.5 to 10 watts average power at a PRF of between 25 kHz to 650 kHz and also includes a multi-pulsing capability that can gate two separate 50 MHz pulse trains. and, the IMRA FCPA (fiber chirped pulse amplification) pJewel D series D-400-NC, which is a Yb:fiber oscillator/amplifier having a wavelength of 1045 nm, less than a 100 picosecond pulse width, about 200 KHz PRF, with 4 microjoules. Thus, these and other similar lasers may be used a therapeutic lasers.

In general, the optics for delivering the laser beam 203 to the natural lens of the eye should be capable of providing a series of shots to the natural lens in a precise and predetermined pattern in the x, y and z dimension. The optics should also provide a predetermined beam spot size to cause photodisruption with the laser energy reaching the natural lens. Thus, the optics may include, without limitation: an x y scanner; a z focusing device; and, focusing optics. The focusing optics may be conventional focusing optics, and/or flat field optics and/or telecentric optics, each having corresponding computer controlled focusing, such that calibration in x, y, z dimensions is achieved. For example, an x y scanner may be a pair of closed loop galvanometers with position detector feedback. Examples of such x y scanners would be the Cambridge Technology Inc. Model 6450, the SCANLAB hurrySCAN and the AGRES Rhino Scanner. Examples of such z focusing devices would be the Phsyik International Peizo focus unit Model ESee Z focus control and the SCANLAB varrioSCAN.

In general, the control system for delivering the laser beam 204 may be any computer, controller, and/or software hardware combination that is capable of selecting and controlling x y z scanning parameters and laser firing. These components may typically be associated at least in part with circuit boards that interface to the x y scanner, the z focusing device and/or the laser. The control system may also, but does not necessarily, have the further capabilities of controlling the other components of the system as well as maintaining data, obtaining data and performing calculations. Thus, the control system may contain the programs that direct the laser through one or more laser shot patterns.

In general, the means for determining the position of the lens 206 with respect to the laser should be capable of determining the relative distance with respect to the laser and portions of the lens, which distance is maintained constant by the patient interface 207. Thus, this component will provide the ability to determine the position of the lens with respect to the scanning coordinates in all three dimensions. This may be accomplished by several methods and apparatus. For example, x y centration of the lens may be accomplished by observing the lens through a co-boresighed camera system and display or by using direct view optics and then manually positioning the patients' eye to a known center. The z position may then be determined by a range measurement device utilizing optical triangulation or laser and ccd system, such as the Micro-Epsilon opto NCDT 1401 laser sensor and/or the Aculux Laser Ranger LR2-22. The use of a 3-dimensional viewing and measurement apparatus may also be used to determine the x, y and z positions of the lens. For example, the Hawk 3 axis non-contact measurement system from Vision Engineering could be used to make these determinations. Yet a further example of an apparatus that can be used to determine the position of the lens is a 3-dimension measurement apparatus. This apparatus would comprise a camera, which can view a reference and the natural lens, and would also include a light source to illuminate the natural lens. Such light source could be a structured light source, such as for example a slit illumination designed to generate 3-dimensional information based upon geometry. Further one, two, three, four or more, light sources can be positioned around the eye and the electronically activated to provide multiple views, plainer images, of the eye, and in particular the cornea and the lens, at multiple planar slices that can them be integrated to provide data for position and location information relative to the laser system about those structures.

A further component of the system is the laser patient interface 207. This interface should provide that the x, y, z position between the natural lens and the laser remains fixed during the procedure, which includes both the measurement steps of determining the x y z position and the delivery step of delivering the laser to the lens in a shot pattern. The interface device may contain an optically transparent applanator. One example of this interface is a suction ring applanator that is fixed against the outer surface of the eye and is then positioned against the laser optical housing, thus fixing the distance between the laser, the eye and the natural lens. Reference marks for the 3-dimensional viewing and measuring apparatus may also be placed on this applanator. Moreover, the interface between the lower surface of the applanator and the cornea may be observable and such observation may function as a reference. A further example of a laser patient interface is a device having a lower ring, which has suction capability for affixing the interface to the eye. The interface further has a flat bottom, which presses against the eye flattening the eye's shape. This flat bottom is constructed of material that transmits the laser beam and also preferably, although not necessarily, transmits optical images of the eye within the visible light spectrum. The upper ring has a structure for engaging with the housing for the laser optics and/or some structure that is of known distance from the laser along the path of the laser beam and fixed with respect to the laser. Further examples of such devices are generally disclosed in U.S. Pat. No. D462442, U.S. Pat. No. D462443, and U.S. Pat. No. D459807S, the disclosures of which are hereby incorporated by reference.

It is preferred that the interface may be a corneal shaped transparent element whereby the cornea is put into direct contact with the interface or contains an interface fluid between. Examples of preferred types of patient interfaces and patient interface devices are disclosed and taught in US Patent Application Publication Nos. 2010/0022994 and in U.S. Patent Application Ser. No. 61/228,533 filed Jul. 24, 2009, Ser. No. 61/228,457 filed Jul. 24, 2009, Ser. No. 61/299,536 filed Jan. 29, 2010, and Ser. No. 61/300,167 filed Feb. 1, 2010, the entire disclosures of each of which is incorporated herein by reference.

Figure 2A:
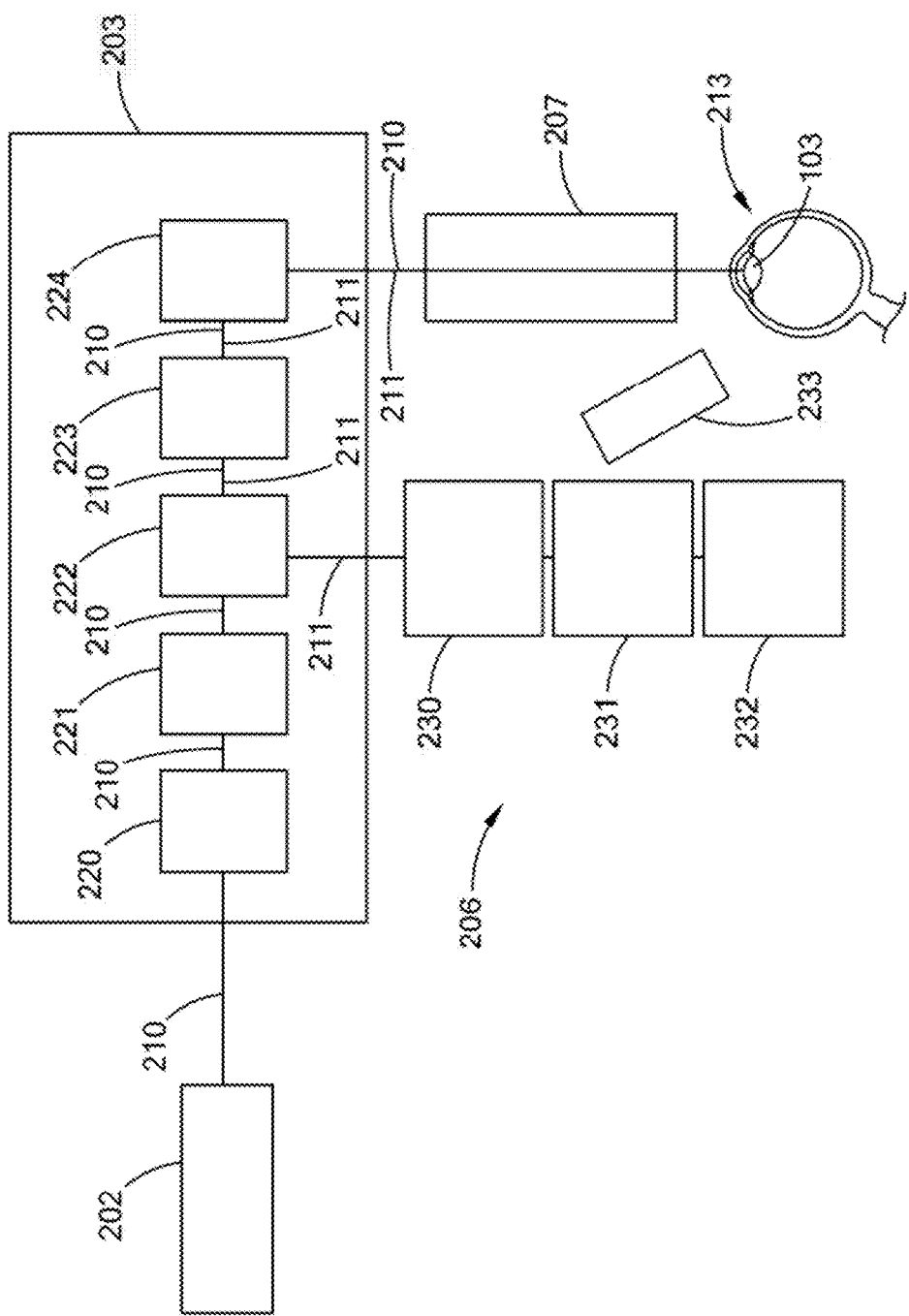
FIG. 2A is a block schematic diagram of illustrative components forming a portion of a system for delivering a laser beam shot pattern to the lens of an eye according to the teachings of the present invention.

An illustrative combination utilizing by way of example specific optics for delivering 203 the laser beam and means for determining the position of the lens 206, is shown in part, in FIG. 2A. FIG. 2A is a more detailed schematic diagram of a configuration of the system of FIG. 2. Thus, the example of FIG. 2A provides a laser 202, laser optics for delivering the laser beam 203, which optics comprise a beam expander telescope 220, a z focus mechanism 221, a beam combiner 222, an x y scanner 223, and focusing optics 224. There is further provided in FIG. 2A relay optics 230, camera optics 231, which may also include a zoom, and a ccd camera 232, which components form a part of a three-dimensional viewing and measuring apparatus. Moreover, these components 231 and 232 in combination with a light source 233, and the scanner 223 are the means for determining the position of the lens 206.

This combination of FIG. 2A utilizes the x y scanner 223 to create stereoscopic images of the lens with only a single ccd camera 232. Optical images of the eye 213 and in particular optical images of the natural lens 103 of the eye 213 are conveyed along a path 211. This path 211 follows the same path as the laser beam 210 from the natural lens 103 through the laser patient interface 207, the focusing optics 224, the x y scanner 223 and the beam combiner 222. This combination of FIG. 2A further comprises: a laser patient interface 207, and a light source 233, which could be for example uniform illumination, or a slit illumination or other structured light source designed to enhance 3-dimensional accuracy. The light source, in part, provides illumination of the natural lens of the patient's eye for the purposes of determining the 3-dimensional position of the lens. Thus, either stereoscopic images and/or the information from the camera are sent to a controller and/or computer (not shown in FIG. 2A) for further processing and use in determining 3-dimensional positions of the lens. Stereo images may be generated by commanding the scanner to go to and pause at a nominal left position and then electronically trigger the camera and controller to capture and store the left image; then command the scanner/camera/controller similarly to capture and store a right image. This sequence may be repeated in a periodic manner. These left and right images can be processed by the controller to generate the position and shape of the lens. The left and right images can be displayed using a stereo video monitor. Camera images or stereo images may also be used to measure suture geometry and orientation in the patients lens, which can be used to determine the parameters of suture based shot patterns and to align suture based shot patterns to the patients lens suture geometry and orientation. The combination illustrated in FIG. 2A provides 3-dimensional information that can be used to determine the shape of the lens, including the anterior and posterior surfaces thereof. This information can also be used to visualize the structure of the lens, including sutures. Moreover, the information about the lens obtained from the combination of FIG. 2A can further be used in determining the laser shot pattern and laser shot placement with respect to lens shape and/or structure.

FIGS. 2 and 2A-2F are block schematic diagrams and thus the relative positions and spacing of the components illustrated therein are by way of example. Accordingly, the relative placements of these components with respect to one another may be varied and all or some of their functions and components may be combined.

FIGS. 2B-2E are further more detailed embodiments of a portion of the system of FIG. 2. To the extent that like numbers are used in these Figures and in FIGS. 2 and 2A they have the same meaning. Thus, FIGS. 2B-2E provide further examples and combinations of optics for delivering the laser beam 203 and means for determining the position of the lens 206.

Figure 2B:
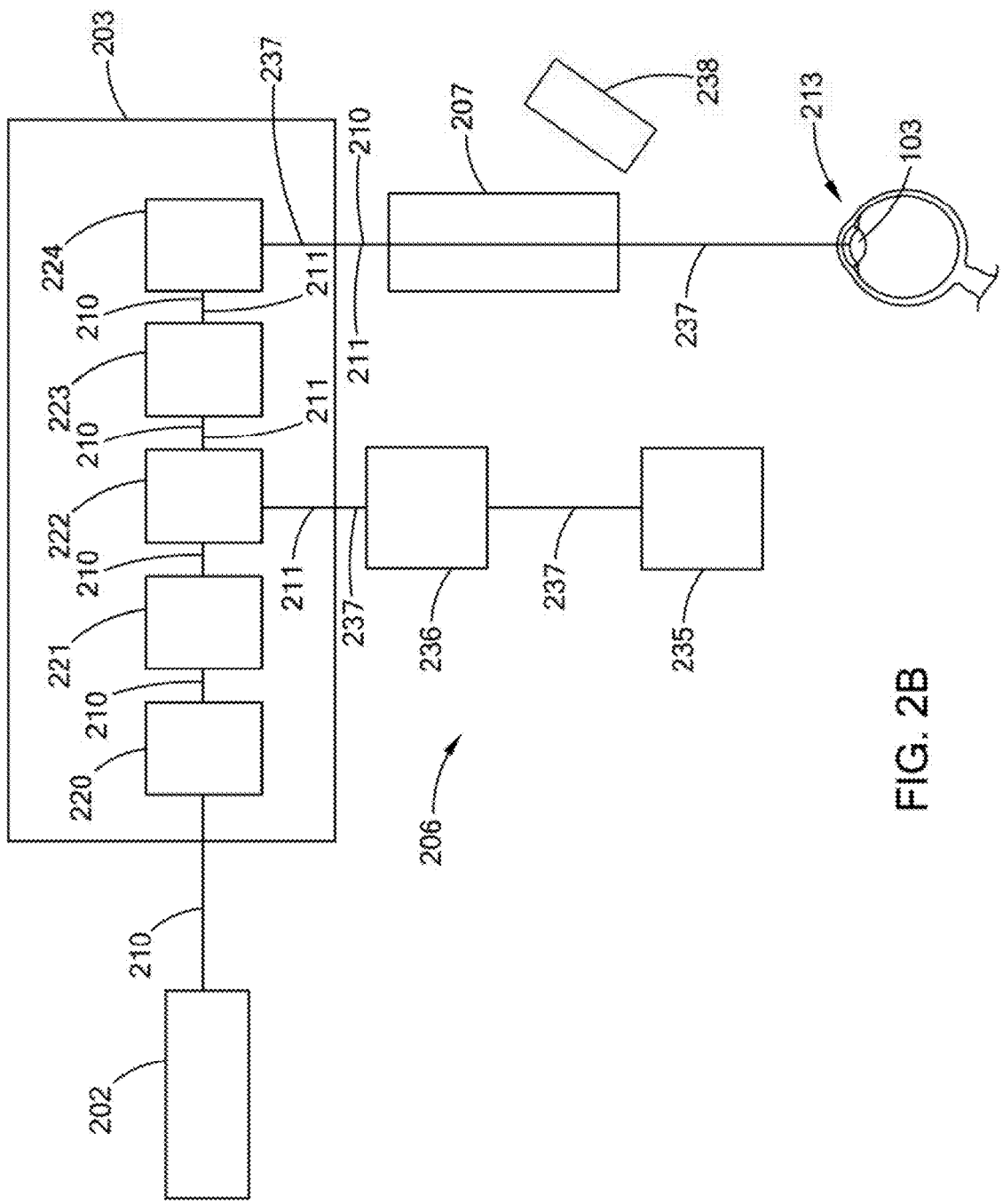
FIG. 2B is a block schematic diagram of illustrative components forming a portion of a system for delivering a laser beam shot pattern to the lens of an eye according to the teachings of the present invention.

FIG. 2B is a block schematic diagram of a portion of a system having a means for determining the position of the lens 206, which employs a scanned laser illumination source. Thus, there is provided a laser illumination source 235, a beam expander and focusing optics 236, an illumination laser path 237 and a camera 238 for viewing the lens 103 as illuminated by the laser illumination source. Component 235 in combination with the scanner 223 and camera 238 are the means for detecting the position of the lens 206.

The laser illumination source 235 can be any visible or near infrared laser diode, preferably with a short coherence length for reduced speckle. For example, the laser can be a Schafter+Kirchhoff Laser (90CM-M60-780-5-Y03-C-6) or can also be obtained from StockerYale and may also come with focusing optics. In operation, x y scanner 223 scans the beam from the illumination laser 235 into the focusing optics 224, through the patient interface 207 and onto the lens 103. Thus, the beam from the illumination laser 235 follows the illumination laser path 237. The beam expander focusing optics 236 combined with focusing optics 224 provide a high F number, slow focusing beam with long depth of field. The depth of field is approximately equal to the path length of the laser illumination beam through the lens 103. Thus, producing small and approximately equal sized spots at the anterior and posterior of lens 103. The illumination laser beam is scanned, predominately in one axis, in a line at a rate sufficiently fast compared to the camera 238 exposure time such that the scanned illumination laser beam acts like a slit illumination source during the exposure time. On subsequent exposures or frames of the camera 238, the illumination laser beam is scanned to different positions, thus, illuminating the entire lens over time. This can occur as a series of y scanned lines with different x positions exposures or the lines can be radially scanned with each exposure at a different angle. From the analysis of the data from all of these images thus obtained, the three-D position and shape of the anterior and posterior surfaces and the spatial distribution of the scattering amplitude of the lens material between those surfaces can be determined. This information may be processed by the control system and used for screening patients and implementing laser shot patterns.

Figure 2C:
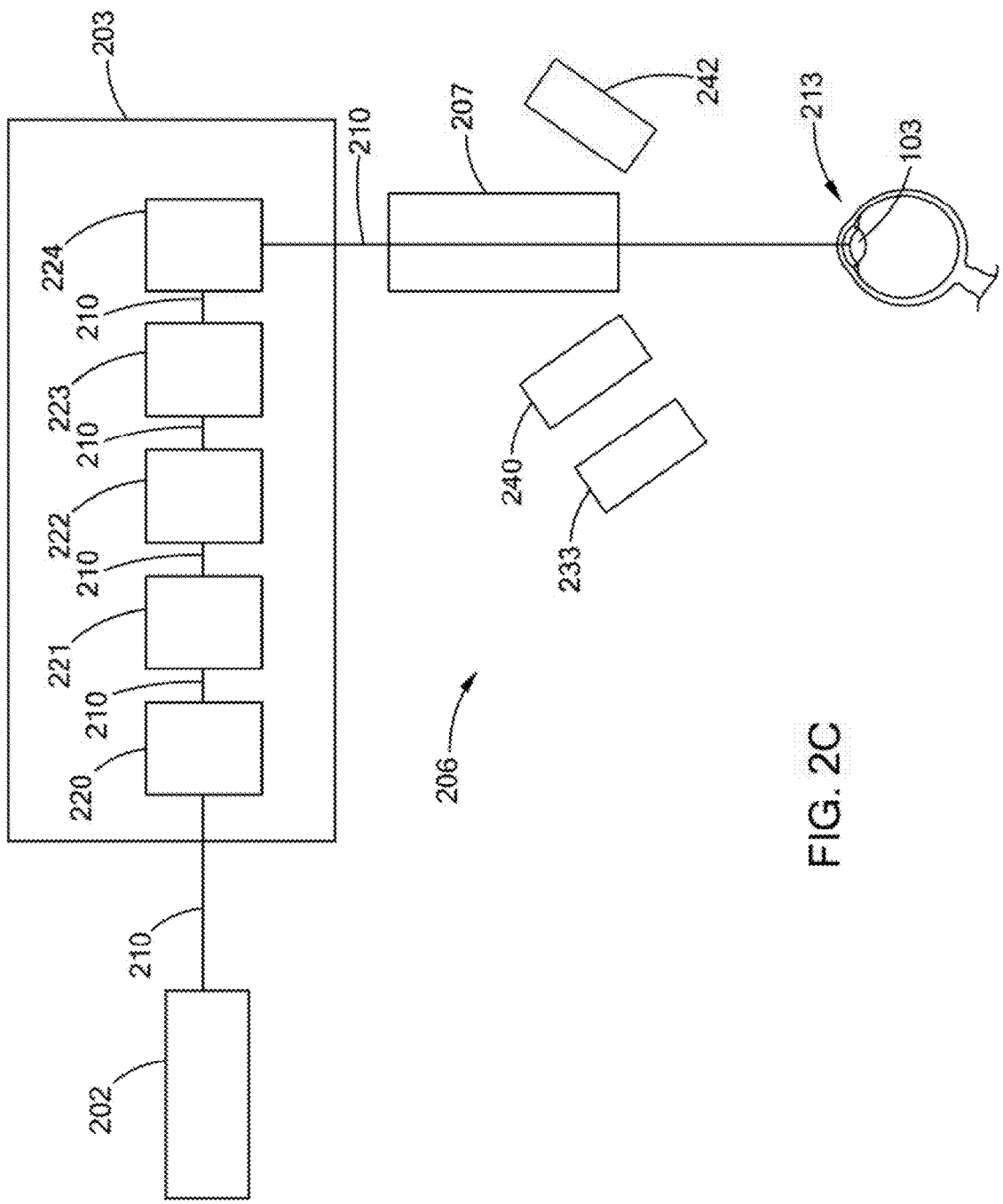
FIG. 2C is a block schematic diagram of illustrative components forming a portion of a system for delivering a laser beam shot pattern to the lens of an eye according to the teachings of the present invention.

FIG. 2C is a block schematic diagram of a portion of a system having a means for detecting the position of the lens 206, which employs dual cameras. Thus, there is provided a left camera 241 and a right camera 242. Components 241, 242 and 233 are the means for detecting the position of the lens 206.

The system of FIG. 2C utilizes two camera stereo viewing technology for providing patient care capability and for obtaining images and data for determining lens position and/or shape. Optionally, the system may feature additional cameras. These cameras may be fixed. From the analysis of the data from the images thus obtained, the three-D position and shape of the anterior and posterior surfaces and the spatial distribution of the scattering amplitude of the lens material between those surfaces can be determined. This information may be processed by the control system and used for screening patients and implementing laser shot patterns.

Figure 2D:
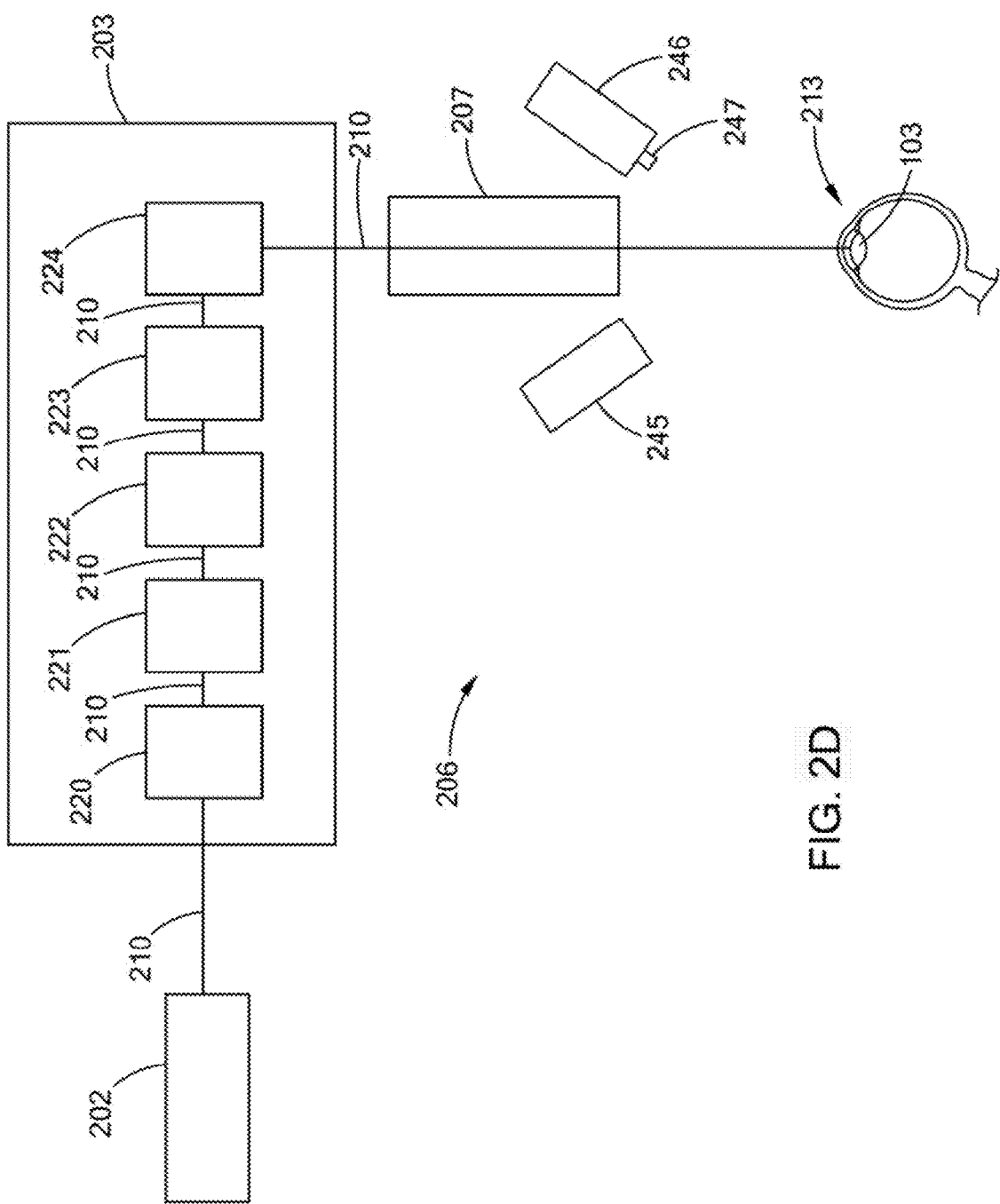
FIG. 2D is a block schematic diagram of illustrative components forming a portion of a system for delivering a laser beam shot pattern to the lens of an eye according to the teachings of the present invention.

FIG. 2D is a block schematic diagram of a portion of a system having a means for detecting the position of the lens 206, which employs structured illumination. Thus, there is provided a structured light source 245 and a camera 246, having a lens 247, for viewing the structured light source. Components 245 and 246 in combination are a means for detecting the position of the lens 206.

The system of FIG. 2D utilizes a structured light source and a camera to provide patient care capability and for obtaining images and data for determining lens position and/or shape. From the analysis of the data from the images thus obtained, the three-D position and shape of the anterior and posterior surfaces and the spatial distribution of the scattering amplitude of the lens material between those surfaces can be determined. This information may be processed by the control system and used for screening patients and implementing laser shot patterns.

Figure 2E:
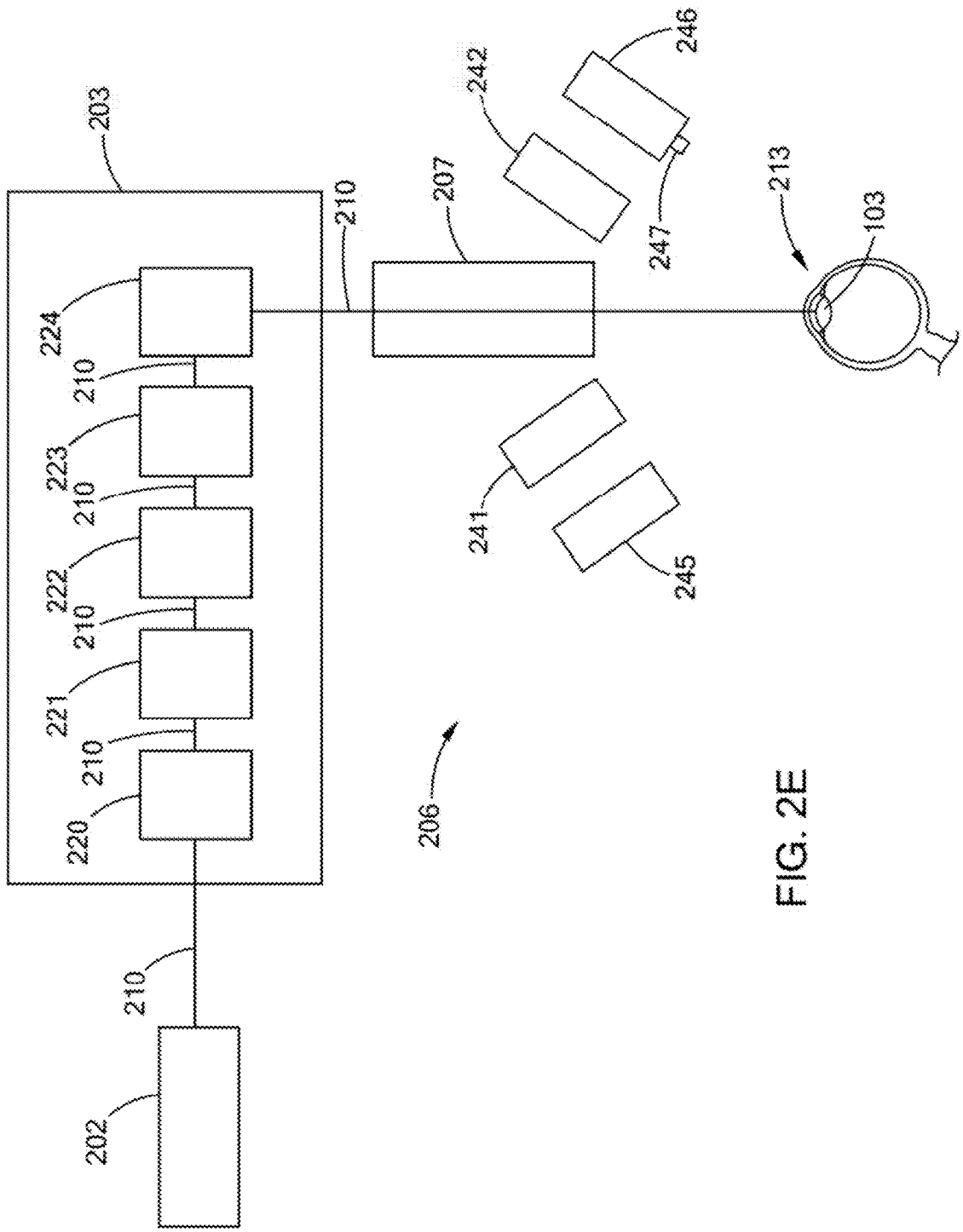
FIG. 2E is a block schematic diagram of illustrative components forming a portion of a system for delivering a laser beam shot pattern to the lens of an eye according to the teachings of the present invention.

FIG. 2E is a block schematic diagram of a portion of a system having a means for detecting the position of the lens 206, which employs structured illumination and dual cameras. Thus, there is provided a structured light source 245, a camera 246 for viewing the structured light source, a lens 247 for camera 246, a left camera 241 and a right camera 242. Components 245 and 246, in combination are the means for detecting the position of the lens 206. Components 241 and 242, in combination are a means for providing patient care, including monitoring capability. This combination 241, 242 may also provide information and/or data to determine the position of the lens.

The combination of components in the system illustrated in FIG. 2E provides the ability to optimize the accuracy of determining the position of the lens, while also providing the ability to separately and/or independently optimize patient care. Patient care includes, but is not limited to, visualization of the eye and its surrounding area, procedures such as attaching a suction ring, applying ophthalmic drops, utilizing instruments, and positioning the patient for surgery. In one embodiment the structured light source 245 may be a slit illumination having focusing and structured light projection optics, such as a Schafter+Kirchhoff Laser Macro Line Generator Model 13LTM+90CM, (Type 13LTM-250S-41+ 90CM-M60-780-5-Y03-C-6) or a StockerYale Model SNF-501-660-20-5. In this embodiment the structured illumination source 245 also includes scanning means. Another embodiment of the structured light source 245, may be a stationary grid pattern projected on the lens. From the analysis of the data from the images thus obtained, the three-D position and shape of the anterior and posterior surfaces and the spatial distribution of the scattering amplitude of the lens material between those surfaces can be determined. This information may be processed by the control system and used for screening patients and implementing laser shot patterns.

When using a scanned slit illumination the operation includes positioning the slit on one side of the lens, taking an image then moving the slit approximately one slit width, then taking another image, and then repeating this sequence until the entire lens is observed. For example, a 100 µm slit width can scan a nominal 9 mm dilated pupil diameter in 90 images, which takes approximately 3 seconds using a 30 Hz frame rate camera. To obtain images of the anterior and posterior surface in a single image without overlap, the slit should be at an angle to the AP axis, i.e., it should not be parallel to that axis. The nominal slit angle can be approximately 15 to 30 degrees from the AP axis. Any visible or near IR wavelength source within the sensitivity of the camera may be used. Low coherence length sources are preferable to reduce speckle noise.

Another embodiment for the structured light illumination sub-system shown in FIG. 2E is to arrange the structured light illumination source 245, the structured light camera 246 and the lens for the structured light camera 247 in the so-called Scheimpflug configuration which is well-known. In Summary, the Scheimpflug condition states that given an object, a lens and an image, that the object plane is imaged sharply in the image plane if the object plane, the lens plane and the image plane intersect in the same line. The structured light source 245 projects a line and or a plurality of lines onto the eye lens 103 at an angle or plurality of angles. The light scattered at the eye lens 103 forms the object to be imaged by the lens 247 and focused onto the camera system 246. Since the slit illuminated image in the eye lens 103 may be at a large angle with respect to the camera lens 247 and camera 246, this presents a large depth of field to the camera and the entire slit image may not be in sharp focus at the camera. By tilting the camera lens and the camera at an angle or plurality of angles such that Scheimpflug's condition is met, the image along the illuminated plane can be in sharp focus. Alternately, the camera and/or lens may be tilted such that the angle between the slit illuminated image plane and the camera focal plane is reduced, improving the dept-of-focus sharpness, however may not meet the Scheimpflug condition. Such configurations can improve sharpness further by reducing the aperture of the optical path, thereby increasing the F # of the system. These angles will depend on the angle the slit beam makes with the eye. This will increase the depth of field at the object, the scattered light from the slit illuminator, and allow it to imaged through the lens onto the camera image plane and remain in focus for the entire depth of the object.

There is further provided the use of a structured light illuminating and receiving system, such as for example slit illumination, which in addition to measuring the position and shape of anterior and posterior lens surfaces in three dimensions, can be used as a screening tool for determining a candidate patient's suitability for laser lens surgery. Thus, light from a structured light system is directed toward the subject lens. The amplitude of the received scattered light distributed throughout the lens is then evaluated to detect scattering regions that are above threshold, which is a level of scattering that would interfere with the laser surgery. Thus, the detection of lens scattering malformations that could interfere with, or reduce the efficacy of a procedure can be detected and evaluated. Such scattering malformations of the lens would include, without limitation, cataractous, pre-cataractous and non-cataractous tissue. Such scattering malformations, may be located throughout the lens, or may be restricted to specific regions of the lens. For example the systems of FIGS. 2A-2E in cooperation with a controller and/or processor may function as such a structured light illuminating and receiving system.

The structured light illuminating and receiving system may be contained within the surgical laser system or it may be a separate unit for evaluating the suitability of a candidate patient for laser lens surgery. Commercially available examples of such structured light illuminating and receiving systems are the Ziemer Ophthalmic Systems GALILEI Dual Scheimpflug Analyzer and the Oculus, Inc. PENTACAM. It is believed that these systems cannot be used to determine the position of the lens with respect to the treatment laser. However, lens shape data from these systems may be obtained and then used in conjunction with position data provided by systems such as the systems of FIGS. 2A-2E.

Figure 2F:
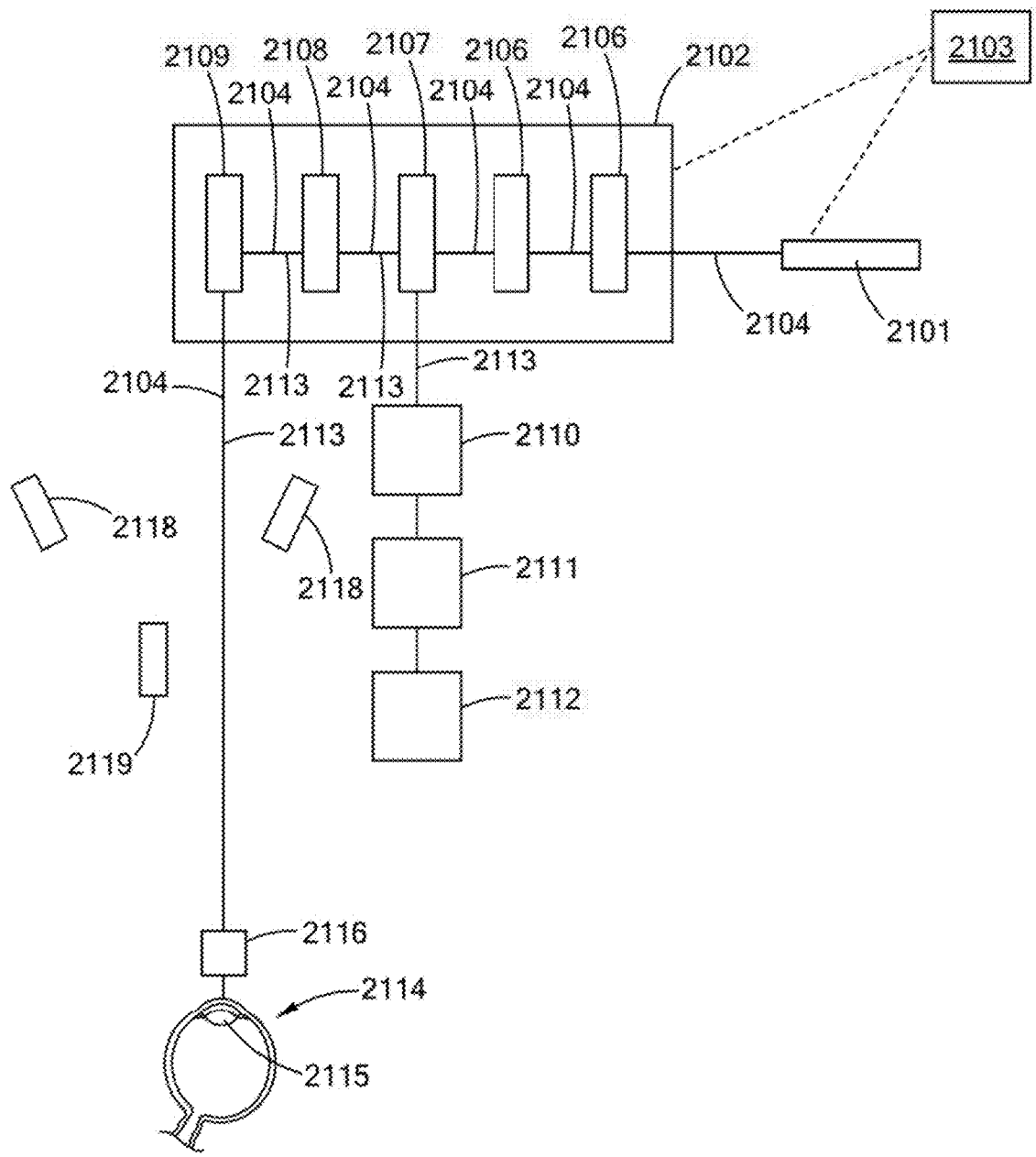
FIG. 2F is a schematic diagram of a type of system for delivering a laser beam shot pattern to the lens of an eye.

Thus, in general, a laser system, e.g., a laser device, for treating patients is provided as shown by way of example in FIG. 2F. In this system there is provided a treatment laser 2101; optics for delivering the laser beam 2102; a control system for delivering the laser beam to the lens in a particular pattern 2103, which control system 2103 is associated with and/or interfaces with the other components of the system, as shown for example by dashed lines in FIG. 2F, and/or other control systems not shown in FIG. 2F.

In general, the treatment laser 2101 should provide a beam 2104 that is of a wavelength that transmits through the cornea, aqueous and lens. The beam should be of a short pulse width, together with the energy and beam size, to produce photodisruption. Thus, as used herein, the term laser shot or shot refers to a laser beam pulse delivered to a location that results in photodisruption. As used herein, the term photodisruption essentially refers to the conversion of matter to a gas by the laser. In particular, wavelengths of about 300 nm to 2000 nm may be employed. Pulse widths from about 1 femtosecond to 100 picoseconds may be employed. Energies from about a 1 nanojoule to 1 millijoule may be employed. The pulse rate (also referred to as pulse repetition frequency (PRF) and pulses per second measured in Hertz) may be from about 1 KHz to several GHz. Generally, lower pulse rates correspond to higher pulse energy in commercial laser devices. A wide variety of laser types may be used to cause photodisruption of ocular tissues, dependent upon pulse width and energy density. Thus, examples of such lasers are disclosed in 2007/084694 A2 and WO 2007/084627A2, which are incorporated herein by reference. These and other similar lasers may be used as therapeutic lasers.

By way of example, for a given optical spot size, the amount of energy required to exceed photodisruption threshold might be 5 µJ. Rather then providing a single pulse of 20 µJ to a spot in a shot pattern, a burst of 4, 5 µJ pulses could be utilized, with each pulse in the burst being separated by about 20 nanoseconds. The use of such a burst will tend to increase the probability of achieving photodisruption threshold while also minimizing the Rayleigh range effects of extending the tissue effect in the z direction, or along the beam path. In this way the use of such bursts increase the probability of achieving photodisruption, which has also been referred to as Laser Induced Optical Breakdown (LIOB).

Accordingly, it is desirable to use energy densities in the region around LIOB threshold, i.e., the threshold at which photodisruption takes place, to minimize Rayleigh range effects. However, in the vicinity of LIOB threshold small and sometimes random variations in transmission, absorption, laser energy fluctuations, or optical spot size variations due to for example optical aberrations, can prevent LIOB in an undesirable and random matter throughout the treatment field. Optical spot size variations due to for example optical aberrations are especially found in low F/# systems.

It is further desirable in some examples to have complete treatment in any given treatment field. Thus, for example, in the shot patterns provided herein the treatment filed would be all of the x y and z coordinates of the pattern. It is further, for particular applications and in particular horizontal cuts, desirable to have laser energy densities in the vicinity of LIOB. Such energy densities minimize Rayleigh range effects and thus minimize the amount of material in the z direction that is removed. However, by using such energy densities, and thus, obtaining the benefit of minimized Rayleigh range effects, the undesirable and random prevention of LIOB, as discussed above in the preceding paragraph, can occur. Thus, to minimize Rayleigh range effect and avoid LIOB prevention, it is provided in an embodiment to use of a burst of closely spaced in time pulses, wherein each pulse within the burst is in the vicinity of LIOB threshold. Through the use of such bursts the probability of achieving LIOB threshold is increased compared to using a single pulse with the same energy density.

In general, the optics for delivering 2102 the laser beam 2104 to the natural lens of the eye should be capable of providing a series of shots to the natural lens in a precise and predetermined pattern in the x, y and z dimension. The optics should also provide a predetermined beam spot size to cause photodisruption by the laser pulses delivered to the lens or cornea.

In general, the control system 2103 for delivering the laser beam 2104 may be any computer, controller, and/or software hardware combination that is capable of selecting and controlling x y z scanning parameters and laser firing. These components may typically be associated at least in part with circuit boards that interface to the x y scanner, the z focusing device and/or the laser. The control system may also, but does not necessarily, have the further capabilities of controlling the other components of the system, as well as, maintaining data, obtaining data and performing calculations. Thus, the control system may contain the programs that direct the laser through one or more laser shot patterns. Similarly, the control system may be capable of processing data from the slit scanned laser 2117 and camera 2118 and/or from a separate controller for the slit scanned laser system or camera.

The laser optics for delivering 2102 the laser beam 2104 comprise a beam expander telescope 2105, a z focus mechanism 2106, a beam combiner 2107, an x y scanner 2108, and focusing optics 2109. There is further provided relay optics 2110, camera optics 2111, which include a zoom, and a first ccd camera 2112.

Optical images 2113 of the eye 2114 and in particular optical images of the natural lens 2115 of the eye 2114 are conveyed along a path 2113. This path 2113 follows the same path as the laser beam 2104 from the natural lens 2115 through the laser patient interface 2116, the focusing optics 2109, the x y scanner 2108 and the beam combiner 2107. There is further provided a laser patient interface 116, and a structured light source 117 and a structured light camera 118, including a lens.

A structured light source 2117 may be a slit illumination having focusing and structured light projection optics, such as a Schafter+Kirchhoff Laser Macro Line Generator Model 13LTM+9CM, (Type 13LTM-250S-41+90CM-M60-780-5-Y03-C-6) or a StockerYale Model SNF-501L-660-20-5, which is also referred to as a slit scanned laser. In this embodiment the structured illumination source 117 also includes slit scanning means 2119.

When using a scanned slit illumination the operation includes positioning the slit at an acute angle to the crystalline lens' AP axis and to one side of the lens, taking an image then maintaining the same angle, moving the slit a predetermined distance, then taking another image, and then repeating this sequence until the entire lens is observed through the series of slit sections. The nominal slit angle can be approximately 15 to 30 degrees from the AP axis. Any visible or near IR wavelength source compatible with the camera may be used. Low coherence length sources are preferable to reduce speckle noise.

The structured light illumination source 2117 and the structured light camera 2118 are arranged in an angled relationship. The angled relationship may be but is not required to be in the so-called Scheimpflug configuration, which is well-known. The structured light source 2117, in conjunction with the slit scanning means 2119, projects a line and or a plurality of lines onto the eye lens 2115 at an angle or plurality of angles. The light scattered at the eye lens 2115 forms the object to be imaged by the lens 2247 and focused onto the camera system 2118. Since the slit illuminated image in the eye lens 2115 may be at a large angle with respect to the camera 2118, this presents a large depth of field to the camera and the entire slit image may not be in sharp focus at the camera. By tilting the camera at an angle or plurality of angles the image along the illuminated plane can be in sharper focus. To the extent that a sharper focus is not obtained, arithmetic data evaluation means are further provided herein to determine a more precise location of the illuminated structures with respect to the laser device.

The images from the camera 2118 may be conveyed to the controller 2103 for processing and further use in the operation of the system. They may also be sent to a separate processor and/or controller, which in turn communicates with the controller 2103. The structured light source 2117, the camera 2118 and the slit scanning means 2119 comprise a means for determining the position, shape and apex of the lens and cornea in relation to the laser system. Alternate means of measuring the position, shape and apex of the lens and cornea may be used in lieu of the specific embodiment described herein. Other equivalent biometric methods for measuring the lens and cornea include rotating Scheimpflug configurations such are used in the commercial PENTACAM OCULUS device, optical coherence tomography (OCT) and B-scan ultrasound technologies.

In general, embodiments of the present invention provides for the delivery of the laser beam in patterns that utilize, or are based at least in part on, lens geometry, curvature of the lens and/or the position and location of the lens and cornea with respect to various apparatus. More specifically, embodiments of the invention could utilize measurements of the radii or curvature, center of curvature and apex of the lens and cornea to control the position and orientation of the capsulotomy and the position and shape of the envelope of cuts in the lens nucleus used to fragment the lens for removal. As part of embodiments of the present invention the concept of matching and/or compensating for the curvature and position of the capsule of the lens is provided. Anterior and posterior lens curvatures and lens location measurements can be used in the context of Kuszak aged lens models, Burd's eye model, Burd et al. Vision Research 42 (2002) 2235-2251, or on specific lens measurements to determine the position of the capsulotomy and shape of the envelope defining the boundary of cuts within the lens fibrous mass. Thus, in general, these laser delivery patterns are based in whole and/or in part on the mathematical modeling and actual observation data regarding the shape of the lens, the position of the lens and/or the geometry of the lens.

A further embodiment of the present systems and methods is to define a high accuracy position measurement of the anterior capsule, so as to provide in general greater accuracy, precisions and reproducibility from patient to patient for the delivery of the laser beam and beam patterns. Thus, there is provided a method applying slit technology with new and innovative methods to determine the apex of the lens of the eye, with respect to the therapeutic laser device, and thus, providing accurate measurements and relative position determinations for performing procedures on the lens of the eye.

Figure 2G:
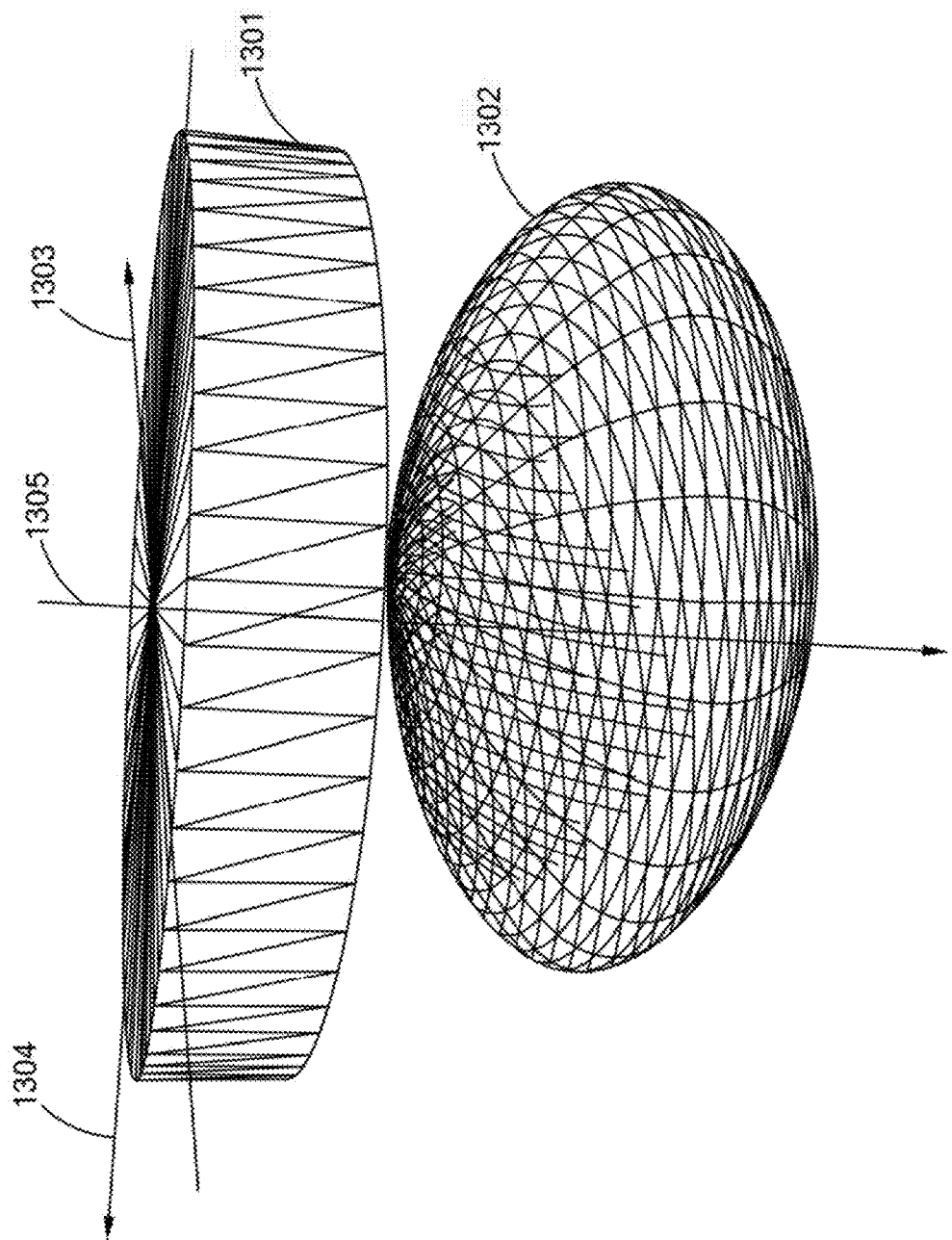
FIGS. 2G-2N are diagrams illustrating the paths of slit scanned light with respect to the lens of the eye.

Thus, turning to FIGS. 2G to 2N there is provided a series of drawings showing the use of the laser structured light source 2117 (from the embodiment of FIG. 2F) projection onto the lens of a human eye through a glass plate. FIG. 2G shows the general configuration of the glass plate and lens. FIGS. 2H to 2N show the path of the light from the slit lamp to the glass plate and the lens and the return paths of light beams from the glass plate and the lens, as the location of the slit lamp's impingement on the glass plate and the lens is changed. Like components in FIGS. 2G to 2N have like numbers, thus, for example glass plate 1301, 1401, 1501, 1601 and 1701 are the same In FIG. 2G there is provided a glass plate 1301 positioned in relation to a human lens 1302 having an X axis 1303, a Y axis 1304 and a Z axis 1305. The glass plate 1301 has a thickness of 1.57 mm and an index of refraction of 1.57.

Figure 2H:
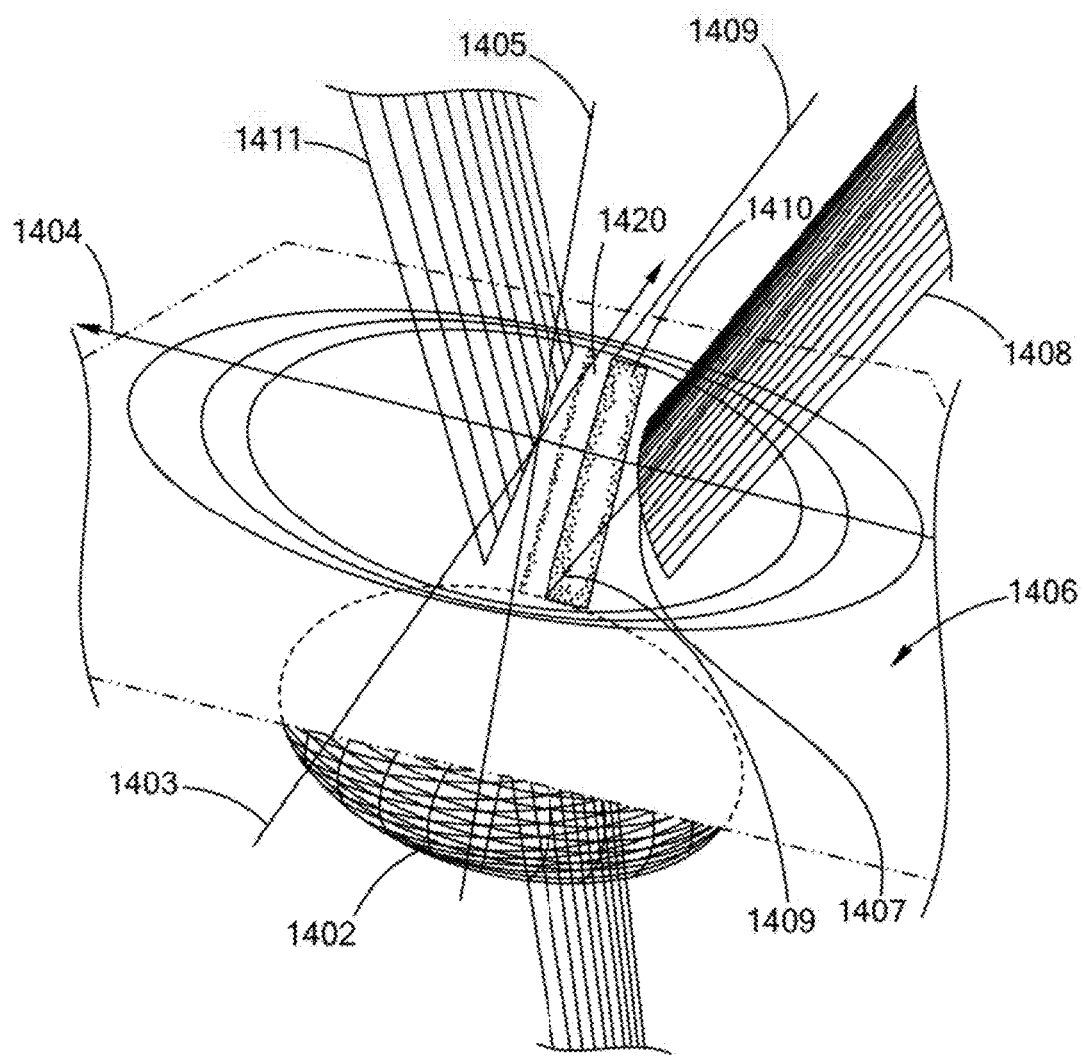
Figure 2I:
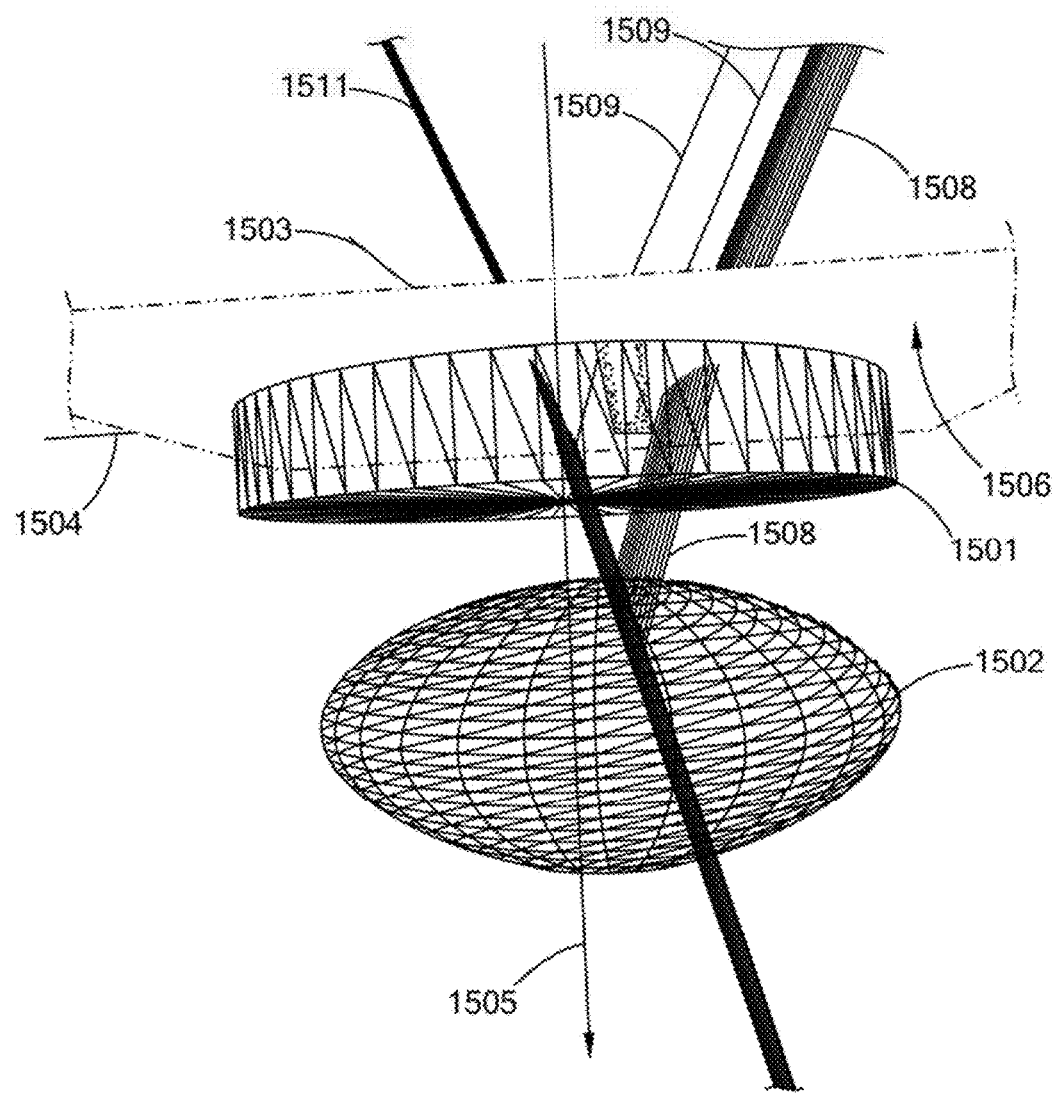

In FIG. 2H is a top view of the glass plate (not seen) and lens 1402 of FIG. 2G. In FIG. 2H there is provided an X axis 1403, a Y axis 1404, an XY plane 1406 and a Z axis 1405. In this figure light beams 1411 from a slit lamp are directed through the XY plane 1406 to the glass plate and lens 1402. The light travels back from the glass plate and lens 1402, providing an image of the glass plate 1420 and applanated cornea 1410, beams of light 1409 from the bottom of the glass plate (by bottom is it meant the side of the glass plate closest to the lens), beams of light 1408 from the anterior surface of the lens 1402, and a line 1407 based upon the beams 1408, which represents the curvature of the lens 1402 at the point where the light 1411 illuminates it. FIG. 2I is a view of the same system and light paths but from below the XY plane 1506. (Again like numbers correspond to like components, thus beam 1508 is the same as beam 1408).

Figure 2J:
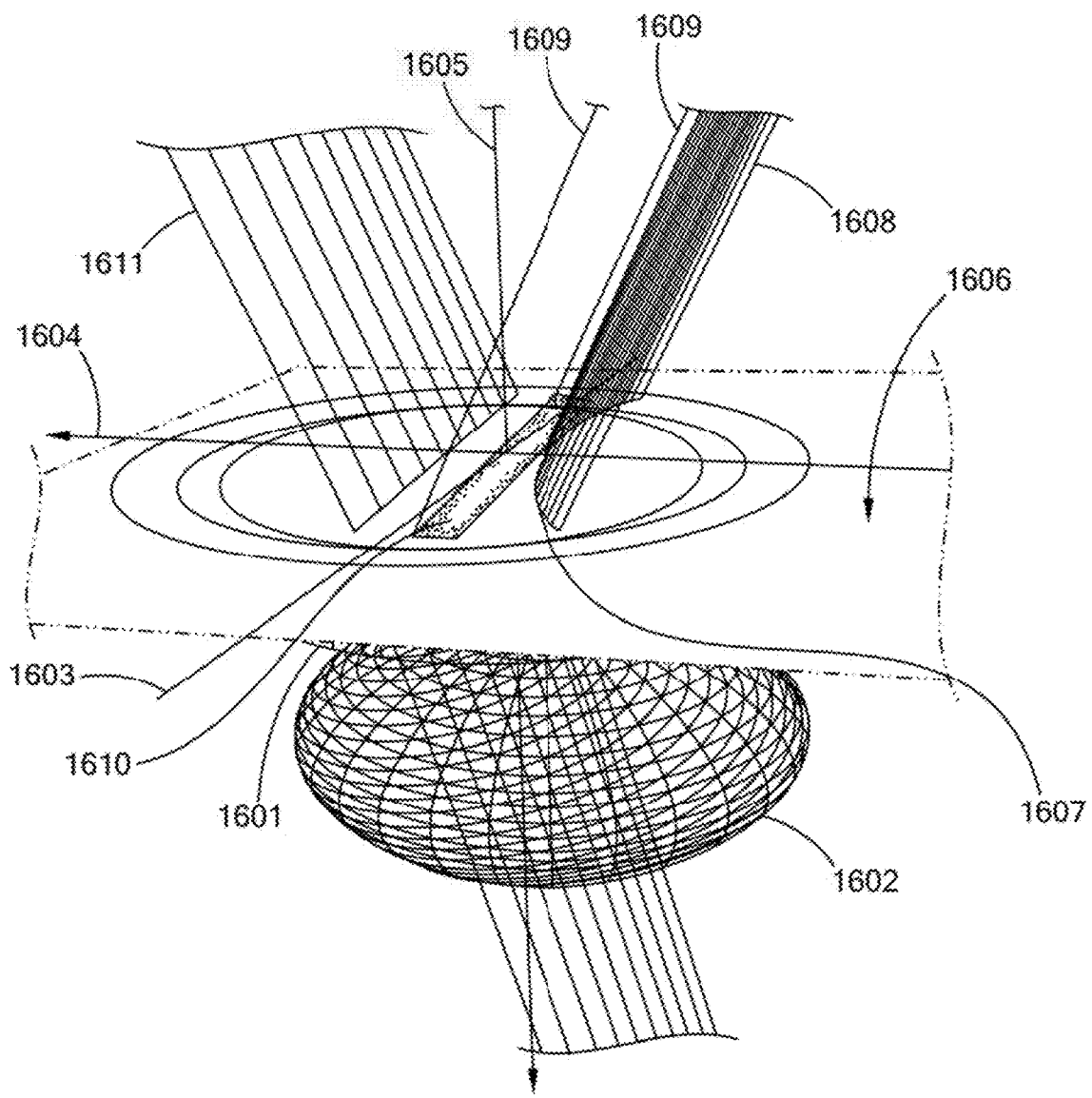

FIG. 2J is similar to FIG. 2H except that the point of illumination by the light beam 1611 on the glass 1601 and the lens 1602 has moved. Thus, by moving the point of illumination there is provided moved beams 1609 and 1608 and a curvature 1607 for a different portion of the lens.

Figure 2K:
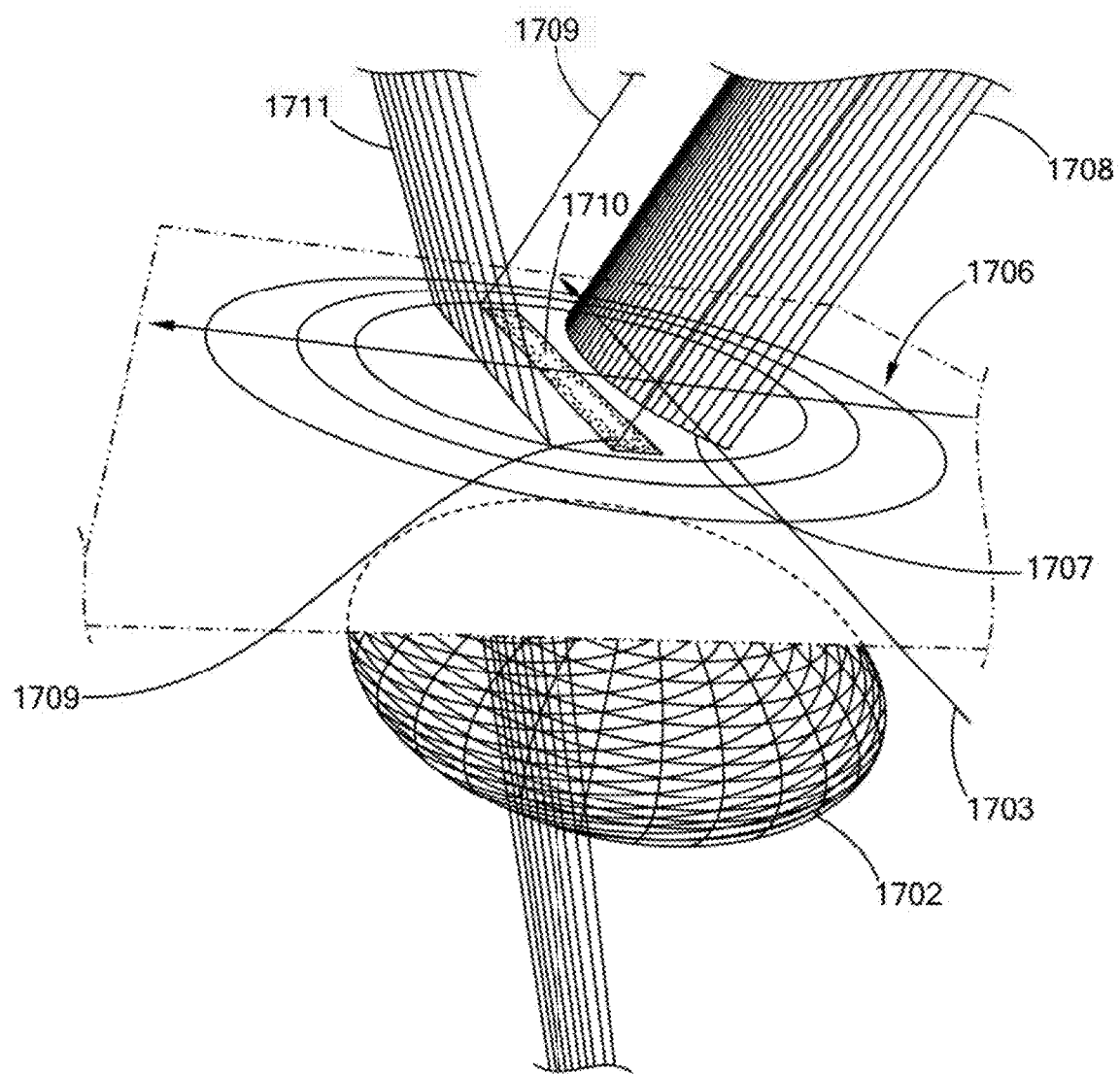

FIG. 2K is similar to FIGS. 2I and 2H, except that as with FIG. 2J the point of illumination of light beam 1711 has been moved.

Figure 2L:
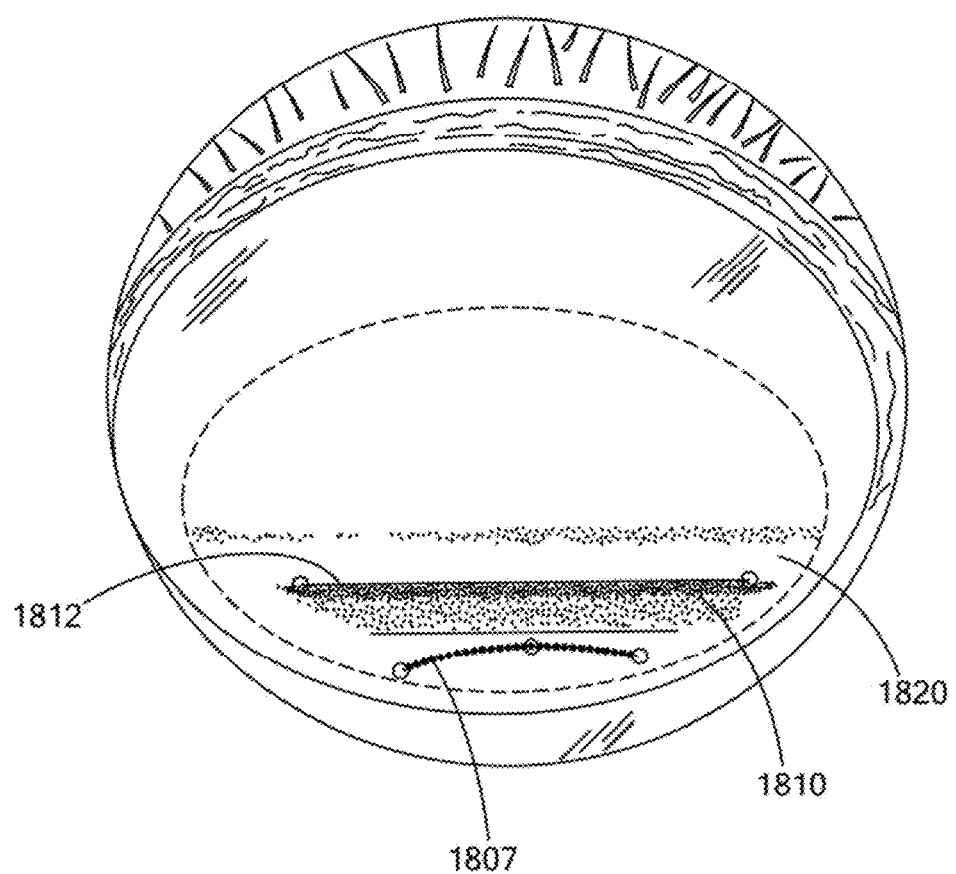

FIG. 2L is an image of the applanated cornea 1810 with the bottom surface of the glass plate 1820 being determined and labeled as line 1812. There is then provided a curvature of the lens 1807 for that particular portion of the lens that is being illuminated by the slit lamp. The determination of this curvature of the lens is based upon the application of a Random Sample Consensus ("RANSAC") algorithm to estimate with great certainty the parameters of a mathematical model from for the shape and position of the lens and in particular the lens capsule from a set of observed data, line beams such as for example 1408, 1508, 1608 & 1708. The monochrome camera images comprise an array of pixels representing light from the slit laser scattered from structures within the lens and cornea. The magnitude or brightness associated with each pixel in the image represents the amount of light scattered from a particular XYZ position within in the eye along the slit path. A highly scattering structure, such as the anterior lens capsule generates a bright arc of pixels in the image. However, viewed more closely, the image of the arc is granular and somewhat indistinct, containing some pixels which are bright and which should be definitely included in the determination of the curvature of the arc and some pixels which are of intermediate brightness which might or might not be included in the determination of the curvature. The estimation of the lens curvature involves selecting which pixels to include in the determination of curvature and then to estimate the curvature based on the selected pixels. These estimation can be done in two manners. In one manner the RANSAC algorithm is applied to all of the data obtained from the numerous camera images of slit lamp illuminations made at different slit positions and used simultaneously to determine a spherical shape. In another manner, which is presently preferred the RANSAC algorithm is applied to data from individual camera images of particular slit lamp positions and used to determine the shape and position of a circle from that each image. The circles, which were determined by RANSAC, are are used to estimate the parameters of the best fit sphere representing the lens shape, using a least squares non-liner regression. The RANSAC algorithm was first published by Fischler and Bolles in 1981.

In general the RANSAC algorithm as employed herein is based upon a number of algorithm parameters that are chosen to keep the level of probability of convergence of the fit to the circle fit parameters reasonably high. The approach is iterative wherein each iteration is used to refine the selection of which pixels (inliers) are best used to determine the parameters of the fit circle and which should be excluded (outliers) and to, at the same time refine the best fit parameters based on the pixels selected in the latest iteration. Thus, a model was fitted to the initial hypothetical inliers, to make an initial estimate of the parameters of the fit circle, i.e. shape and position of the lens from observed data. Based on the initial parameter estimates, all other data points, pixels, are checked to see how far they fall from the fitted model and the set of inliers and outliers is adjusted. The model was then re-estimated from all adjusted inliers. The model is evaluated by estimating a parameter related to the total magnitude of error of the inliers relative to the model. This procedure was repeated, and the precision of the estimate is refined at each iteration.

An example of a RANSAC algorithm is as follows:

```
input:
    data - a set of observed data points
    model - a model that can be fitted to data points
    n - the minimum number of data values required to fit the model
    k - the maximum number of iterations allowed in the algorithm
    t - a threshold value for determining when a data point fits a model
```

```
    d - the number of close data values required to assert that a model fits well to
        data
output: best_model - model parameters which best fit the data (or nil if no good model
            is found)
        best_consensus_set - data point from which this model has been estimated
        best_error - the error of this model relative to the data points
iterations := 0
best_model := nil
best_consensus_set := nil
best_error := infinity
while iterations < k
    maybe_inliers := n randomly selected values from data
    maybe_model := model parameters fitted to maybe_inliers
    consensus_set := maybe_inliers
    for every point in data not in maybe_inliers
                    if point fits maybe_model with an error smaller than t add
                        point to consensus_set
    if the number of elements in consensus_set is > d
    if the number of elements in consensus_set is > d
                    better_model := model parameters fitted to all points in
                        consensus_set
                    this_error := a measure of how well better_model fits these
                        points
                    if this_err < best_err
                        best_model := better_model
                        best_consensus_set := consensus_set
                        best_error := this_error
    increment iterations
return best_model, best_consensus_set, best_error
```

The series of best fit parameters for circles estimated for different slit beam locations is then used in a least squares algorithm to determine the radius of curvature and center of curvature of the anterior capsule, assuming that a sphere is a good representation of the shape of the capsule in the central region of interest.

Thus, by photographing the light scattered by lens structures from a laser slit beam positioned sequentially to a series of different slit locations and applying a RANSAC algorithm and/or a RANSAC algorithm and a least squares non-liner regression with a sphere fit, to the data obtained from each of those series of illuminations, a detained image of the shape and position of the lens relative to the laser device can be obtained. In the current embodiment, the shape and position of the anterior lens capsule is characterized by the estimation of the radius and center of curvature. Using this information, the position of the apex of the lens relative to the laser device, and in particular the therapeutic laser, can be determined for use in positioning and orienting the capsulotomy. Though not shown here, an exactly analogous method as described above for the anterior lens capsule can be used to determine the center and radius curvature of the anterior cornea. Since the center of curvature of the lens and cornea are known in most cases to fall close to the visual axis of the eye, these two points define a line which intersects the anterior lens capsule at or near the visual axis and position of the intersection can be used to center the capsulotomy cut at or near the visual axis as is generally desired for best optical outcome.

Having both the shape, position and apex of the lens provides the ability to greatly increase the accuracy and reproducibility of the laser shots and laser patterns placement in the lens of the eye.

In embodiments of the laser shot patterns provided herein it is preferred that the laser shot patterns generally follow the shape of the lens and placement of individual shots with respect to adjacent shots in the pattern are sufficiently close enough to each other, such that when the pattern is complete a sufficiently continuous layer and/or line and/or volume of lens material has been removed. Shot spacing of lesser or greater distances are contemplated herein and including overlap as necessary to obtain the desired results. Shot spacing considerations include gas bubble dissipation, volume removal efficiency, sequencing efficiency, scanner performance, and cleaving efficiency among others. For example, by way of illustration, for a 5 μm size spot with an energy sufficient to cause photodisruption, a spacing of 20 μm or greater results in individual gas bubbles, which are not coalesced and dissipate more quickly, than with close shot spaces with the same energy, which result in gas bubble coalescence. As the shot spacing gets closer together volume efficiency increases. As shot spacing gets closer together bubble coalescence also increases. Further, there comes a point where the shot spacing becomes so close that volume efficiency dramatically decreases. For example, by way of illustration, for a 450 femtosecond pulse width and 2 microjoules energy and about a 5 μm spot size with a 10 μm separation results in cleaving of transparent ocular tissue. As used herein, the term cleaving means to substantially separate the tissue. Moreover, the forgoing shot spacing considerations are interrelated to a lesser or greater extent and one of skill in the art will know how to evaluate these conditions based upon the teachings of the present disclosure to accomplish the objectives herein. Finally, it is contemplated that the placement of individual shots with respect to adjacent shots in the pattern may in general be such that they are as close as possible, typically limited by the size and time frame of photodisruption physics, which would include among other things gas bubble expansion of the previous shot. As used herein, the time frame of photodisruptive physics referrers to the effects that take place surrounding photodisruption, such as plasma formation and expansion, shock wave propagation, and gas bubble expansion and contraction. Thus, the timing of sequential pulses such that they are timed faster than some of, elements of, or all of those effects, can increase volumetric removal and/or cleaving efficiency. Accordingly, we propose using pulse repetition frequencies from 5 KHz to 1 MHz., which could be accomplished by a laser with the following parameters: a mode lock laser of cavity length from 3 meters to 3 cm. Such high PRF lasers can more easily produce multiple pulses overlapping a location allowing for a lower energy per pulse to achieve photodisruption.

Figure 2M:
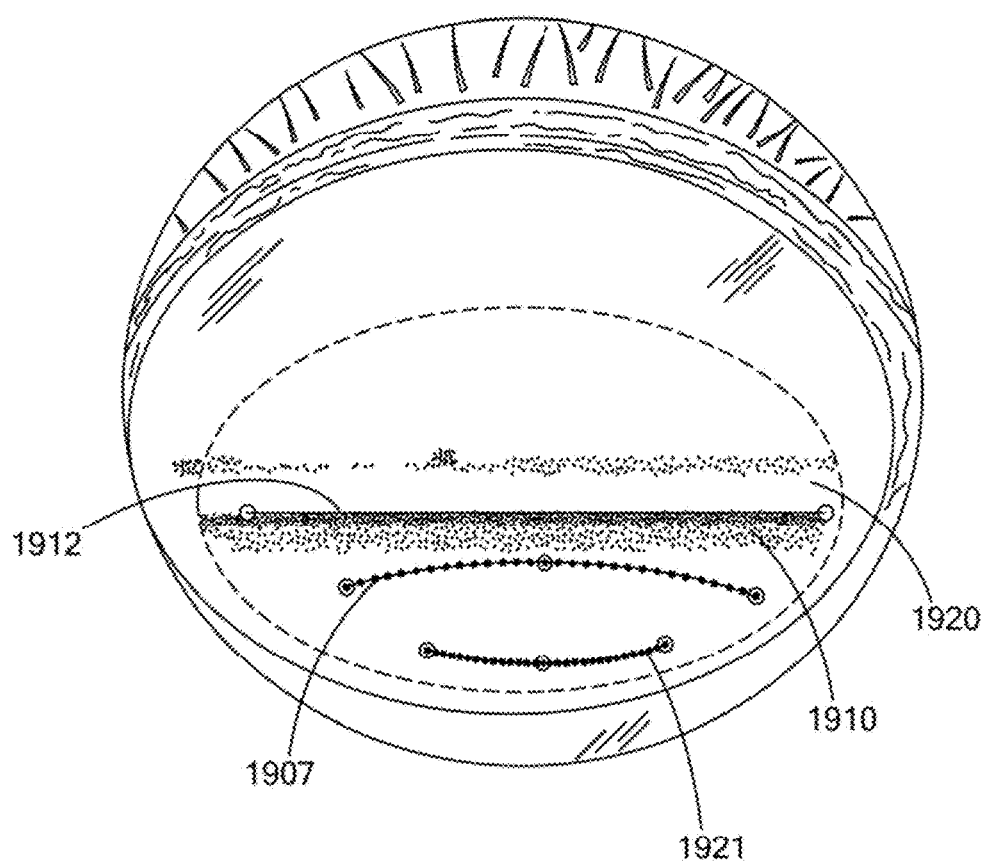

In FIG. 2M there is provided an image of a reference glass plate 1920, the posterior surface 1912 of the reference glass plate 1920 and the applanated cornea 1910. There is further provided the lens anterior capsule 1907 and the lens posterior capsule 1921.

Figure 2N:
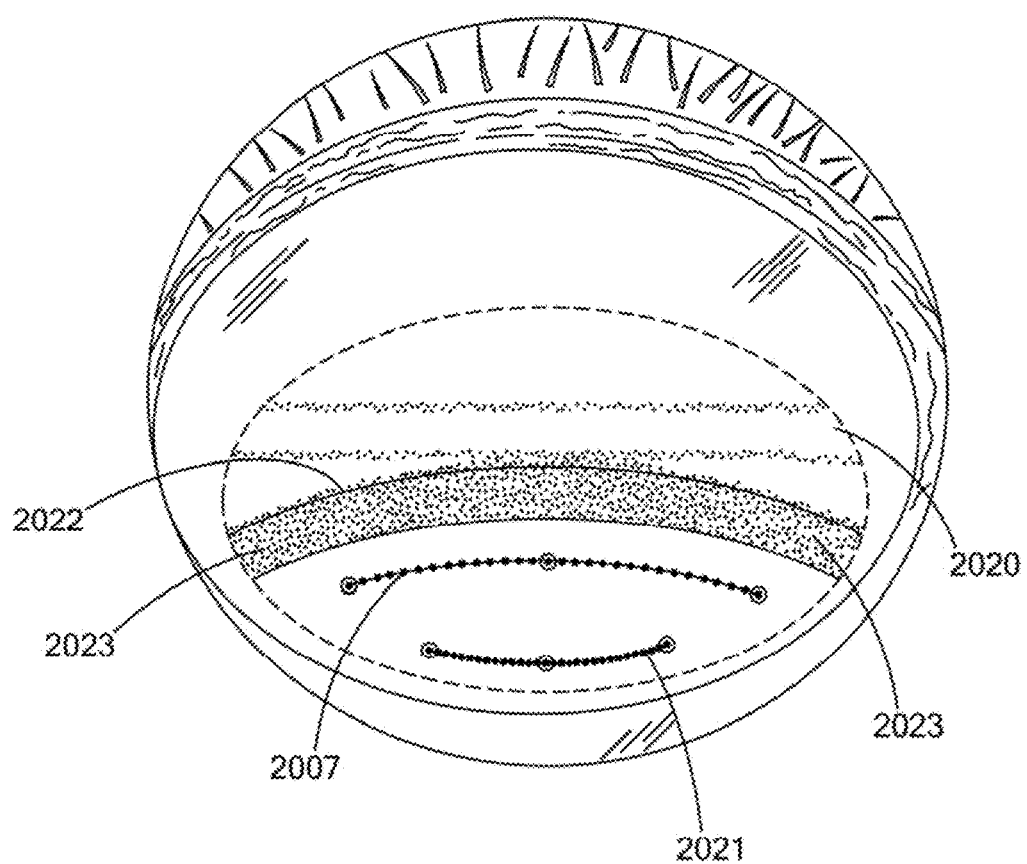

In FIG. 2N there is provided an image of a curved corneal interface 2022 and the un-applinated cornea 2023, as well as a reference glass 2020. There is further provided the lens anterior surface 2007 and the lens posterior surface 2021.

Thus, as show in FIGS. 2M and 2N, by way of example, embodiments of the present invention provides a novel means for determining the lens anterior and posterior capsule radii and centers of curvature.

In general, embodiments of the present invention provides for the delivery of the laser beam in patterns that utilize, or are based at least in part on, the lens suture geometry and/or the curvature of the lens and/or the various layers within the nucleus; and/or the curvatures of the various layers within the nucleus; and/or the suture geometry of the various layers within the nucleus. As part of embodiments of the present invention the concept of matching the curvature of the anterior ablations to the specific curvature of the anterior capsule, while having a different curvature for posterior ablations, which in turn match the posterior curvature of the lens is provided. Anterior and posterior curvatures can be based on Kuszak aged lens models, Burd's numeric modeling, Burd et al. Vision Research 42 (2002) 2235-2251, or on specific lens measurements, such as those that can be obtained from the means for determining the position of the lens with respect to the laser. Thus, in general, these laser delivery patterns are based in whole and/or in part on the mathematical modeling and actual observation data regarding the shape of the lens, the shape of the layers of the lens, the suture pattern, and the position of the sutures and/or the geometry of the sutures.

Moreover, as set forth in greater detail, it is not necessary that the natural suture lines of the lens or the natural placement of the layers of the lens be exactly replicated in the lens by the laser shot pattern. In fact, exact replication of these natural structures by a laser shot pattern, while within the scope of the invention, is not required, and preferably is not necessary to achieve an increase in accommodative amplitude. Instead, embodiments of the present invention, in part, seeks to generally emulate the natural lens geometry, structures and positioning and/or portions thereof, as well as build upon, modify and reposition such naturally occurring parameters through the use of the laser shot patterns described herein.

In embodiments of the laser shot patterns provided herein it is generally preferred that the laser shot patterns generally follow the shape of the lens and placement of individual shots with respect to adjacent shots in the pattern are sufficiently close enough to each other, such that when the pattern is complete a sufficiently continuous layer and/or line and/or volume of lens material has been removed; resulting in a structural change affecting accommodative amplitude and/or refractive error. Shot spacing of lesser or greater distances are contemplated herein and including overlap as necessary to obtain the desired results. Shot spacing considerations include gas bubble dissipation, volume removal efficiency, sequencing efficiency, scanner performance, and cleaving efficiency among others. For example, by way of illustration, for a 5 µm size spot with an energy sufficient to cause photodisruption, a spacing of 20 µm or greater results in individual gas bubbles, which are not coalesced and dissipate more quickly, than with close shot spaces with the same energy, which result in gas bubble coalescence. As the shot spacing gets closer together volume efficiency increases. As shot spacing gets closer together bubble coalescence also increases. Further, there comes a point where the shot spacing becomes so close that volume efficiency dramatically decreases. For example, by way of illustration, for a 450 femtosecond pulse width and 2 microjoules energy and about a 5 µm spot size with a 10 µm separation results in cleaving of transparent ocular tissue. As used herein, the term cleaving means to substantially separate the tissue. Moreover, the forgoing shot spacing considerations are interrelated to a lesser or greater extent and one of skill in the art will know how to evaluate these conditions based upon the teachings of the present disclosure to accomplish the objectives herein. Finally, it is contemplated that the placement of individual shots with respect to adjacent shots in the pattern may in general be such that they are as close as possible, typically limited by the size and time frame of photodisruption physics, which would include among other things gas bubble expansion of the previous shot. As used herein, the time frame of photodisruptive physics referrers to the effects that take place surrounding photodisruption, such as plasma formation and expansion, shock waive propagation, and gas bubble expansion and contraction. Thus, the timing of sequential pulses such that they are timed faster than some of, elements of, or all of those effects, can increase volumetric removal and/or cleaving efficiency. Accordingly, we propose using pulse repetition frequencies from 50 MHz to 5 GHz., which could be accomplished by a laser with the following parameters: a mode lock laser of cavity length from 3 meters to 3 cm. Such high PRF lasers can more easily produce multiple pulses overlapping a location allowing for a lower energy per pulse to achieve photodisruption.

The terms first, second, third, etc. as used herein are relative terms and must be viewed in the context in which they are used. They do not relate to timing, unless specifically referred to as such. Thus, a first cut may be made after a second cut. In general, it is preferred to fire laser shots in general from posterior points in the laser pattern to anterior points, to avoid and/or minimize the effect of the gas bubbles resulting from prior laser shots. However, because of the varied laser shot patterns that are provided herein, it is not a requirement that a strict posterior to anterior shot sequence be followed. Moreover, in the case of cataracts it may be advantageous to shoot from anterior to posterior, because of the inability of the laser to penetrate substantially beyond the cataract.

Sectional patterns may be employed. Such patterns would include the cube patterns, variations in the shape and size of this cube pattern, concentric cylinders, radial planes, horizontal planes and vertical planes, partial shells and shells, and combinations thereof. As used to describe these patterns, vertical refers to essentially parallel to the optical axis, i.e., the AP axis. These sectional patterns are employed within, or to comprise, a particular shaped volume. Thus, these sectional patterns can be used in shaped volumes that provide for positive or negative refractive corrections. Further, these shaped patterns can be used in shaped volumes that result in shaped structural weakening, which causes shape change and results in a positive or negative refractive correction. Additionally, shaped structural weakening may also result in increased accommodative amplitude.

Moreover, these patterns can be employed in conjunction with each other, i.e., vertical and horizontal, or in isolation, i.e., only vertical or horizontal, at various locations in the lens, which locations can range from totally separate, to slightly overlapping, to overlapping. Additionally, by selectively arranging placement and density of these patterns and/or combination of primarily vertical and primarily horizontal patterns, local structure in the lens can be weakened by varying and predetermined amounts, which can result in selective flexibility and shape changes. Thus, through such selective placement and density determinations shaped structural weakening may be accomplished.

The system is capable of making radial cuts in the cornea that are more-centrally located and would give the surgeon the ability to perform less than 1.5-2D spherical adjustments with our without arcuate incisions either during cataract surgery or as a separate, post-cataract surgery, enhancing procedure. The system preferably would make small cuts 1 to 2 mm in length. The small incisions may be in our outside the optically-active area. The incisions function to change the shape of the cornea. Preferably, these can be done after a cataract surgery to address or fine tune refractive issues.

This functionality also allows the system to form incisions that allow for the insertion of intrastromal corneal ring segments into the deep cornea stroma to improve vision for myopic patients as well as to treat keratoconus.

In instances when corneal incisions are made to insert tools preferably to remove the lens for the insertion of an IOL, the system allows for the cutting pattern to extend up to, but not break the surface of the cornea. The system thus allows for the insertion of air into the cut, once the patient is in a sterile environment. The air will then allow for the opening of the incision and break the surface of the cornea in a controlled area. This prevents the need for the laser to break the surface of the cornea.

Laser shot patterns can be based upon measured lens data and lens data that is obtained by using Burd modeling, which model is set forth in Burd et al., Numerical modeling of the accommodating lens, Visions Research 42 (2002) 2235-2251. The Burd model provides the following algorithm for anterior and/or posterior shape: □

$$Z = aR^5 + bR^4 + cR^3 + dR^2 + f$$

The coefficients for this algorithm are set forth in Table I.

TABLE I

|  | a | b | c | d | f |
|---|---|---|---|---|---|
| Anterior (11-year) | −0.00048433393427 | 0.00528772036011 | −0.01383693844808 | −0.07352941176471 | 2.18 |
| Posterior (11-year) | 0.00300182571400 | −0.02576464843559 | 0.06916082660799 | 0.08928571428571 | −2.13 |
| Anterior (29-year) | 0.00153004454939 | 0.01191111565048 | −0.02032562095557 | −0.07692307692308 | 2.04 |
| Posterior (29-year) | 0.00375558685672 | −0.03036516318799 | 0.06955483582257 | 0.09433962264151 | −2.09 |
| Anterior (45-year) | −0.00026524088453 | 0.00449862869630 | −0.01657250977510 | −0.06578947368421 | 2.42 |
| Posterior (45-year) | 0.00266482873720 | −0.002666992717562 | 0.08467905191557 | 0.06172839506173 | −2.42 |

These cuts are preferably intrastromal. They are may be one, two, three, four, or more incision. Preferably, evenly radially spaced from less than 1 mm to about 1-2 mm, although greater or small distances may be utilized.

In some embodiments, arcuate channels may be placed in the stroma or the cornea. These arcuate channels can be preferably be between 50-300 microns, or more preferably, about 200 microns below the cornea. The channels ban be used to hold intrastromal corneal rings, as well as other ring-like structures known today or later developed.

The system also has the functionality to form incisions in a fully or partially applanated eye that avoids sharp angles during a corneal incision. The system can do so because it has the radiusing the angle of the incision. This softens the angle of the incision. By radiusing the angle, there is less-likelihood of the insertion of a corneal inlay tearing the tissue or requiring the use of greater force. The system further allows for determining a pattern for cutting an arcuate channel or a pocket in a flat, fully-applanated cornea, that provides for specific, predetermined, and uniform placement of a pocket in the tissue, in particular with respect from the distance of the surface of the cornea upon the eye returning to its natural shape after applanation. Thus, the system provides the ability to have custom pockets and channels that follow the curvature of the exterior surface of the cornea, the curvature of the interior surface of the cornea, or other predetermined shapes or cuts. These pockets and channels allow for the insertion of inlays and intrastromal rings with minimal trauma.

Figure 3:
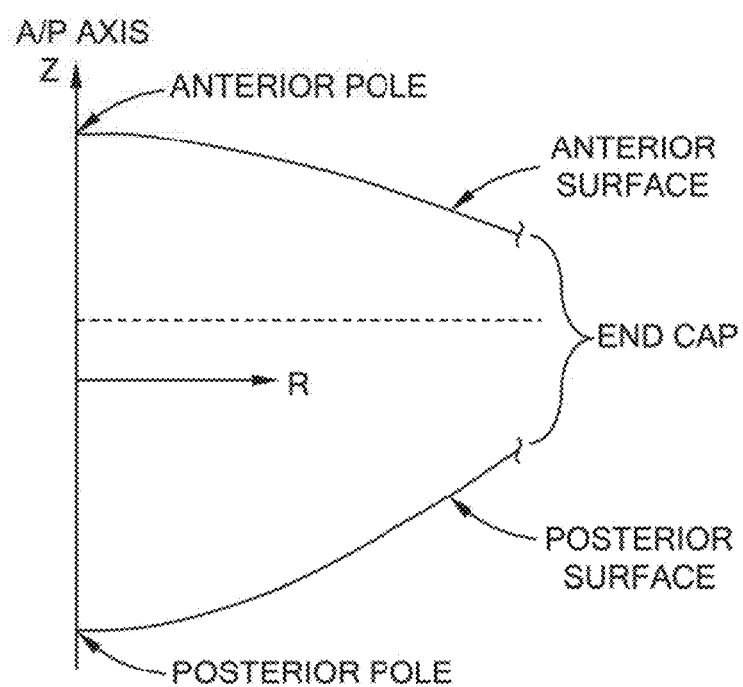
FIG. 3 is a cross-section drawing of the lens relating to the model developed by Burd.
Figures 4A, 4B:
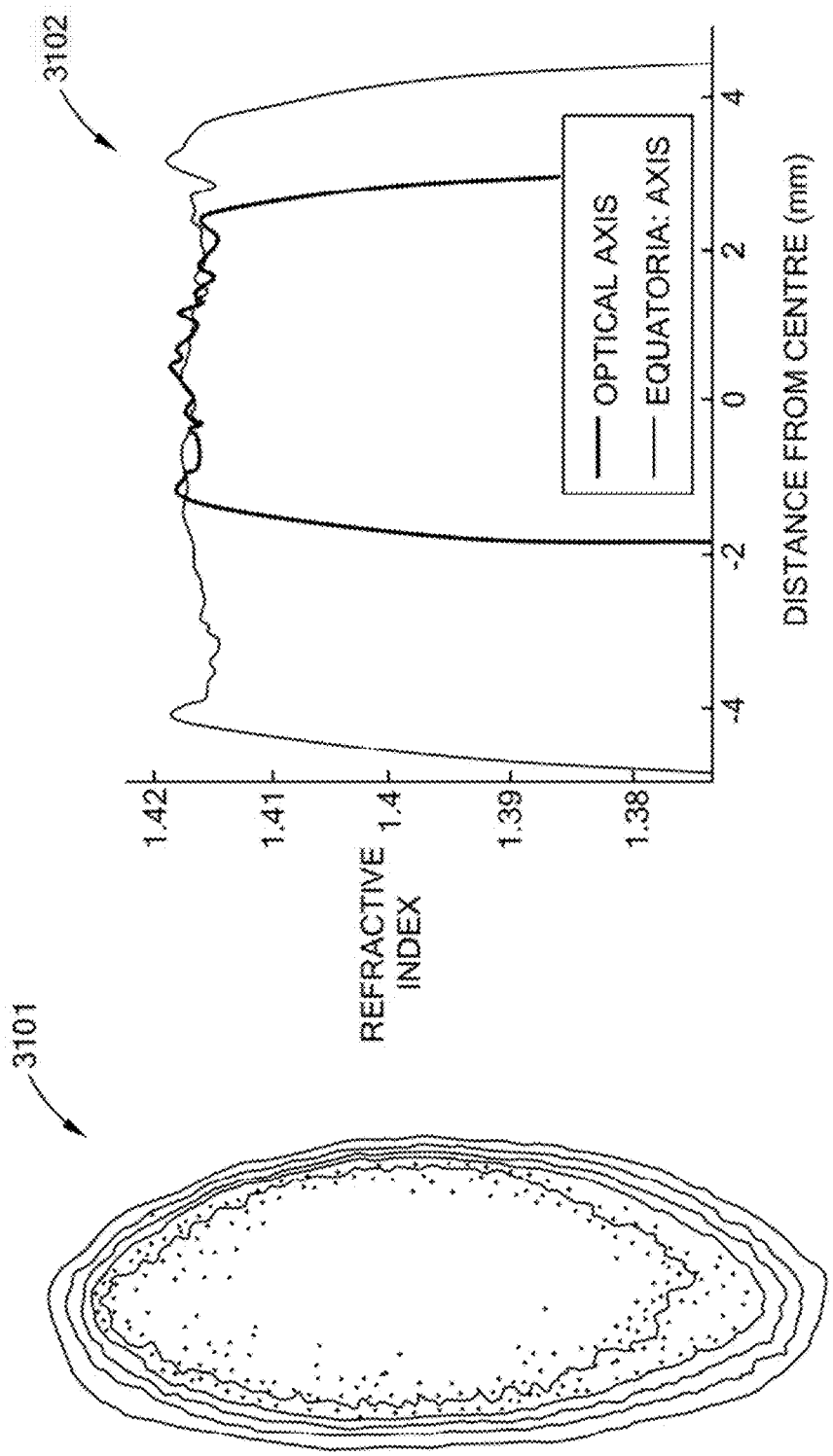
FIGS. 4 A-D are diagrams illustrating youthful vs old age gradient index behavior.
Figures 4C, 4D:
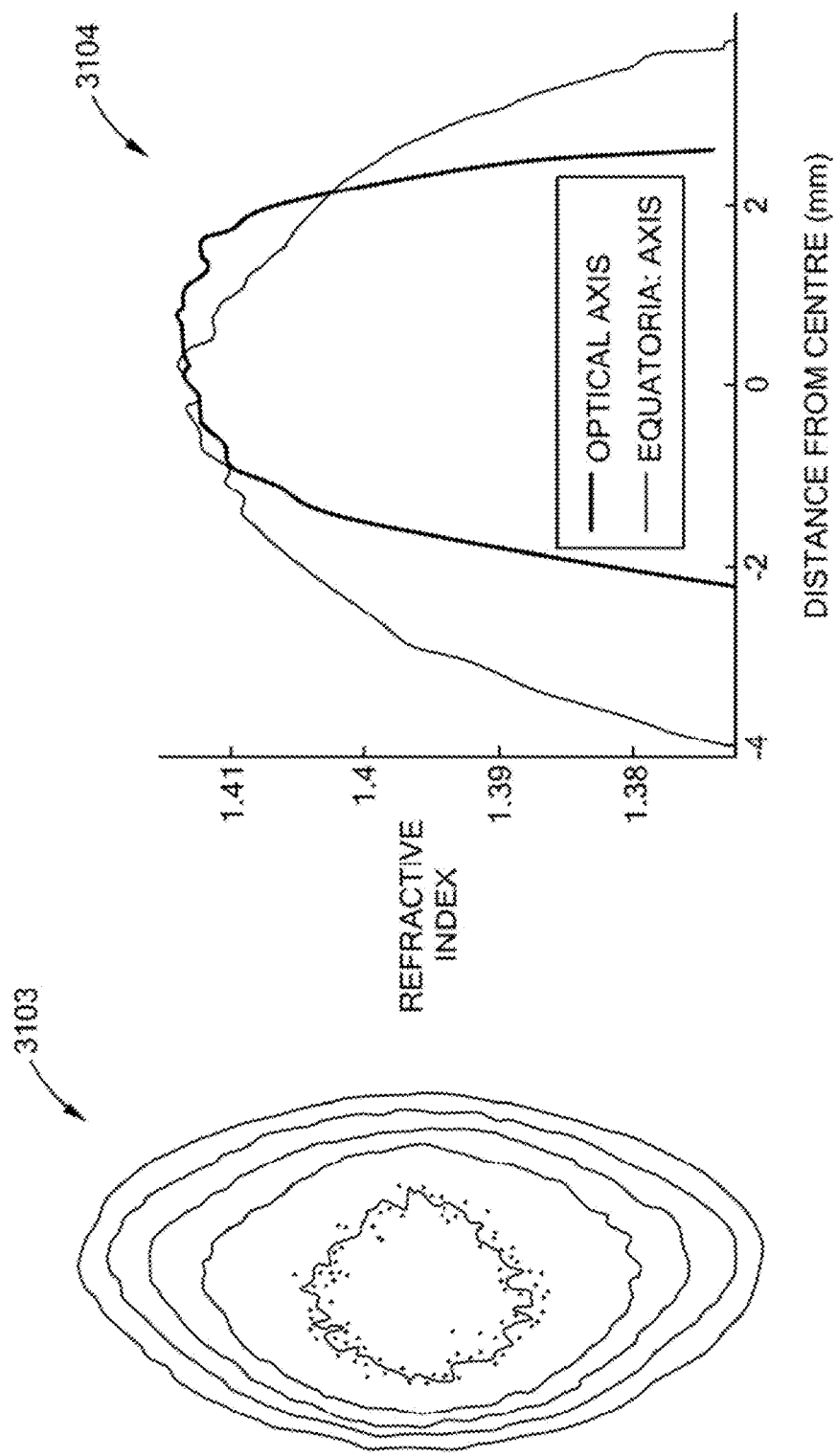

Additionally, the variables Z and R are defined by the drawing FIG. 3.

An embodiment of system and method relates to gradient index modification of the lens. Moffat, Atchison and Pope, Vision Research 42 (2002) 1683-1693, showed that the natural crystalline lens contains a gradient index of refraction behavior that follows the lens shells structure and dramatically contributes to overall lens power. They also showed that this gradient substantially diminishes, or flattens as the lens ages reducing the optical power of the lens. The loss of gradient index with age most likely explains the so-called Lens Paradox, which presents the conundrum that the ageing lens is known to grow to a steeper curvature shape that should result in higher power, yet the aging lens has similar power to the youthful lens. Essentially it is postulated that the increase in power due to shape changes is offset by the power loss from gradient index loss. Examples of the youthful vs old age gradient index behavior is shown in FIGS. 4A-D, which provides data taken from the more recent work from the same group Jones, Atchison, Meder and Pope, Vision Research 45 (2005) 2352-236. We can see from these figures that the old lens 3101 has a flat index behavior radially 3102 and the young lens 3103 has continuously diminishing index radially 3104 from approximately 1.42 in the center to 1.38 nearer the outer shells of the lens. Thus, based upon this data it is provided to use the photodissruptive laser in the creation of small voids within the lens fiber material which will then fill-in with aqueous humor fluid which has a lower index of refraction and, via area weighting or volume weighting, decrease the net refractive index of a particular region. Accordingly, if different void densities are placed in nested shell volumes, then this would diminish the average index of refraction of essentially concentric regions in a similar manner to the youthful lens.

Figure 5:
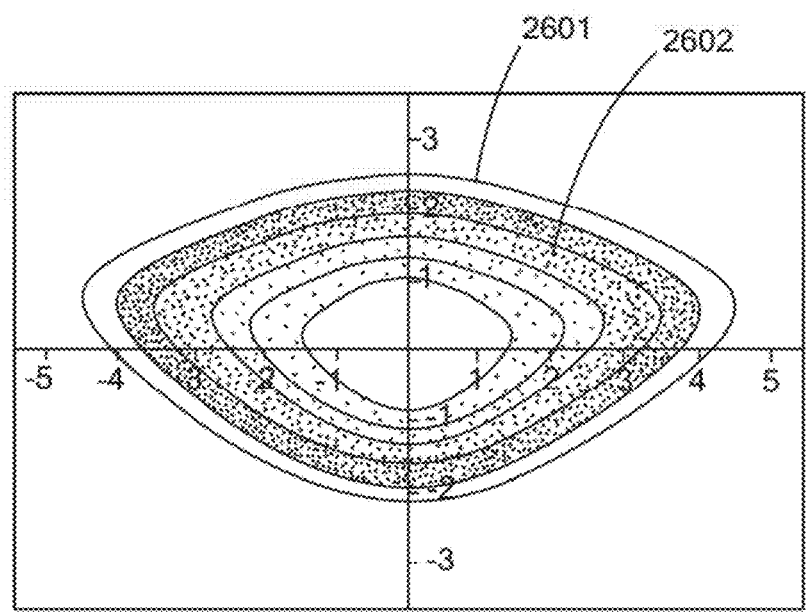
FIG. 5 is a cross-section drawings of a lens showing the placement of a gradient index modification laser shot patterns in accordance with the teachings of the present invention.

An embodiment of the system and methods provides a gradient index modification, which has different void densities placed in nested volumes, as shown in FIG. 5. Thus, there is provided a series of nested shot patterns 2602 and a lens outer surface 2601, with each pattern creating an incrementally different void density in the lens material. For example, if a nominal 25% weighting efficiency was obtained in the most densely treated region, filling that volume with 1.38 index of aqueous humor, and the remaining region that was 75% lens material of index 1.42, then the average resultant index of refraction would be 0.25*1.38+0.75*1.42 or 1.41, which we see from FIGS. 4A-D, that would restore the gradient from the center to a 2 mm radius, which is most central optical region for visual function. Thus, FIG. 5 shows a distributed regional treatment of increasing density from the center of the lens to the periphery of the lens.

In an embodiment of the laser system there is an ophthalmic surgical laser for use in patients undergoing cataract surgery for removal of the crystalline lens, which uses would include among other things, anterior capsulotomy, laser phacofragmentation, and the creation of full and partial thickness single-plane and multi-plane arc cuts/incisions in the cornea, each of which may be performed either individually or consecutively during the same procedure. In an embodiment of the system a a mode-locked Yb:YAG laser that generates a series of low energy pulses at a wavelength in the IR range. Preferably the pulse frequency is in the pico- and femto-second ranges, from for example about $0.35 \times 10^{-12}$ to about $2.5 \times 10^{-12}$ and may be about $1.5 \times 10^{-12}$ seconds. The wavelength can be from about 990 nm to about 1200 nm and preferably is about 1035 nm. The system is designed to cut the lens, lens capsule and corneal tissue, with minimal collateral damage, by the mechanisms of plasma mediated ablation and photodisruption of targeted tissue at the beam focus. The precision incisions are generated by computer-controlled scanning of the position of the laser beam focus in a three dimensional pattern at the target location. The laser energy is delivered to the eye through a disposable, patient interface device (PID) that consists of a Suction Ring, which is affixed to the eye, a precision fused silica window that allows the laser light to be coupled into the eye through a refractive index matching cell, and a Split Ring Arm that expands and locks into the Suction Ring thereby fixating the eye throughout the procedure. The index matched light coupling allows the focused laser pulses to be accurately delivered to target locations within the natural crystalline lens.

An embodiment of a laser system may include the following: a pulsed laser used to photodisrupt or cut the natural crystalline lens, lens capsule and/or cornea to effect the treatment; an optical beam delivery system to deliver the laser pulses to target locations within the crystalline lens, lens capsule and cornea; a moveable optical head to allow the laser to be moved into position to dock to the patient interface device; a patient interface device and controlled force docking mechanism that positions and mechanically stabilizes the patient's eye; a biometric imaging system to measure the position and shape of the crystalline lens and cornea as well as the cataract degree and location so that the photodisruption pattern can be accurately placed; a camera system to provide the user a view of the eye during the eye docking operation, to provide high resolution iris images used for Iris Registration, and to provide periodic snapshots of the lens and cornea to allow the system and user to monitor the laser treatment; a locomotion system to allow motorized or passive repositioning of the system within the operating room or facility; a built-in test (BIT) capability to verify system performance prior to use; a software control system that controls the laser, beam delivery, patient positioning as well as generating and storing patient and treatment information; and a user interface to permit the user to manage all aspects of the system; and a wireless network interface to support remote diagnostics, on-line purchase of procedure certificates and import/export of patient diagnostics and treatment data.

In an embodiment of a system, the system has temperature stabilization hardware and software to control the temperature of temperature sensitive systems, components and equipment. For example, a resistive heater and hardware control loop can be used to maintain the camera mount at a constant temperature. This provides benefits, including among other, a decrease in system warm-up time, an increase in the operating temperature range and improves measurement accuracy. In a preferred embodiment dual redundant temperature sensors and safety features are utilized to detect, mitigate and control problematic temperature conditions, such as, for example a failed heater, lack of heat, over-heating, and a controller runaway.

In an embodiment of the system there is a material property determining computational assembly; e.g., a biometric determination system, or biometric system. The material property determining assembly has the capability to determine a material property of a structure of the eye, e.g., opacity, density, toughness, elasticity. This material property determining assembly further has the ability to make these material property determinations for discrete areas, e.g., volumes, within a structure of the eye. Thus, for example the density of various areas of the lens of the eye can be determined. Preferably both the material property, and the absolute (i.e., position relative to the laser beam path, and therapeutic laser beam) and relative location (i.e., distance to other structures, for example distance from the AP axis, the lens capsule or both) of that area of the lens having that material property can be determined. The material properties of volumes of less than about 100 mm³, less than about 50 mm³, less than about 20 mm³, less than about 10 mm³, and less than about 1 mm³ can be determined, it being understood that larger and smaller volumes are also contemplated. Thus, for example a biometric system can determine the density of different portions of a cataract and the lens material surrounding the cataract. The biometric system can associate through computations the density determination with grades of a cataract, or with other metrics. The density determination can be based upon, or derived from the opacity of the material.

The system may place cataracts within one of five grades. They are 1) a cataract with no detectable nucleus, 2) a cataract wherein the nucleus is detectable, but not dense, 3) a cataract with a dense nucleus, 4) a cataract with an extremely dense nucleus, and 5) a cataract wherein no light can transmit through the material. When grading the cataract, the system determines the boundaries between these grades is based-upon the location of the cataract and degree of light scatter detected by the system, as detected by the system and processed by the system's own imaging software. This grading is done preferably in conjunction with forming a theoretical model of the lens using-in-part data acquired from the eye as well as the use of algorithms based-upon the theoretical eye model. Thus, preferably the grading system using actual, observed scatter, preferably augmented by calculated and modeled information regarding the lens.

The cataract's grade will help the system determine the powers, repetition rates, and pulse widths that can be used to provide the minimum amount of photodisruption necessary to remove the material. Thus, there is provided custom laser-delivery patterns including custom pulse-length repletion rates and powers for the various cataract densities, with the denser material having greater power and the less-dense material requiring less power. The generation of these custom laser-delivery patterns, based-in-part upon a cataract's grade, is described as follows.

Once the cataract has been graded, a laser shot pattern can be delivered to the eye, and in particular to the lens of the eye. The laser shot pattern can be contained in the memory of the system's control system, and can be selected by the control system based upon the biometric determination, by the doctor based upon the biometric determination, and combinations thereof. For example, the control system can suggest the laser pattern based upon the system's grading of the cataract, with the doctor having the capability to accept and use the systems suggestion. In this manner the laser system will be grading and providing a laser shot pattern based at least in part on a biometric determination of a property of the lens material.

Further, the laser pattern can have laser shots of different powers, spacing and combinations and variations of these. For example, the power of the laser beam can be changed so that the predetermined laser shot pattern, includes predetermined laser powers for laser shots within that pattern. Additionally, the laser shot spacing, the power, and combinations and variations of these, may be changed during photodisruption process. For example, in this manner high laser powers, greater densities of shots and combinations and variations of these, can be used in areas in the lens that are denser, while lower laser powers, less densely spaced laser pulses, and combinations and variations of these, can be used on less dense areas. The less dense areas may for example be located near the lens capsule. In this manner the system, preferably utilizing a single therapeutic laser, is capable of delivering a laser shot (and shot pattern) having a higher laser power to an area of the lens of higher density; and another laser shot (and shot pattern) to a different area of the lens having a lower density. Preferably, the determination of the denser area, and its relative and absolute, locations, can be determined a material property determining computational assembly; e.g., a biometric determination system, or biometric system. It being understood that this assembly can be an integral part of the laser system, can be a separate stand-alone system, and combinations and variation of this.

Thus, the biometric determination system can determine and provide information about a material property of the lens, and a material property in a particular area of the lens, this information can then form a bases, in whole or in part, for the delivery of laser shot pattern, including the laser power of the shots in the power. In this manner the laser power of a laser shot in the laser pattern can be matched to the material property of the lens.

In an embodiment of a biometric system integrated into a laser system, a biometric system, having optics, imaging, computer (e.g., hardware, processor, software) that may be contained or a part of the control system of the laser system, or may be a separate, or integral, processing and calculating unit, performs an analysis of lens density. This analysis of lens density image, which preferably can be performed during docking of the PID, allows the system to select a surgeon's predefined treatment patterns, for example, the surgeon could have one, two, three, four or more surgeon pre-defined treatment patterns. This reduces patient dock time by minimizing the need for the surgeon to adjust the surgery pattern during the procedure in response to observed lens density. Preferably, the system provides the surgeon with the capability to make the final determination/confirmation of the exact surgery pattern to be used.

In an embodiment the laser system has a docking assist assembly or system, which provides the capability for real-time image processing of the system images (obtained for example from a biometric system) during docking to determine the cornea position relative to the optimal docking position. When the cornea is within the optimal docking region, an indicator is provided, e.g., a visual indicator, such as a yellow cornea apex reference line changing to green. In this manner the system provides the surgeon with visual feedback.

In embodiments of the system capabilities are present for docking assistance based upon the information provided by the biometric system. In an embodiment of a docking assist system, there is a real-time image processing of the biometric system images of the cornea during the docking process. The system tracks the cornea apex and notifies the Surgeon of proper placement by an indicator, such as a visual indicator, e.g., turning a guide line in the GUI, microscope or viewer, from yellow to green. If the Surgeon makes an improper selection regarding docketing, (based on the systems determination), for example by selecting "docking complete", when the system information provides that it is not, a warning message will appear indicating that docking is too high or too low and instruct the Surgeon to adjust the docking. If the cornea is not detected at all, the Surgeon can continue using the currently approved docking process; however, a cautionary message will be provided to verify that the docking height is correct before continuing.

In embodiments of the system capabilities are present for custom fragmentation based upon the information provided by the biometric system. In an embodiment of the system having the capability for a custom fragmentation, an image processing function analyzes the lens image density and classifies it into one of four categories. In an embodiment the surgeon will have pre-defined a custom surgical pattern to be used for each category. The pattern that matches the classification identified by the biometric system algorithm is automatically selected. Preferably, the surgeon then has the option to accept or change the selected pattern based on his own judgment of the image or any previous diagnosis.

In an embodiment of the laser system an iris registration system or assembly is utilized. The iris registration system, such as for example, the iris registration systems disclosed and taught in U.S. patent application Ser. No. 14/444,366 the entire disclosure of which is incorporated herein by reference, provides among other things, improved ergonomics, whereby the system analyzes the live image of the iris and rotationally matches (i.e. "registers") the image with an image of the patient's iris provided by a diagnostic system. This allows the system to automatically rotate the axis of the partial thickness arcuate incisions to the astigmatism axis specified by the diagnostic system. This decreases patient dock time by eliminating the need for the surgeon to manually rotate the treatment pattern to align with ink marks. Preferably, the system provides the surgeon with the capability to make the final determination, adjustment, or confirmation of the automated placement of the arcuate incisions.

Figure 8:
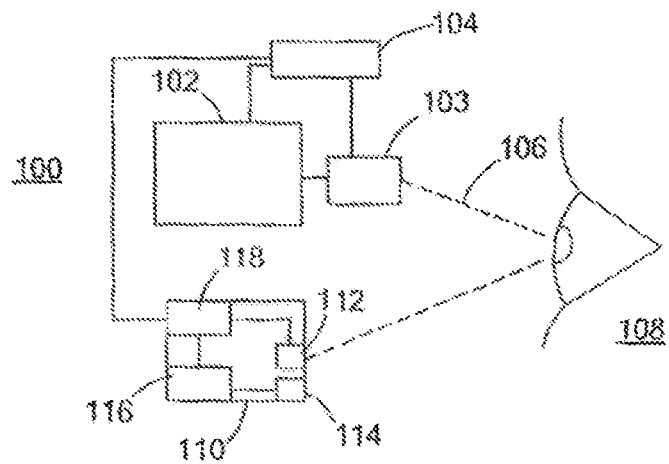
FIG. 8 schematically shows an embodiment of a laser therapeutic system in accordance with the present invention.

As schematically shown in FIG. 8, a laser therapeutic system 100 includes a laser source 102, laser optics 103, and a laser control system 104 in communication thereto. The laser source 102 generates a therapeutic laser beam 106 that is directed to an eye 108 of a patient via optics 103. The laser beam 106 is used to perform a variety of medical procedures on the eye 108, such as capsulotomies, lens fragmentation, and corneal incisions. The control system 104 via its communication with the optics 103 and the laser source 102 controls a number of parameters of the laser beam, such as direction, pulse width, and pulse rate. Examples of a possible laser source 102, optics 103, and laser control system 104 are disclosed in U.S. Pat. Nos. 8,262,646 and 8,465,478, the entire contents of each of which are incorporated herein by reference.

In communication with the laser source 102 and laser control system 104 is an analyzer 110. The analyzer 110 includes a light source 112 that illuminates the eye 108. One or more detectors or cameras 114 receive light reflected off the eye 108 and generate images of the eye 108. One image of the eye 108 is a pre-treatment image in that it is taken prior to the patient's eye 108 being subjected to the therapeutic laser beam 106. A second image of the eye 108 is a treatment image and is taken substantially at the time the eye 108 is treated by the therapeutic laser beam 106. The pretreatment and treatment images are stored in a recording medium, such as a memory 116, and are processed in a processor 118, which is in communication with the controller 104, memory 116 and light source 112. An example of an analyzer 110 that can be used is the Topcon CA-200F Corneal Analyzer manufactured by Topcon based in Japan.

Figure 9:
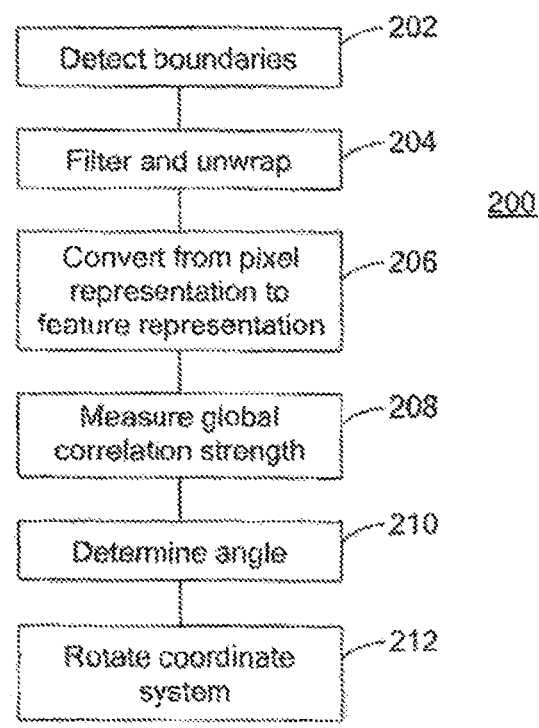
FIG. 9 shows a flow chart of an embodiment of method of registration of an object using the laser therapeutic system of FIG. 1 in accordance with the present invention.

The processor 118 executes instructions stored in the memory 116 so that an algorithm is performed in a very different approach from that used by existing algorithms. The algorithm proposed here is a global correlation algorithm, in which the registration is based on a correlation function that is defined for the pre-treatment and treatment images without singling out particular points in the iris. In operation, the eye 108 is imaged by the analyzer 110 prior to drug-induced dilation. Next, the eye 108 undergoes a laser procedure, such as cataract surgery, using the laser source 102 and laser control system 104. The basic steps/processes for the process or algorithm 200 are schematically shown in FIG. 9 and are as follows:

202—Detect Pupil-Iris and Iris-Sclera boundaries in both images, as well as any eyelid interference;
204—Filter and unwrap the iris in both images;
206—Convert the unwrapped images from pixel representation to feature representation, where each pixel gives rise to one feature vector;
208—Measure global correlation strength between feature maps for each possible angle of cyclotorsion;
210—Take the angle that gives the strongest correlation; and
212—Rotate the coordinate system accordingly.

In operation, the algorithm(s) related to processes 202-212 listed above are stored in the memory 116 as computer executable instructions, wherein the processor 118 executes the instructions so as to process the pre-treatment and treatment images so as to generate a signal that is able to correct the orientation of the therapeutic laser beam. Such signal is sent to the controller 104 which controls the optics 102 and laser source 103 so as to generate a correctly oriented laser beam 106.

Boundary Detection—Process 202

The easiest boundary to find is the pupil-iris boundary, as this boundary is extremely strong and the pupil itself is uniformly dark. An elliptical fit to the boundary is first found by approximating the center with a histogram method, performing a radial edge filer from this center on edges extracted with the standard canny algorithm, extracting up to 4 circles with a RANSAC algorithm, and combining matching circles together into an elliptical fit. An additional algorithm is used to fine-tune the result even further, which is basically a simplified implementation of Active Contours or Snakes. This algorithm takes as input the image and a previously found elliptical fit to the pupil boundary, and "explores" the image in the neighborhood of the boundary at several values of theta, finding the location that maximizes the radial component of the gradient of intensity values in the image for each theta. This builds a list of points that describe the boundary point by point in polar coordinates (with the origin remaining the center of the previously found ellipse). A simple Gaussian smoothing is then performed on this list of points to enforce continuity. The smoothed list of points is then taken to be pupil boundary.

Figure 10:
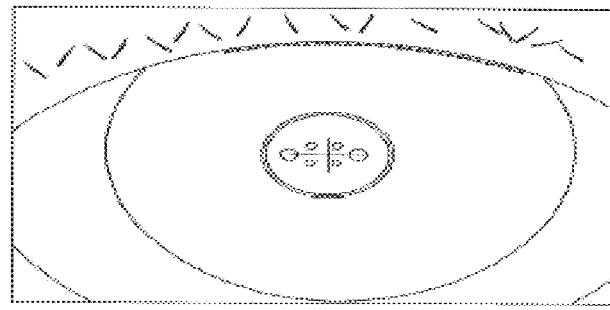
FIG. 10 shows a possible image used for performing an embodiment of a process for detecting a boundary of an iris and eyelid interference per the process shown in FIG. 9.

To find the iris-sclera boundary in the diagnostic image of FIG. 10, for example, a circular splines algorithm is used, which traverses through an appropriately restricted three dimensional parameter space (center and radius of a circle) treating distinct angular regions separately, seeking to maximize the dot product between the gradient and the outward normal of the circle splines. The basic algorithm structure can be formulated as the following: for each choice of center and radius, form a circle and assign a score for this circle to each angular region from the radial component of the gradient; for each angular region for which the score obtained with this circle is higher than the previous high score for that angular region, store the new high core and the circle that achieved it. This results in a set of circular splines which are then filtered, removing splines that don't fit very well with the others. Eight splines are used for the image in FIG. 10, thus rendering eight separate angular regions of 45 degrees each.

To find the iris-sclera boundary in the treatment image, the ellipse describing the limbus in the diagnostic image is transferred to the treatment image by scaling the two radii of the ellipse according to the differing resolutions of the two cameras, assuming no cyclotorsion in placing the axis of the ellipse, and assuming that in the treatment image the limbus will be approximately concentric with the dilated pupil. This constitutes a good initial approximation, which is then improved upon by first using the same snakes algorithm that is used for the pupil boundary and then fitting an ellipse to the resulting set of points.

Figure 11:
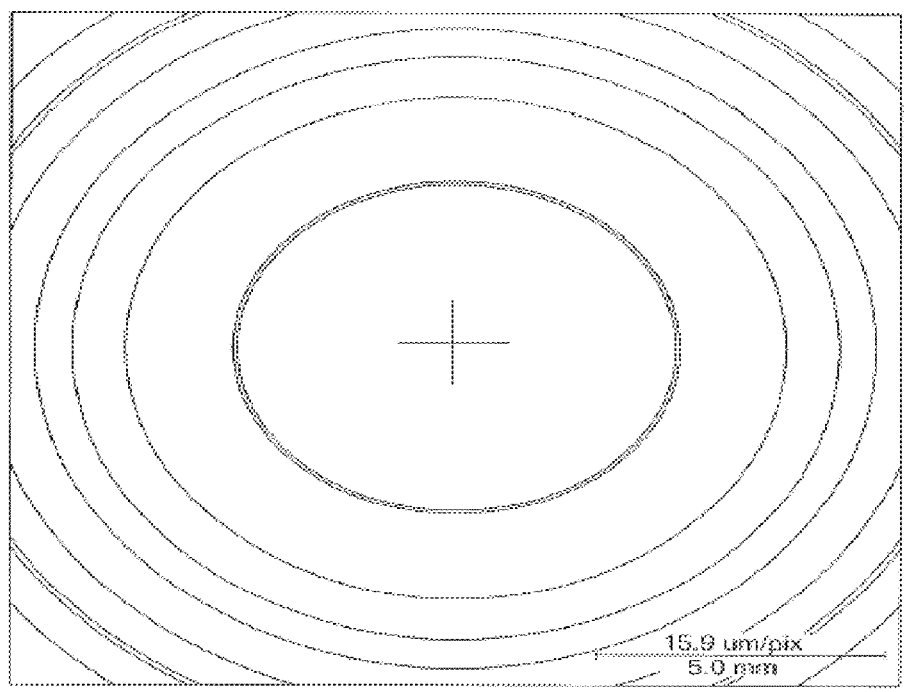
FIG. 11 shows a possible treatment image used for performing an embodiment of a process for detecting a boundary of an iris per the process shown in FIG. 9.
Figure 12:
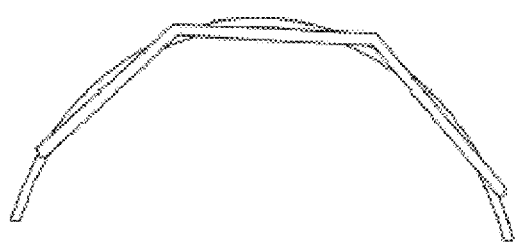
FIG. 12 schematically shows a possible way of approximating a circular arc during performance of an embodiment of a process for detecting a boundary of an iris and eyelid interference per the process shown in FIG. 9.
Figures 13A, 13B:
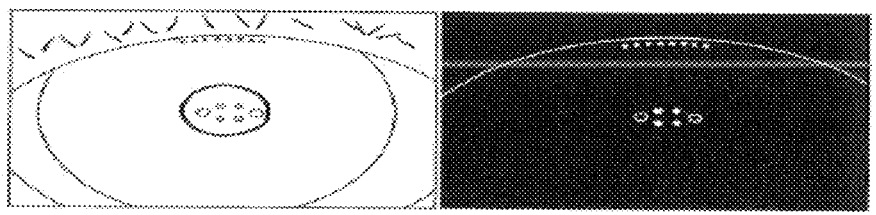
FIGS. 13 A-F show an embodiment of a process for reducing eyelid interference per the process shown in FIG. 9.
Figures 13C, 13D:

Often, images taken at a diagnostic device, such as analyzer 110, have some degree of eyelid or eyelash interference concealing a portion of the iris. To mask out these regions from consideration in the registration algorithm, eyelid/iris boundaries must be segmented in an image obtained from analyzer 110, such as shown in FIG. 13(*a*). The first step in the segmentation is to detect all small glints in the image, as there tends to be several of these small glints in the neighborhood of eyelid/iris boundaries. Next, a Difference-Of-Gaussians (DOG) filter is applied, which has been empirically parameterized to remove eyelid/iris boundaries from the image (i.e. the area containing the boundary becomes dark) and converts image (a) from FIG. 13 to the image of FIG. 13(*b*). The image is then converted to an inverted binary image—all pixels below a certain threshold are made white, and all other pixels are made black, resulting in image FIG. 13(c). Pixels belonging to small glints are then "filled in" (i.e., made white). The resulting image has a very thick white edge representing the eyelid or eyelash interference with the iris, as well as some extraneous smaller white edges. These extraneous edges are then filtered out by a novel algorithm utilizing the integral image concept, which produces the image of FIG. 13(d). The underlying concept is similar to the classical "erode" algorithm that is often used for getting rid of small extraneous clusters of edges, with the difference being that the average intensity in the "neighborhood" of a white pixel determines whether it is kept or removed, as opposed to the amount of its neighbors that are white making the determination. The "neighborhood" is shaped according to what is expected for the eyelid. The eyelid can be represented quite well by a low-curvature circle, which can be crudely approximated by a "trapezoid top" shape. Thus, each pixel is given three chances to pass an integral image test one with a horizontal rectangle, one for each of two parallelograms tilted 45° as shown in FIG. 11.

If the threshold for minimum average intensity is met in either one of these three tests, the pixel remains white; otherwise the pixel is made black. Then, a circular mask is applied to mask out areas that are too close to the top and bottom borders of the image to be considered, and the classical erode algorithm is applied to thin out the eyelid/eyelash interference region as well as get rid of any lingering undesired edges, resulting in the image of FIG. 13(e). The reason why the novel "erode-like" algorithm is used in the first place is because the "erode-like" algorithm described here gets rid of the vast majority of the undesired edges while essentially leaving the edges of interest completely intact, allowing for the classical erode algorithm to simply finish the job. If this algorithm is skipped in favor of using only the classical erode algorithm, it becomes impossible to have a threshold that gets rid of all extraneous edges without also getting rid of large chunks of the eyelid/eyelash interference region. Basically, this algorithm allows for a decoupling of filtering out tiny extraneous edges and thinning out thick boundaries.

Figures 13E, 13F:
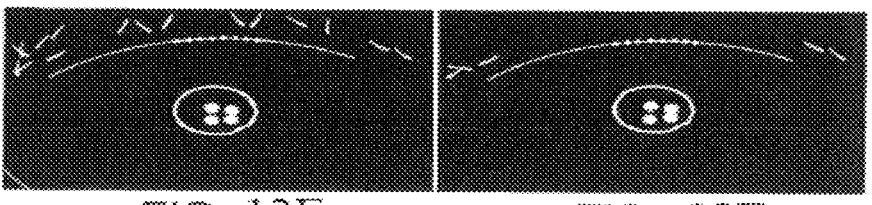
Figures 14A, 14B:
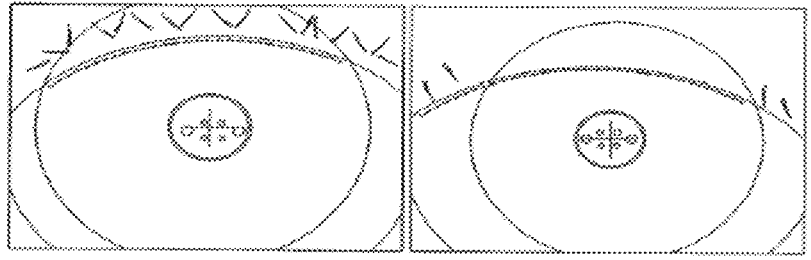
FIGS. 14 A-B show possible images showing the results of reducing eyelid and eyelash interference per the process shown in FIG. 9.
Figure 18A:
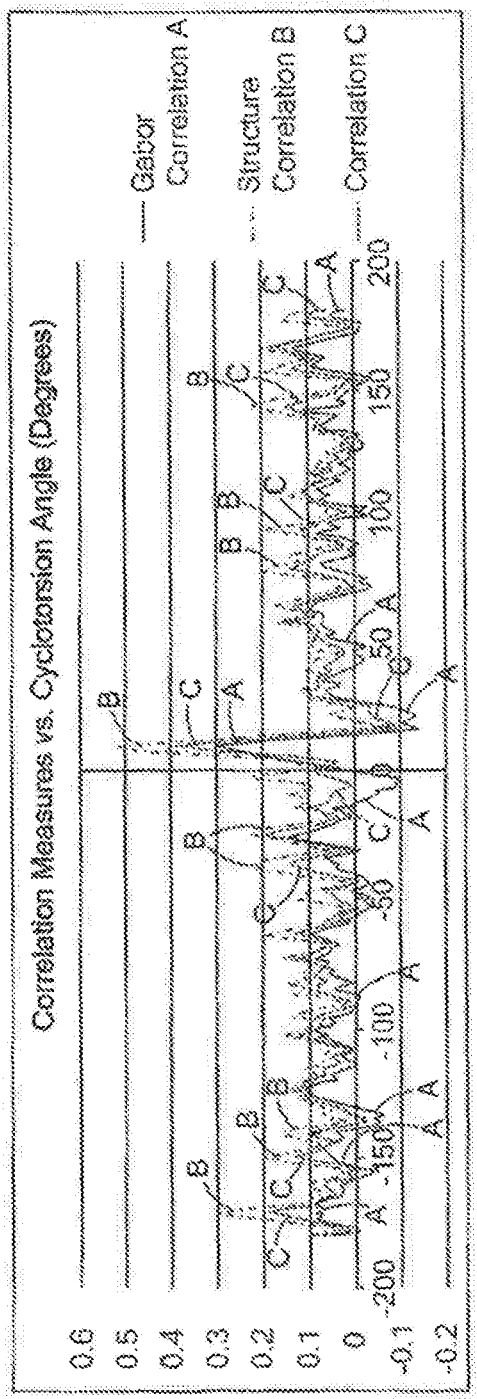
FIGS. 18 A-B show graphs of possible correlation measures vs. cyclotorsion angle relationships per the process shown in FIG. 9.
Figure 18B:
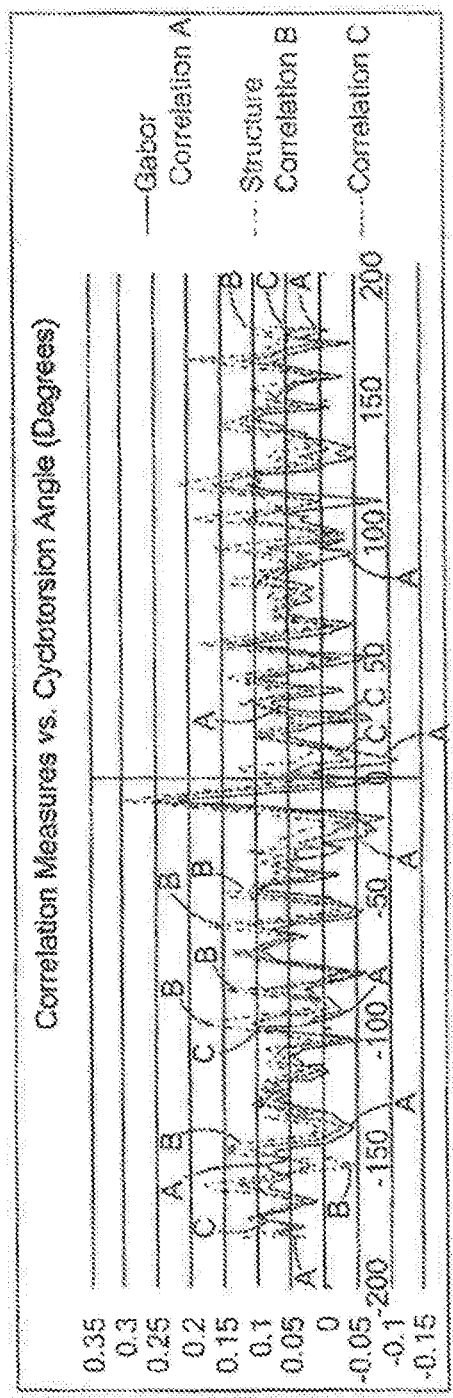
Figure 20A:
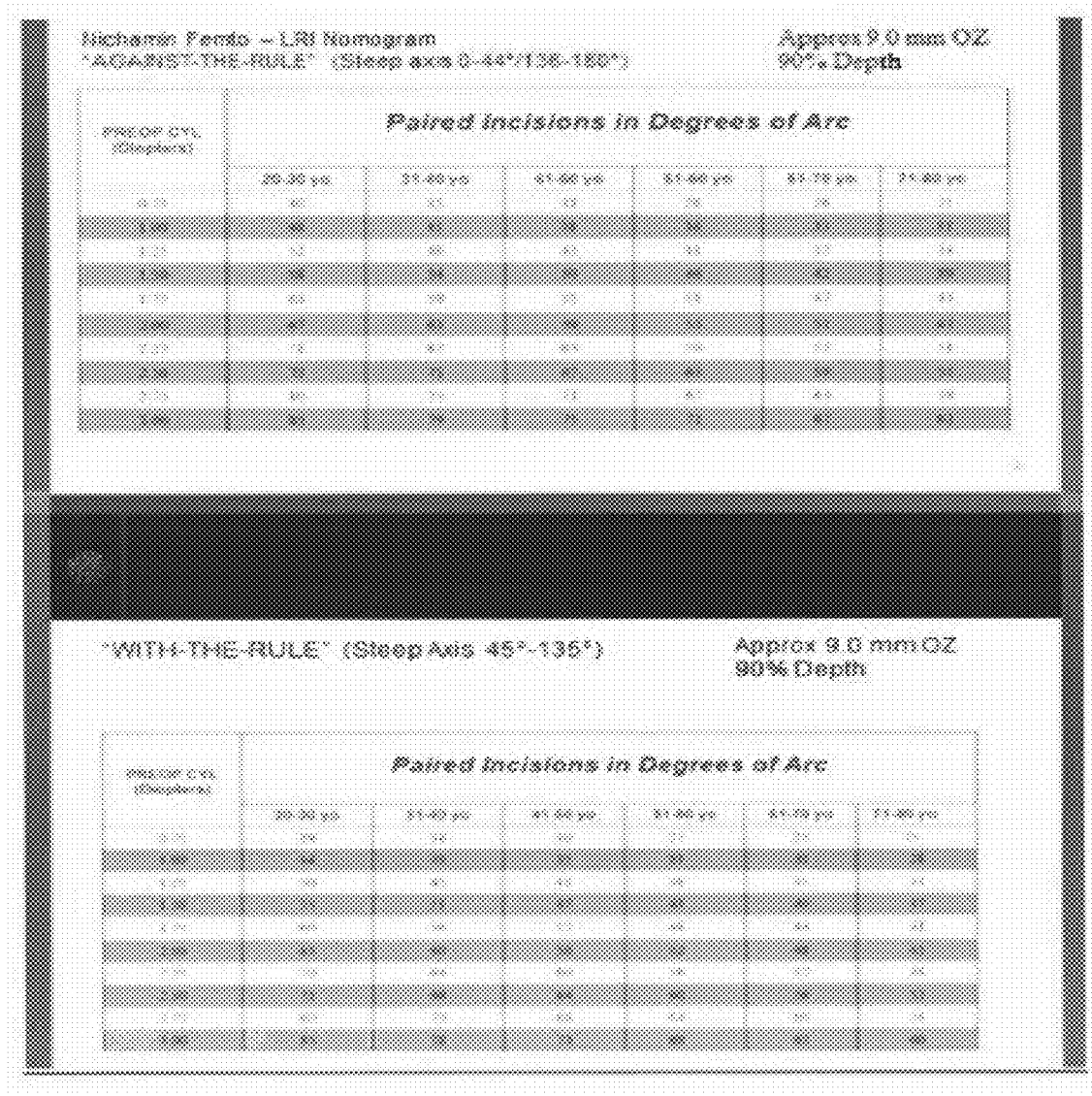
FIGS. 20 A-E show other examples of planning tables that may be used with the GUIs shown for developing a treatment plan.
Figures 20B, 20C:
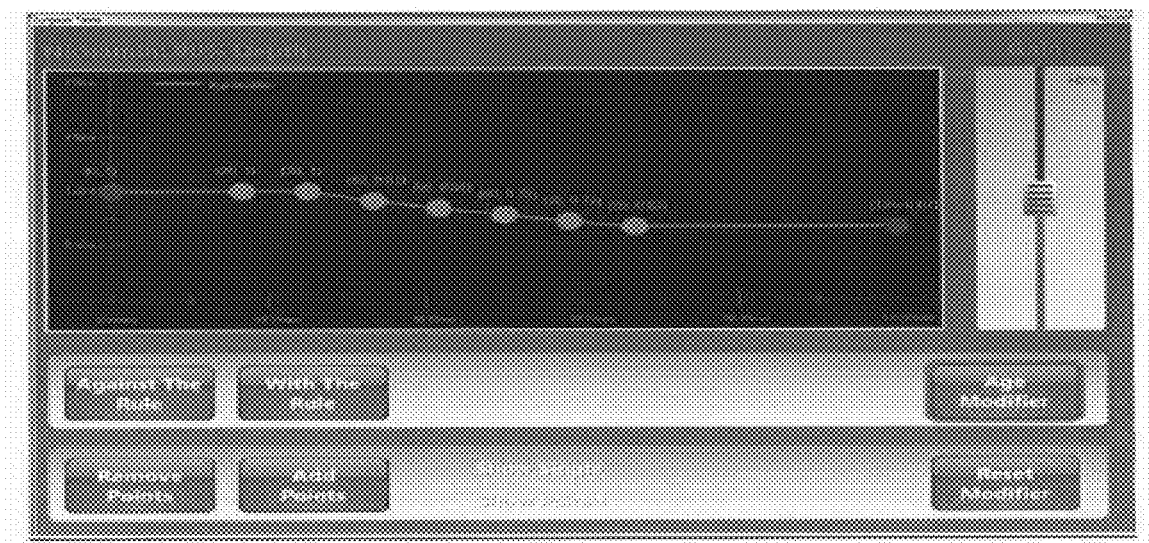
Figure 20D:
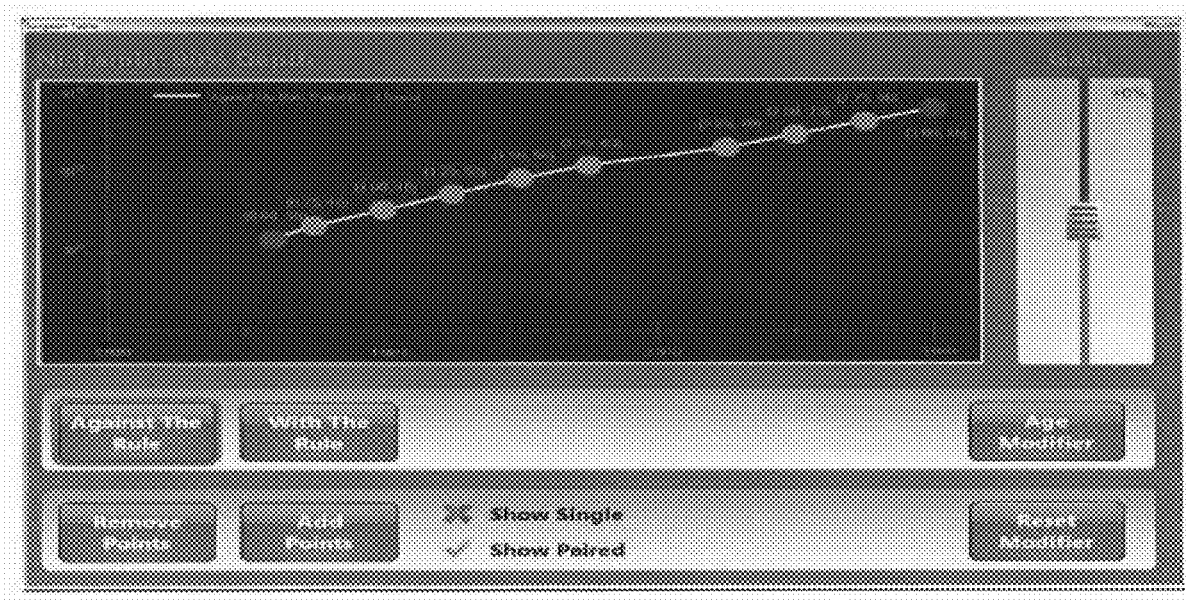
Figure 20E:
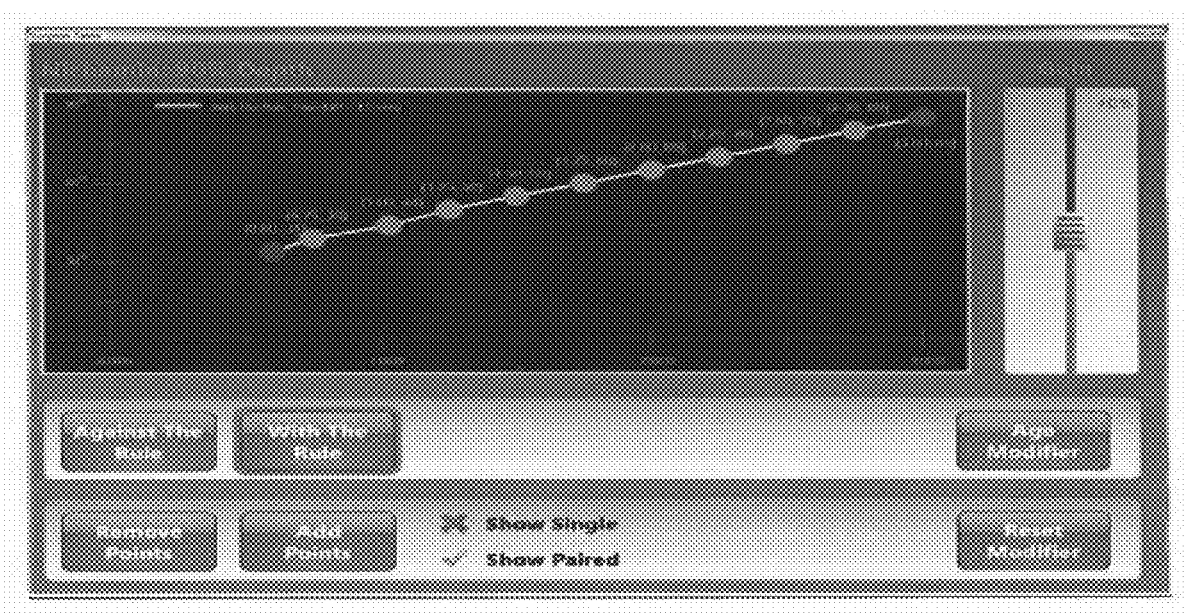
Figure 21A:
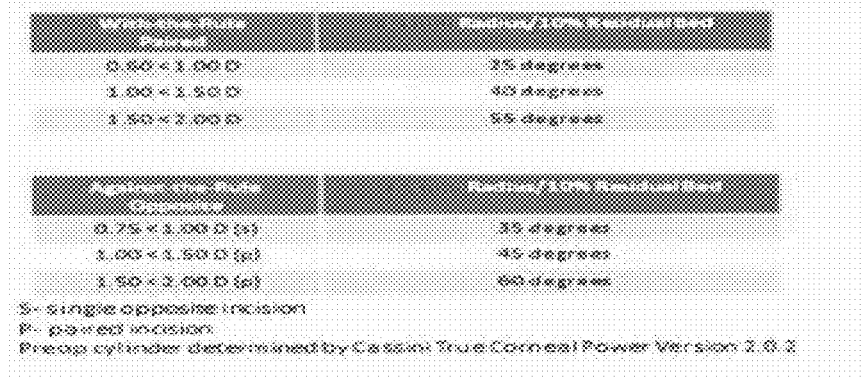
FIGS. 21 A-E shows other examples of planning tables and GUIs that may be used to generate a treatment plan.
Figure 21B:
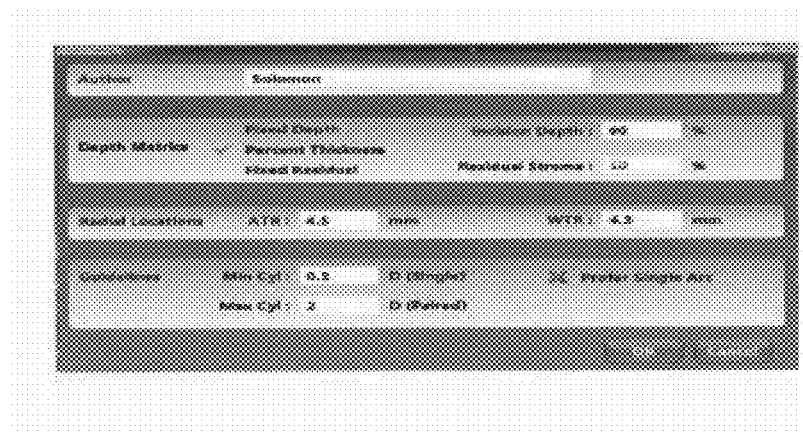
Figure 21C:
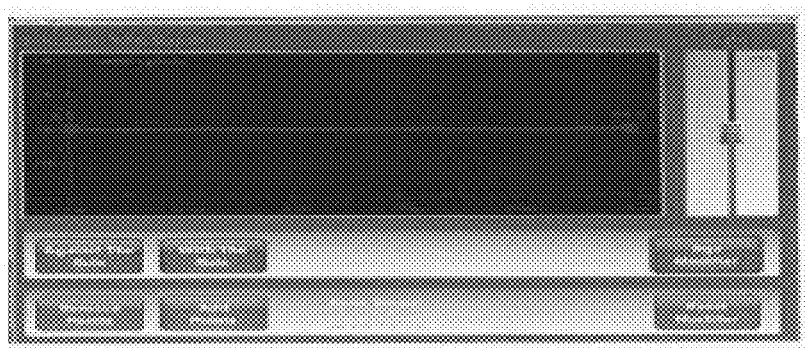
Figure 21D:
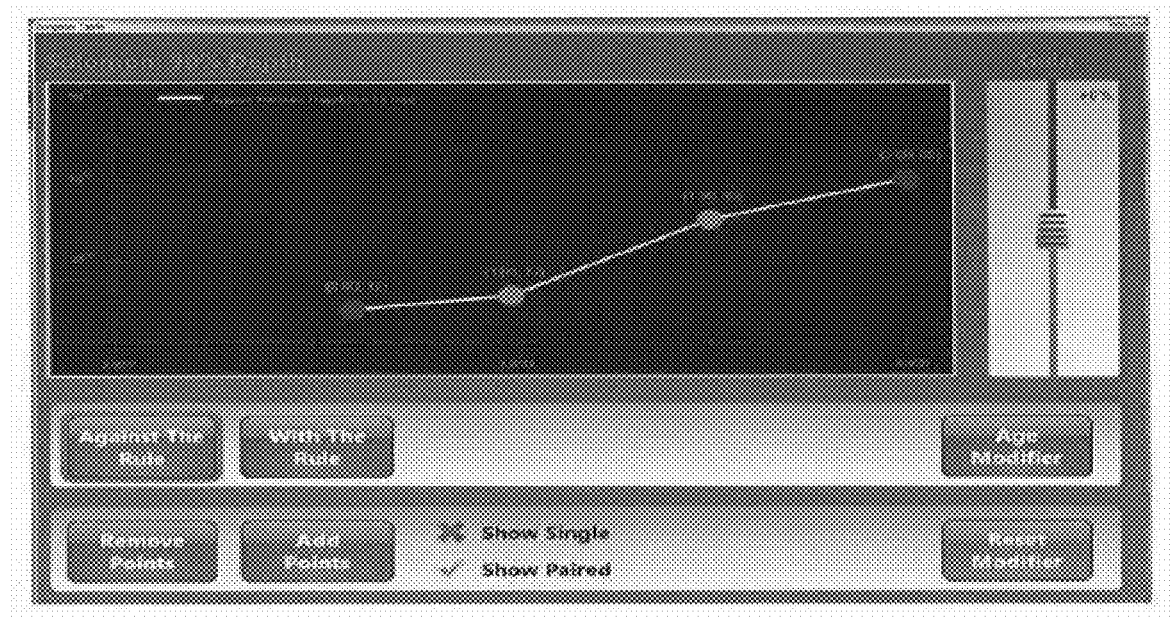
Figure 21:
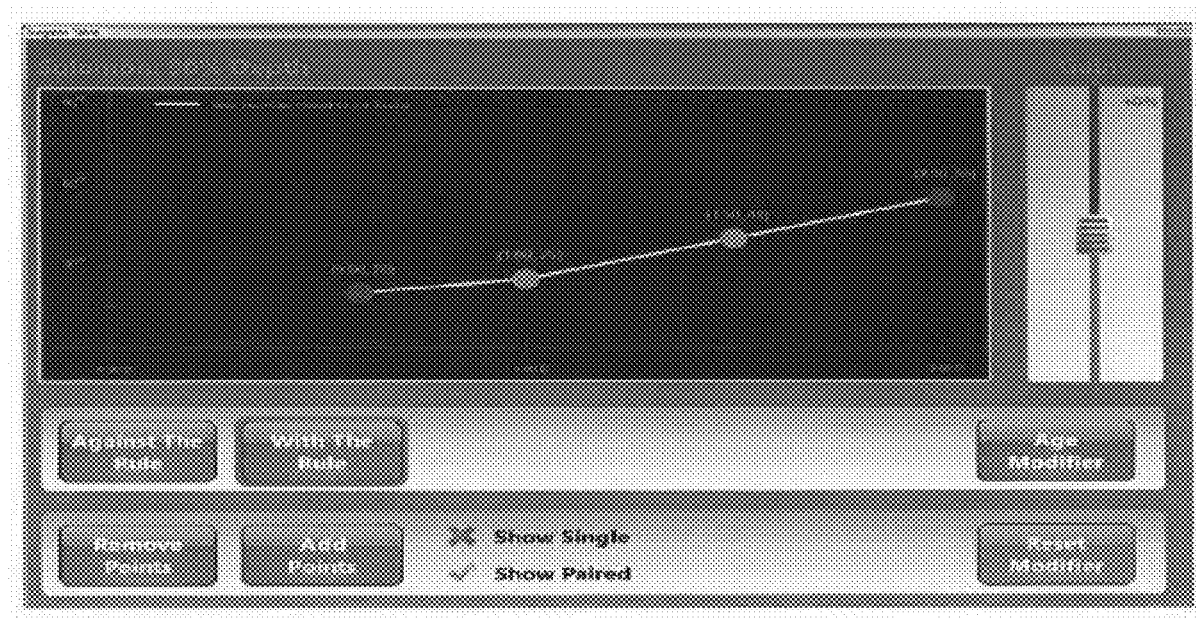
Figure 22:
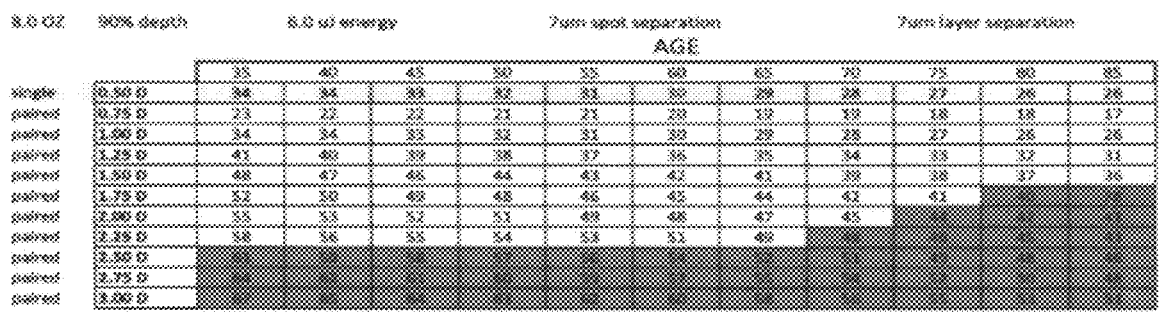
FIG. 22 shows an example of a planning table useful in generating a treatment plan.

Finally, a bottom-up filter is applied to the upper eyelid region resulting in the image of FIG. 13(f) and a top-down filter to the lower eyelid region, and a RANSAC circle finding algorithm is used on the resulting image to extract the best circle for each eyelid. The RANSAC algorithm is restricted to the area above the pupil for the upper eyelid and the area below the pupil for the lower eyelid (in other words, the pupil is masked out). If RANSAC is unable to find a curve containing at least an empirically determined number of pixels, it is assumed that there is no (or negligible) eyelid interference. If eyelid interference is found, then the region of interference is masked out of both the iris-sclera boundary detection algorithm and the registration algorithm. Example results for eyelid/eyelash interference detection are shown in FIGS. 14A-B.

Filtering and Unwrapping the Iris—Process 204

The iris during dilation is approximated by a rubber sheet model, such that the iris in the non-dilated eye is assumed to basically be a stretched out version of the iris in the dilated eye. In this approximation, a pseudopolar mapping is carried out to unwrap the iris into a rectangular image in which the dimensions represent angle and distance from the inner (pupil) boundary. If the boundary detection is perfect, then the top row of this image will perfectly represent the pupil boundary and the bottom row will perfectly represent the sclera boundary. The size of the averaging area used to fill each pixel in the unwrapped image increases linearly as a function of distance from the pupil center. Obviously, there is technically information loss associated with this approach, with the amount of information loss increasing with distance from the pupil center. However, this loss does not have any noticeable impact, and in fact running registration algorithms on these images rather than the original images results in both a cleaner implementation and faster run time.

In an embodiment of the laser system, iris registration is achieved first through the import of patient diagnostic data from a topographer through the wireless network. The imported data includes an astigmatism axis relative to an image of the patient's iris. The optics assembly, such a system looking along the laser beam path, likewise generates an image of the iris. The software algorithm rotates the image to find the position with the highest correlation of iris features with the diagnostic image of the iris. Once found, this allows determination of the astigmatism axis relative the laser system and the treatment incision axis is adjusted accordingly. This feature reduces the need for manual adjustment of the treatment axis to ink marks placed by the surgeon and reduces procedure time. Preferably, the system provides the surgeon with the capability to make the final determination to either approve or override the iris registration feature's placement of the arcuate incisions.

In an embodiment of the laser system a target loss detection system is utilized. This system can detect the loss of water, loss of suction, or adverse conditions, relating to the PID, docketing, and other features of the system. In an embodiment of this system, the system continually analyzes images for features, conditions, indications, that are known precursors to detachment of the suction ring from the eye and/or loss of water from the PID. This system can provide an alarm, an indication, can halt the treatment, and combinations and variations of these.

In embodiments of the laser system a communications network is utilized with the laser system. In this manner the laser system can be part of a network, in which the laser system is in communication with other components of the system, such as medical record storage devices, e.g., data storage devices, memory and servers, billing systems, enterprise data systems, the systems of the laser system manufacturer, seller or servicer. Embodiments of these networks and systems can be for example, integrated system, a system having sub-systems, a system that is partially integrated, a system that is a distributed control network, a system that is a control network, and an independent system, and combinations and variations of these and other configurations. These systems can be wireless, cabled and combinations and variations of these. The networks and systems may be, for example, Ethernet based networks, wireless networks, dedicated or specified automation and control based networks, e.g., employing commercially available protocols, optical fiber networks, and combinations and variations of these and other types of automation, data management, billing, and control networks now available or later developed. Upgrades to laser software can be provided along this network. And data can be pushed or pulled from various locations along the network.

In an embodiment of a network system for a laser system, a wireless Ethernet router is included in the laser system. This is can be for example a commercial off-the-shelf device used to communicate between the laser system and the a network server, or servers at different locations, include network servers located at the surgical facility, doctors off or location where the laser system is being utilized. The wireless router supports, for example, the following capabilities:

Remote Diagnostics: The automatic transfer of system logs to the laser system supplier's server (e.g., the manufacturer's server, a service provider's server, or other entity relating to providing, upgrading, operating, servicing and maintaining the laser system) to allow access and diagnostics. The manual transfer (by User request only) of encrypted patient/procedure data to support analysis of system performance. Preferably, patient identification is removed prior to transmission. Preferably the laser system contains the capability for remote diagnostics, which can be executed separately from the primary surgical procedure application.

Certificate Purchase: The on-line purchase of procedure certificates by directly accessing the supplier's server via, for example, a user interface. Preferably, this provides the capability for secure communication of laser system user private data.

Patient/Diagnostic Data Import: To support the integrated office environment patient data, including diagnostic data from a corneal topographer, and surgical treatment plans can be imported from a storage device, such as separate Network Access Storage (NAS) device. This supports off-line patient planning, improves throughput and reduces human error by eliminating manual data entry at procedure time. The patient data importation has the additional functionality of allowing the system to detect if the proper treatment plan is being used for the patient. Specifically, the system can use the imported data, including previously-acquired data regarding the patient's iris, to determine if the scanned iris belongs the the patient for whom the treatment plan was developed. The system may also upload and cross-check a patient's medical history as an additional safeguard. If a patient's iris does not match the iris stored with the treatment plan, the system may alert the surgeon or otherwise prevent the surgery from happening.

Patient Treatment Data Export: To support the integrated office environment patient treatment data can be exported to a separate Network Access Storage (NAS) device. In addition, hardcopies of the data can be sent to a wireless printer device located on the network. Certain embodiments make it possible to automatically bill the patient and their insurance for the procedure. In said embodiments, the networked system would use data obtained during the surgery, along with the patient's biographical data, and medical history, to automatically bill the patient's insurance provider, Medicare, and/or Medicaid.

In an embodiment of the laser system the system provides the capability for the surgeon, preferably at the time of the treatment planning, to select if they would like to plan arcuate incisions as they do currently, based on biometry and other patient factors and retain the plan on the laser system, or on a storage device associated with the laser system via a network.

In an embodiment of this feature there is a GUI having planning graphics that provides the operator, e.g., a surgeon, with the capability to plan arcuate incisions, as well as other cuts and procedures, by among other things, importing biometric measurements to an arcuate incision GUI, such as a planning table. The arcuate incision planning table can be populated with parameters entered by the surgeon to define the location, depth and extent of the surgeon's intended arcuate incisions based on individual patient biometric measurements, and other factors as defined by the surgeon. This procedure allows surgeons to, among other things, reduce the chance for transcription error by importing biometric measurements to the arcuate incision-planning screen and allowing surgeons to define the location, depth and extent of their arcuate incisions based on these measurements. In addition, the arcuate incision planning, storing, and both, capability allows surgeons to retain their personal plans for later use. This capability provides, among other things, increased surgical operating room efficiency by mitigating, reducing, and preferably obviating the need to repeatedly enter the same parameters prior to each case. Other information that may be stored and utilized can include preferred clear corneal incision dimensions or capsulotomy diameter information.

Further, the system allows for the use of planning tables, as shown in FIGS. 20 A, 21 A, and 22 to inform the surgeon where to place arcuate incision in the cornea to address the induced astigmatism caused by changes in the steep axis that result from surgical procedures, such as cataract surgery. These planning tables may be nomograms, including but not limited to Johnson and Woodcock nomograms. Further, it is contemplated that machine learning may be applied to the information obtained from the planning tables, enabling the machine to optimize both the tables and the procedures. This provides particular advantage where system is being utilized in a population having certain characteristics.

FIGS. 6A-D, 20 B-E, and 21 B-E represent embodiments of a GUI that a surgeon may use with the planning tables to assist a surgeon in developing a surgical plan.

Figure 6A:
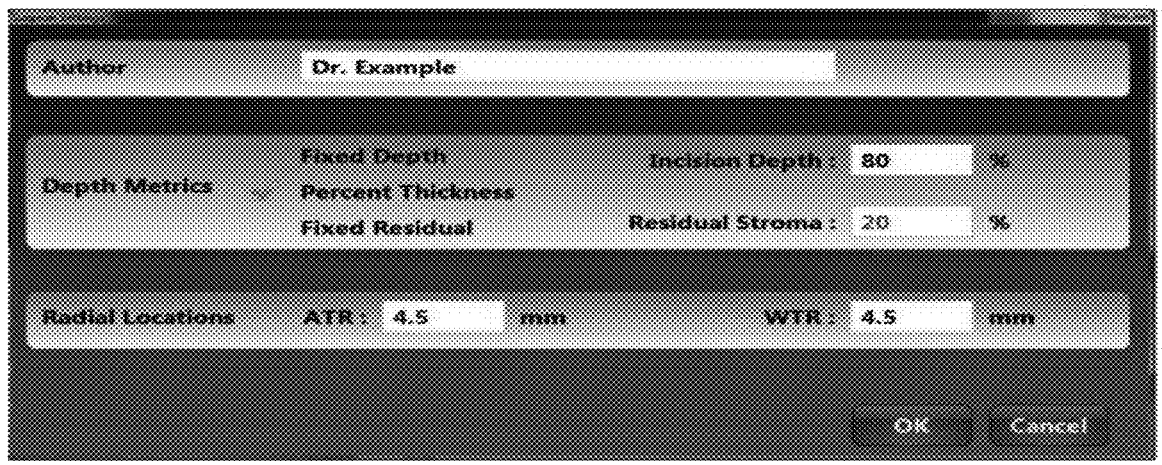
FIGS. 6A-G are examples of Graphical User Interfaces (GUIs) that may be used when developing a surgical plan.
Figure 6B:
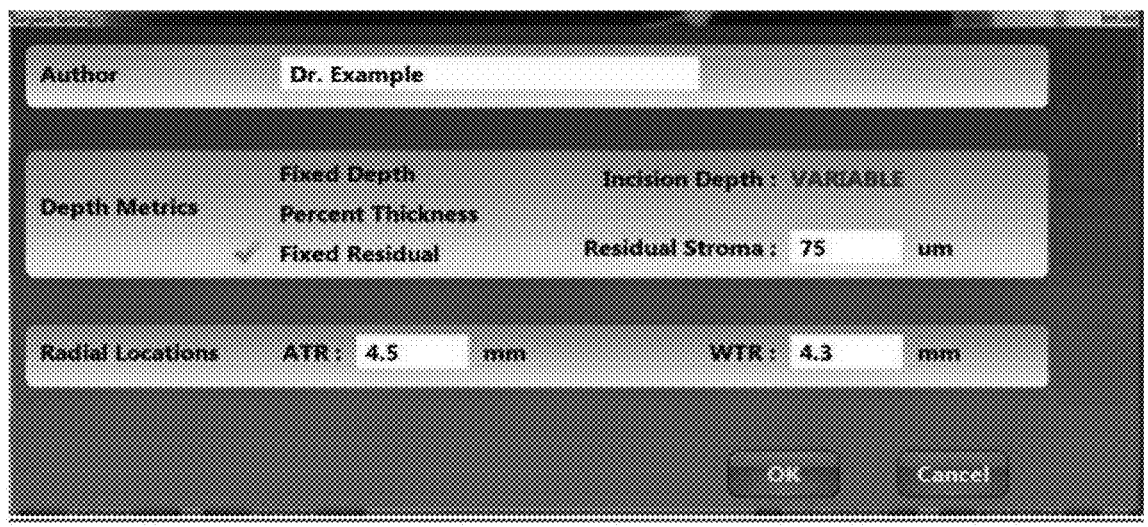
Figure 6C:
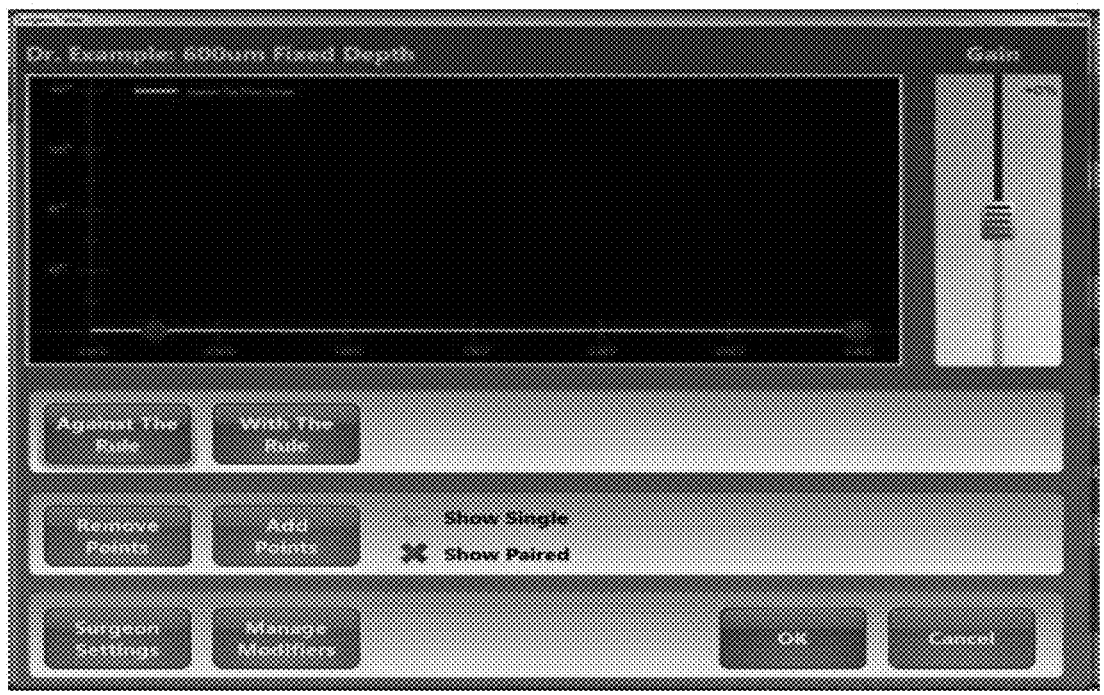
Figure 6D:
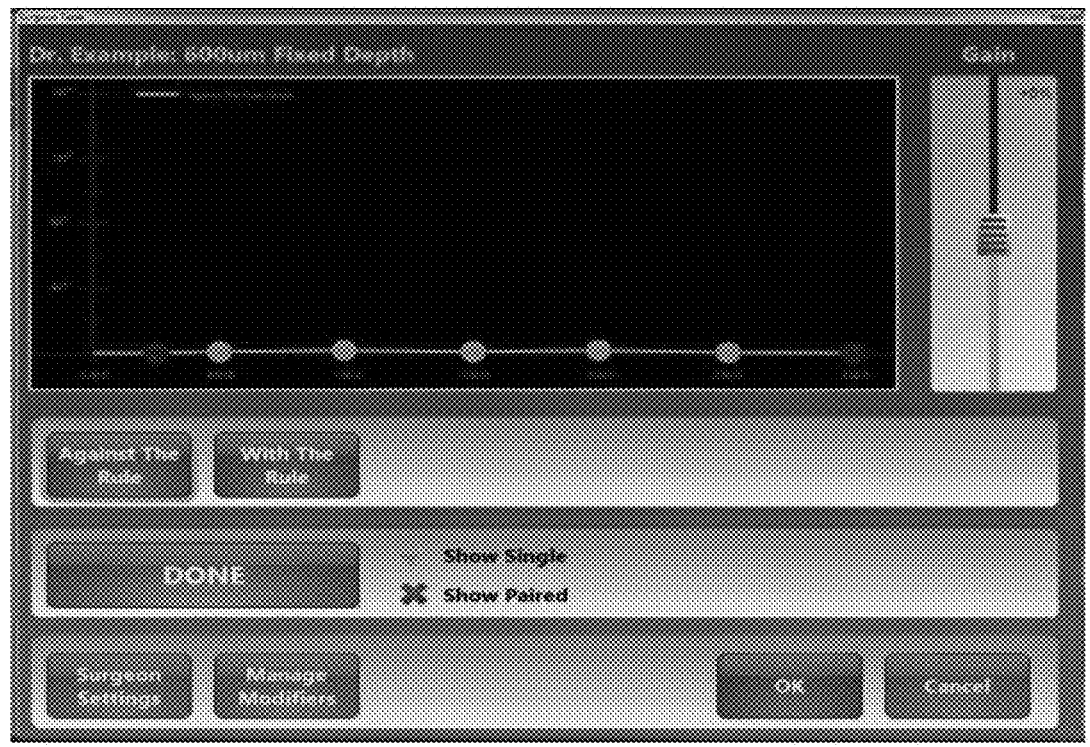
Figure 6E:
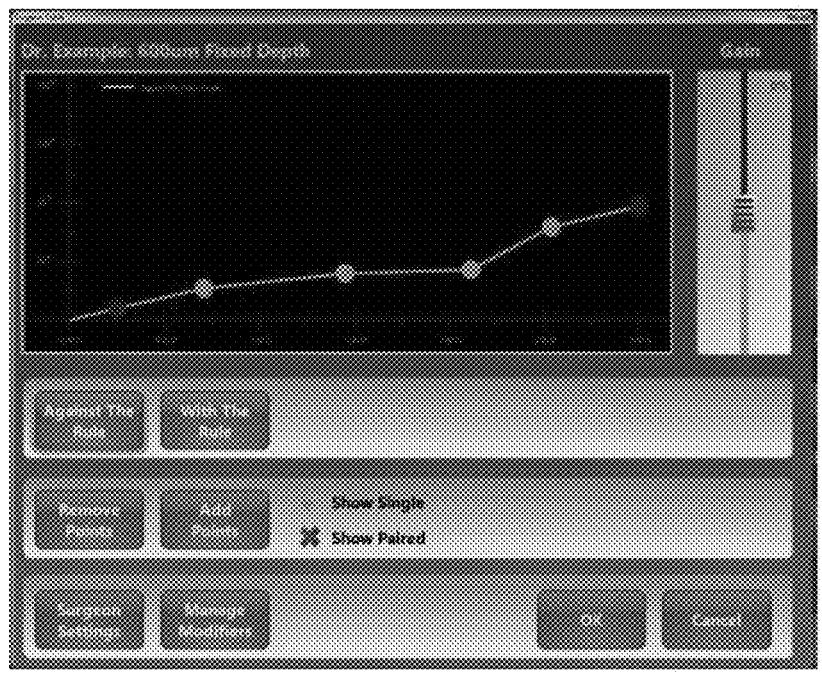

In an embodiment of the surgeon table GUI, the system utilizes a touch screen. Thus, for example, once the points have been added to the modifier table, the operator, e.g., the surgeon, has the ability on the touch screen to drag and drop the modifier values to their own desired values as shown in FIG. 6E.

Figure 6F:
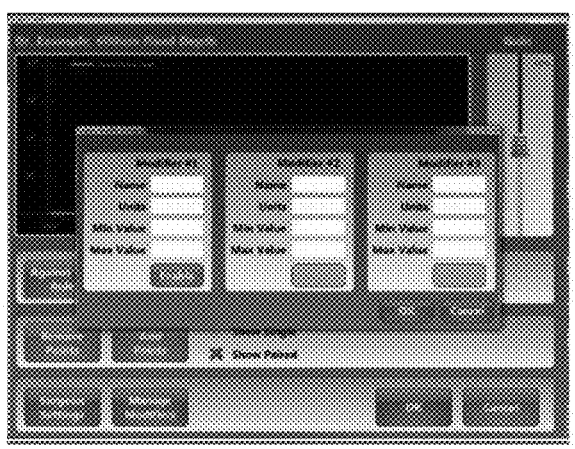
Figure 6G:
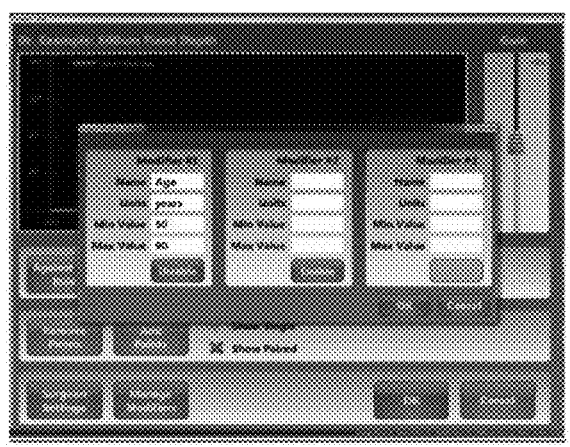

In an embodiment of the surgeon table GUI, the system has the capability to provide for the surgeon to enter additional modifiers as they need. For example, the surgeon modifier screen will not come pre-populate, it is up to the surgeon to add the modifier. FIGS. 6F-G provide examples for how the surgeon can add additional modifiers as they need. FIG. 6F contains the blank modifier table, e.g., unpopulated on the left and the populated screen, e.g., while FIG. 6G shows a populated field with an age modifier, is shown on the right.

Figure 7:
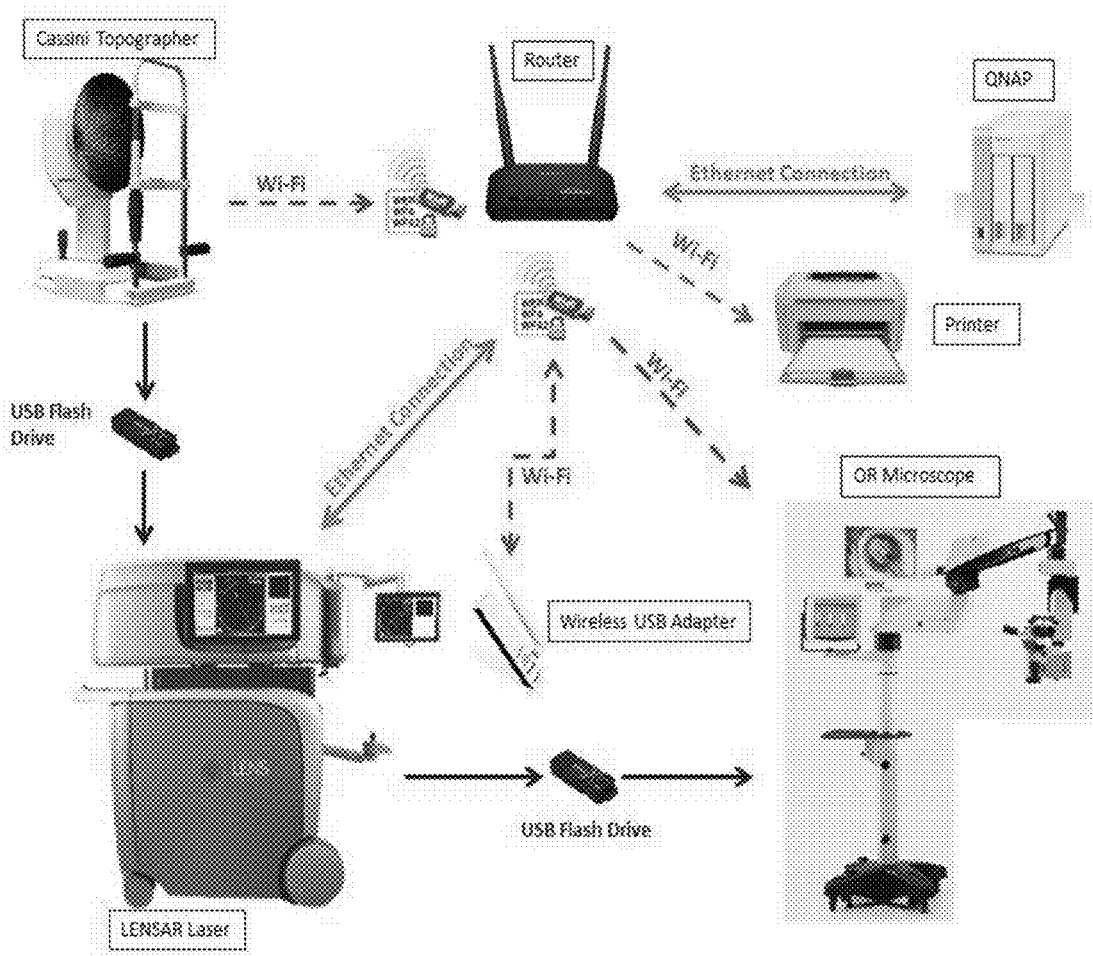
FIG. 7 Shows a networked laser system.

An embodiment of a network system utilizing a laser system is provided in FIG. 7. This embodiment is a wireless network, wherein the LENSAR laser 701 is in communication 701a with a Wi-Fi router 702. This may be by either an Ethernet or Wi-Fi connection. The router 702 is in turn in communication with a Cassini Topographer 703, A QNAP server 704, a printer 705, and an OR Microscope 706. The router is linked to these devices along communication pathways 703a, 704a, 705a, and 706a, respectively. Again, this communication may be done either via a Wi-Fi connection or an Ethernet link. Data may be exchanged between the LENSAR laser 701 and the Cassini Topographer 703 and the OR Microscope 706 via the use of USB Memory Sticks 707. A person of ordinary skill in the art would understand that this network may optionally include other devices useful in a hospital or a medical office, including personal computers or mobile devices. The network may download and/or upload a patient's medical history to a remote server. This information may include previously-acquired data regarding the patient's iris, and may be used by the system to ensure that the scanned iris belongs to the patient for whom the current treatment plan was developed. Other combinations of devices in this network would be recognized by a person of skill in the art.

In an embodiment of a network there is provided the ability to prevent interruption or disruption from other wireless networks or wireless devices that may be operating in the vicinity of the laser system, and the laser system's wireless. These networks and devices are prevented for interfering with or otherwise accidentally or unintentionally effecting the laser system and laser system network. In a preferred embodiment of an example of a wireless network for the laser surgery system, the wireless technology can be IEEE 802.11n Wi-Fi, which provides a max net data rate of 600 megabits per second (Mbps), and is backward compatible to IEEE 802.11g Wi-Fi and thus IEEE 802.11 b. Other Wi-Fi technologies, data rates and features are contemplated.

Quality of Service (QoS) in an embodiment can be maintained, for example, by having abundant bandwidth compared with relatively small per patient data sizes, the use of TCP/IP and the availability of backup configuration of wired data transfer or data transfer via USB memory sticks. Further, in preferred embodiments, all wireless import functionality, certificate purchase, and remote diagnostics occur only after a request from the operator, e.g., the surgeon. Similarly, export functionality, including printing, in an embodiment preferably only occurs after a procedure is completed. In an embodiment, no wireless data is transmitted or received during scanning or treatment of the patient. It being understood that these communication features, and safeguards, other communications features, other safe guards, and other protocols, and variations and combinations of these can be utilized.

A system and method for increasing the amplitude of accommodation and/or changing the refractive power of lens material of a natural crystalline lens is provided. Generally, there is provided methods and systems for delivering a laser beam to a lens of an eye in a plurality of sectional patterns results in the shaped structural weakening of the lens.

A system and method for softening, sectioning, and cutting a natural crystalline lens is provided. Generally, the system comprises a laser, optics for delivering the laser beam and a control system for delivering the laser beam to the lens in a particular pattern. There is further provided a device for determining the shape and position of the lens with respect to the laser. There is yet further provided a method and system for delivering a laser beam in the lens of the eye in a predetermined shot pattern that utilize as series of shots that form a shell cut, a partial shell cut, a laser suture cut and/or a volumetric shaped removal, which may essentially following the shape of a suture layer of the lens.

Accordingly, there are provided methods and systems for delivering a laser beam to a lens of an eye in a plurality of sectional patterns such that the laser beam is directed toward a first portion of the lens of the eye in a first predetermined sectional pattern and the laser beam is directed toward a second section of the lens of the eye in a second predetermined sectional pattern, which is different from the first pattern, wherein the combination and placement of the first and second sectional patterns results in the shaped structural weakening of the lens.

There is further provided a method and system for providing a first and a second sectional pattern to different portions of the lens of the eye resulting in shaped structural weakening, e.g., selective cutting, sectioning and combinations thereof, of the lens.

Moreover, the timing of the delivery of the first and second shot patterns can be varied such that the first and second shot patterns are combined into a single pattern, the first shot pattern is delivered to the lens before the second shot pattern, the second shot pattern is delivered to the lens before the first shot pattern, the delivery of the first and second shot patterns are interspersed, e.g., one or more of shots of the first shot pattern are followed by one or more shots of the second shot pattern, which are then followed by one or more shots of the first pattern.

Accordingly, there are provided methods and systems for delivering a laser beam to a lens of an eye in a plurality of sectional patterns such that the laser beam is directed toward a first portion of the lens of the eye in a first predetermined sectional pattern and the laser beam is directed toward a second section of the lens of the eye in a second predetermined sectional pattern, which is different from the first pattern, wherein the combination and placement of the first and second sectional patterns results in the shaped structural weakening of the lens.

The change to refractive error can be a predicted error or an actual error that has been determined. Moreover, the timing of the delivery of the first and second shot patterns can be varied such that the first and second shot patterns are combined into a single pattern, the first shot pattern is delivered to the lens before the second shot pattern, the second shot pattern is delivered to the lens before the first shot pattern, the delivery of the first and second shot patterns are interspersed, e.g., one or more of shots of the first shot pattern are followed by one or more shots of the second shot pattern, which are then followed by one or more shots of the first pattern.

There is also provided a method and system for determining adjustments to refractive errors in the lens of an eye relating to the treatment of presbyopia that comprises a first shot pattern for the delivery of a laser to the lens of an eye for the purpose of improving accommodative amplitude of the lens, a second shot pattern for the delivery of a laser to the eye, such that the second shot pattern is based at least in part upon any change in refractive error as a result of the first shot pattern, wherein the first shot pattern is delivered to the lens, the change in refractive error is determined by observation of the lens after delivery of the first shot pattern, and the second shot pattern is then selected based at least in part upon said observed change in refraction. Accordingly, the second shot pattern can be delivered to the lens of the eye or to the cornea of the eye. Moreover, the laser for delivery of the first shot pattern and the laser for delivery of the second shot pattern may be different. As used herein the terms "first" and "second" as used to describe a "first shot pattern" and "second shot pattern," unless specifically provided otherwise, do not implicate timing, pattern sequence, or similarly or differences in lasers. These terms indicate that there are two patterns, one pattern which may be different from the other.

There is provided an embodiment of a system and method for delivering a laser beam to a lens of an eye in a plurality of patterns, which system and method in general comprise providing a laser, providing an optical path for directing a laser beam from the laser to the lens of the eye, directing the laser beam in a first pattern on a first portion of the lens of the eye, the first pattern generally following the shape of the outer surface of the lens of the eye, directing the laser beam in a second pattern on a second portion of the lens of the eye, the second pattern having a pattern to cover a specific volume of the second portion of the lens of the eye and wherein the relationship of the first pattern to the second pattern being such that the first pattern is positioned within the lens closer to the lens outer surface than the second pattern; and, both the first and second patterns positioned within the lens of the eye such that they avoid the central portion of the lens of the eye. In this system and method the second pattern may be cubic, the first shot pattern may be a plurality of nested shells, the first shot pattern may comprises a plurality of nested shells that follows the anterior surface of the lens of the eye, or other combinations and of patterns disclosed and taught herein. These shot patterns may further be delivered to the lens of the eye in a random manner. These shot patterns may still further have a central area avoided wherein the central area avoided has a width of about 1 mm centered approximately on the optical axis of the lens, wherein the central area avoided has is cylindrical in shape and has a diameter greater than about 1 mm centered approximately around the optical axis of the lens, wherein the central area avoided has a width of about 1.5 mm centered approximately on the optical axis of the lens, wherein the central area avoided is cylindrical in shape and has a diameter greater than about 1.5 mm centered approximately around the optical axis of the lens, wherein the central area avoided has a width of about 0.2 mm to about 4 mm centered approximately on the optical axis of the lens, wherein the central area avoided is cylindrical in shape and has a diameter of about 0.2 mm to about 4 mm centered approximately around the optical axis of the lens, wherein the central area avoided is cylindrical in shape and has a diameter of about 0.2 mm to about 4 mm centered approximately around the optical axis of the lens, wherein the central area avoided has a diameter of about 0.5 mm to about 3 mm centered approximately around the optical axis of the lens, wherein the central area avoided is cylindrical in shape and has a diameter of about 2 mm centered approximately around the optical axis of the lens, and wherein the second pattern is different from the first pattern, as well as other. These shot patterns may further be delivered to the lens of the eye in a random manner.

The various embodiments of devices, systems, laser shot patterns, activities, and operations set forth in this specification may be used with, in or by, various measuring, diagnostic, surgical and therapeutic laser systems, in addition to those embodiments of the Figures and disclosed in this specification. The various embodiments of devices, systems, laser shot patterns, activities, and operations set forth in this specification may be used with: other measuring, diagnostic, surgical and therapeutic systems that may be developed in the future: with existing measuring, diagnostic, surgical and therapeutic laser systems, which may be modified, in-part, based on the teachings of this specification; and with other types of measuring, diagnostic, surgical and therapeutic systems. Further, the various embodiments of devices, systems, laser shot patterns, activities, and operations set forth in this specification may be used with each other in different and various combinations. Thus, for example, the configurations provided in the various embodiments of this specification may be used with each other; and the scope of protection afforded the present inventions should not be limited to a particular embodiment, configuration or arrangement that is set forth in a particular embodiment, example, or in an embodiment in a particular Figure.

The inventions may be embodied in other forms than those specifically disclosed herein without departing from their spirit or essential characteristics. The described embodiments are to be considered in all respects only as illustrative and not restrictive.

What is claimed:

1. A system for performing laser cataract surgery comprising a means to determine a material property of a structure of the eye, wherein the structure comprises a cataract and the material property comprises one of a plurality of predetermined cataract grades and a means for providing a therapeutic laser pattern base at least in part on a determined material property, wherein the laser pattern is predetermined for the cataract grade; and, wherein the plurality of cataract grades is selected from a group consisting of five grades; wherein grade one consists of a cataract with no detectable nucleus, grade two consists of a cataract wherein the nucleus is detectable, but not dense, grade three consists of a cataract with a dense nucleus, grade four consists of a cataract with an extremely dense nucleus, and grade five consists of a cataract wherein no light can transmit through the material.

2. The system of claim 1, wherein the system further comprises a wireless network and has access to a patient's EMR, and can automatically bill the patient, and their insurance, for the procedure.

* * * * *